United States Patent [19]

Takaya et al.

[11] Patent Number: 4,973,699
[45] Date of Patent: Nov. 27, 1990

[54] CEPHEM COMPOUNDS AND PROCESSES FOR PREPARATION THEREOF

[75] Inventors: Takao Takaya, Kawanishi; Zenzaburo Tozuka, Toyonaka; Nobuyoshi Yasuda, Nishinomiya; Shintaro Nishimura, Settsu, all of Japan

[73] Assignee: Fujisawa Pharmaceutical Co., Ltd., Osaka, Japan

[21] Appl. No.: 352,989

[22] Filed: May 17, 1989

Related U.S. Application Data

[62] Division of Ser. No. 828,527, Feb. 12, 1986, Pat. No. 4,861,769.

[30] Foreign Application Priority Data

Feb. 18, 1985 [GB] United Kingdom ......... 8504072

[51] Int. Cl.$^5$ ............................. C07D 285/08
[52] U.S. Cl. ................................. 548/128
[58] Field of Search ..................... 548/194, 128

[56] References Cited

U.S. PATENT DOCUMENTS 4,366,153 12/1982 Takaga ..................... 548/194
4,468,515 8/1984 Teraji ....................... 548/128

FOREIGN PATENT DOCUMENTS 95778 12/1983 European Pat. Off. ......... 540/355

Primary Examiner—Robert Gerstl
Attorney, Agent, or Firm—Oblon, Spivak, McClelland, Maier & Neustadt

[57] ABSTRACT

A compound of the formula:

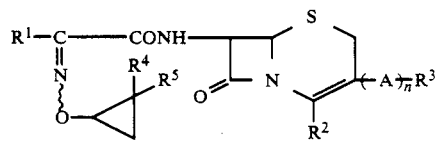

wherein
$R^1$ is lower alkyl, lower alkanoyl, aryl, ar(lower)alkyl or a heterocyclic group, each of which may have suitable substituent(s),
$R^2$ is carboxy or protected carboxy,
$R^3$ is hydrogen, halogen, hydroxy, lower alkoxy, acyloxy, lower alkylthio, lower alkenyl, lower alkenylthio, lower alkynyl, heterocyclothio or a heterocyclic group, in which lower alkylthio, lower alkenyl, lower alkenylthio, heterocyclicthio and a heterocyclic group may have suitable substituent(s),
$R^4$ and $R^5$ are each hydrogen, halogen or arylthio,
A is lower alkylene, and
n is an integer of 0 or 1, and a pharmaceutically acceptable salt thereof, processes for preparation thereof and pharmaceutical composition comprising the same.

1 Claim, No Drawings

CEPHEM COMPOUNDS AND PROCESSES FOR PREPARATION THEREOF

This is a division of application Ser. No. 06/828,527, filed on Feb. 12, 1986, now U.S. Pat. No. 4,861,769.

The present invention relates to new cephem compounds and pharmaceutically acceptable salts thereof. More particularly, it relates to new cephem compounds and pharmaceutically acceptable salts thereof, which have antimicrobial activities, to processes for preparation thereof, to a pharmaceutical composition comprising the same, and to a method for treating infectious diseases in human being or animals.

Accordingly, one object of the present invention is to provide the new cephem compounds and pharmaceutically acceptable salts thereof, which are highly active against a number of pathogenic microorganisms.

Another object of the present invention is to provide processes for the preparation of the cephem compounds and salts thereof.

A further object of the present invention is to provide a pharmaceutical composition comprising, as an active ingredient, said cephem compounds or their pharmaceutically acceptable salts.

Still further object of the present invention is to provide a method for treating infectious diseases caused by pathogenic microorganisms, which comprises administering said cephem compounds to infected human being or animals.

The object cephem compounds are novel and can be represented by the following general formula [I]:

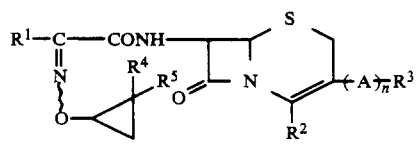

wherein
$R^1$ is lower alkyl, lower alkanoyl, aryl, ar(lower)alkyl or a heterocyclic group, each of which may have suitable substituent(s),
$R^2$ is carboxy or protected carboxy,
$R^3$ is hydrogen, halogen, hydroxy, lower alkoxy, acyloxy, lower alkylthio, lower alkenyl, lower alkenylthio, lower alkynyl, heterocyclicthio or a heterocyclic group, in which lower alkylthio, lower alkenyl, lower alkenylthio, heterocyclicthio and a heterocyclic group may have suitable substituent(s),
$R^4$ and $R^5$ are each hydrogen, halogen or arylthio,
A is lower alkylene, and
n is an integer of 0 or 1.

As to the object compounds [I], the following points are to be noted.

That is, the object compounds [I] include syn isomer, anti isomer and a mixture thereof at the oxime portion. Syn isomer means one geometrical isomer having the partial structure represented by the following formula:

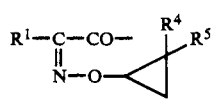

(wherein $R^1$, $R^4$ and $R^5$ are each as defined above), and anti isomer means the other geometrical isomer having the partial structure represented by the following formula:

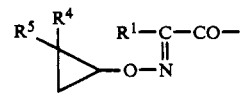

(wherein $R^1$, $R^4$ and $R^5$ are each as defined above), and all of such geometrical isomers and mixture thereof are included within the scope of this invention.

In the present specification and claim, the partial structure of these geometrical isomers and mixture thereof are represented for convenient sake by the following formula:

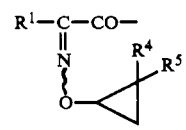

(wherein $R^1$, $R^4$ and $R^5$ are each as defined above).

Another point to be noted is the object compounds [I] may include cis isomer, trans isomer and a mixture thereof at the cyclopropyl ring. For example, when one of $R^4$ and $R^5$ is halogen and the other is hydrogen, cis isomer means one geometrical isomer having the partial structures represented by the following formulas:

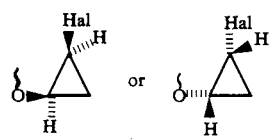

(wherein Hal is halogen),
and trans isomer means the other geometrical isomer having the partial structures represented by the following formulas:

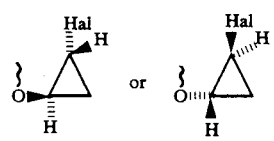

(wherein Hal is as defined above),
and all of such geometrical isomers and mixture thereof are also included within the scope of this invention.

In the present specification and claim, the partial structures of these geometrical isomers and mixture thereof are represented for convenient sake by the following formula:

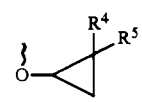

(wherein $R^4$ and $R^5$ are each as defined above).

The cephem compounds [I] of the present invention can be prepared by processes as illustrated in the following.

Process 1
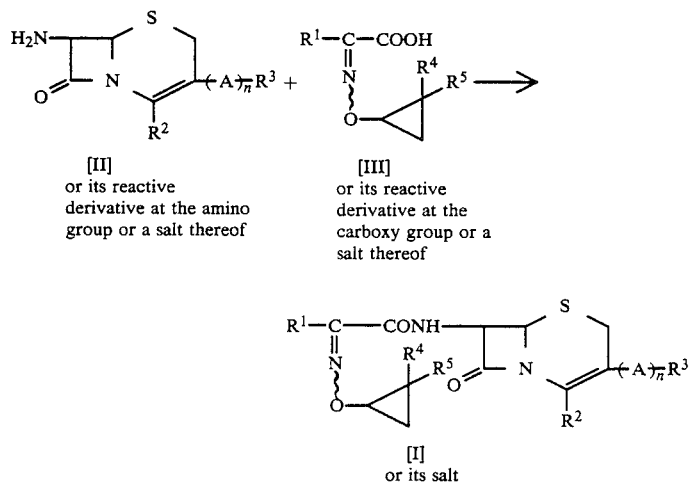
[II]
or its reactive
derivative at the amino
group or a salt thereof
[III]
or its reactive
derivative at the
carboxy group or a
salt thereof
[I]
or its salt
Process 2
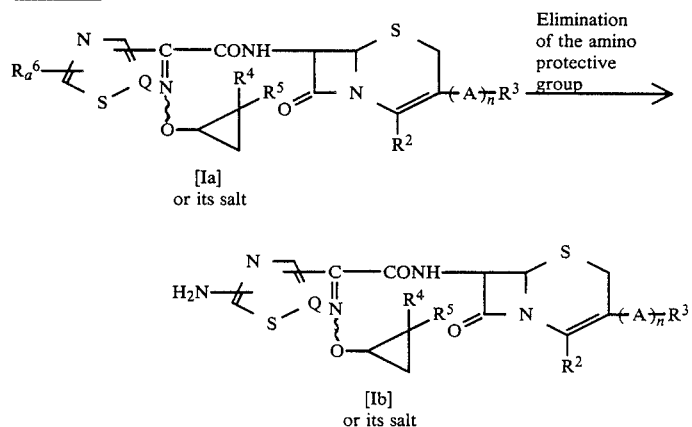
[Ia]
or its salt
[Ib]
or its salt
Process 3
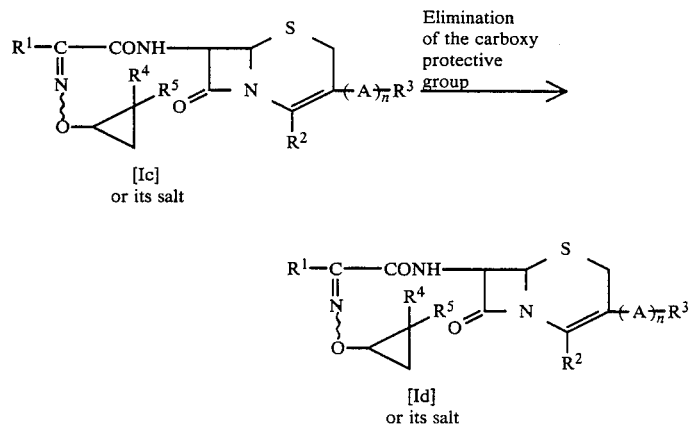
[Ic]
or its salt
[Id]
or its salt
Process 4
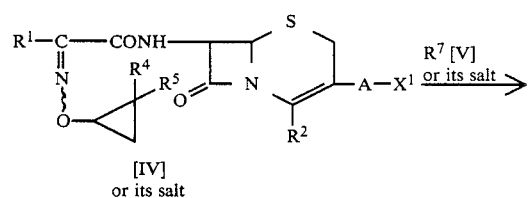
[IV]
or its salt -continued
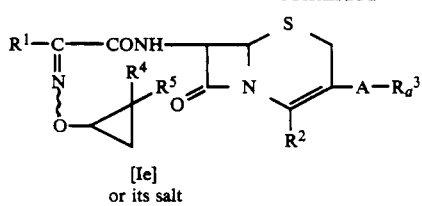
[Ie]
or its salt
Process 5
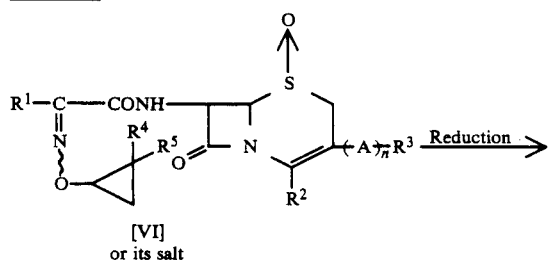
[VI]
or its salt
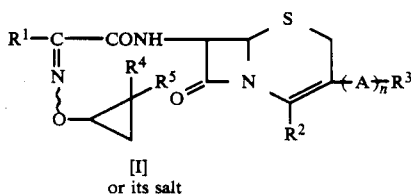
[I]
or its salt
Process 6
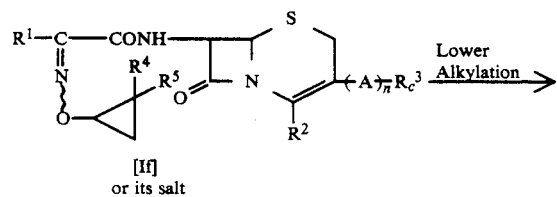
[If]
or its salt
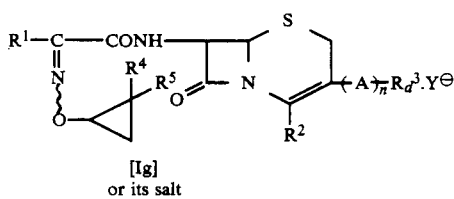
[Ig]
or its salt
Process 7
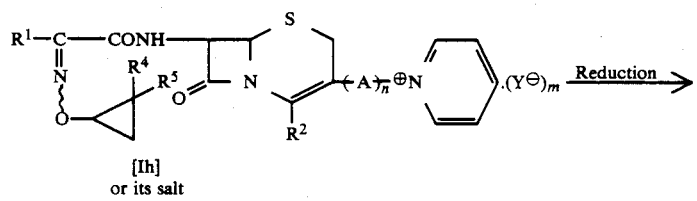
[Ih]
or its salt
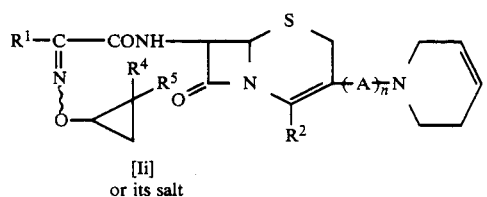
[Ii]
or its salt
Process 8

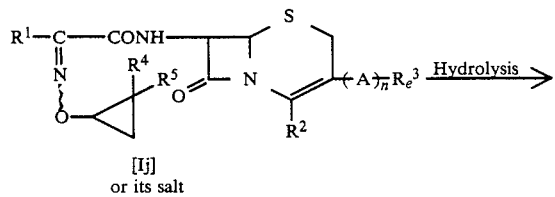

[Ij]
or its salt

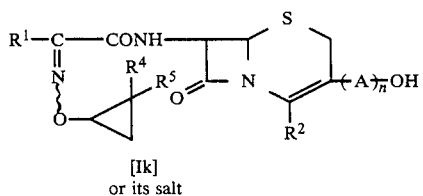

[Ik]
or its salt wherein
$R_a^2$ is protected carboxy,
$R_a^3$ is lower alkylthio, lower alkenylthio, a heterocyclic group having a quaternary nitrogen atom, or heterocyclicthio, each of which may have suitable substituent(s),
$R_c^3$ is pyridyl(lower)alkenylthio or pyridylthio(lower)alkenyl,
$R_d^3$ is [1-lower alkylpyridinio](lower)alkenylthio or [1-lower alkylpyridinio]thio(lower)alkenyl,
$R_e^3$ is acyloxy,
$R_a^6$ is protected amino,
$R^7$ is an N-containing unsaturated heterocyclic compound optionally substituted with suitable substituent(s), or a compound of the formula:
$R_b^3$—H in which $R_b^3$ is lower alkylthio, lower alkenylthio or heterocyclicthio, each of which may have suitable substituent(s),
m is an integer of 0 or 1,
Q is CH or N,
$X^1$ is a leaving group,
$Y^\ominus$ is an anion, and
$R^1$, $R^2$, $R^3$, $R^4$, $R^5$, A and n are each as defined above.

In the above and subsequent descriptions of this specification, suitable examples of the various definitions are explained in detail as follows:

The term "lower" is intended to mean 1 to 6 carbon atom(s), preferably 1 to 4 carbon atom(s), unless otherwise indicated.

Suitable "lower alkyl" may be straight or branched ones such as methyl, ethyl, propyl, isopropyl, butyl, isobutyl, tert-butyl, pentyl, hexyl or the like.

Suitable "lower alkanoyl" may be formyl, acetyl, propionyl, hexanoyl, pivaloyl or the like.

Said lower alkanoyl includes its derivative at the carbonyl group such as acetal [e.g. dimethyl acetal, diethyl acetal, ethylene acetal, etc.] thioacetal [e.g. dimethyl dithioacetal, diethyl dithioacetal, ethylene dithioacetal, etc.] or the like.

Suitable "aryl" may be phenyl, tolyl, xylyl, naphthyl or the like.

Suitable "ar(lower)alkyl" may be benzyl, phenethyl, benzhydryl, trityl or the like.

The heterocyclic group and the heterocyclic moiety of the heterocyclicthio group may include saturated or unsaturated, monocyclic or polycyclic heterocyclic group containing at least one hetero-atom selected from oxygen, sulfur and nitrogen atoms.

Preferable heterocyclic group may be unsaturated, 3 to 8-membered, more preferably 5 or 6-membered heteromonociclic group containing 1 to 4-nitrogen atom(s), for example, pyrrolyl, pyrrolinyl, imidazolyl, imidazolio, pyrazolyl, pyrazolio, pyridyl, pyridyl N-oxide, pyridinio, dihydropyridyl, tetrahydropyridyl [e.g. 1,2,3,6-tetrahydropyridyl, etc.], pyrimidyl, pyrimidinio, pyrazinyl, pyrazinio, pyridazinyl, pyridazinio, triazinyl [e.g. 1,3,5-triazinyl, 1,2,4-triazinyl and 1,2,3-triazinyl], tetrahydrotriazinyl [e.g. 1,2,5,6-tetrahydro-1,2,4-triazinyl, 1,4,5,6-tetrahydro-1,2,4-triazinyl, etc.], triazinio, triazolyl [e.g. 4H-1,2,4-triazolyl, 1H-1,2,3-triazolyl and 2H-1,2,3-triazolyl], triazolio, tetrazinyl, tetrazonio, tetrazolyl [e.g. 1H-tetrazolyl and 2H-tetrazolyl], tetrazolio, etc ; saturated, 3 to 8-membered heteromonocyclic group containing 1 to 4 nitrogen atom(s), for example, pyrrolidinyl, imidazolidinyl, piperidino, piperazinyl, etc.;

unsaturated, condensed heterocyclic group containing 1 to 5 nitrogen atom(s), for example, indolyl, isoindolyl, indolizynyl, benzimidazolyl, benzimidazolio, quinolyl, quinolinio, isoquinolyl, isoquinolinio, indazolyl, indazolio, benzotriazolyl, tetrazolopyridyl, tetrazolopyridazinyl, [e.g. tetrazolo[1,5-b]pyridazinyl, etc.], dihydrotriazolopyridazinyl, 1H-1-(1-pyrindinyl), 5H-1-(1-pyrindinio), 1H-2-(1-pyrindinyl), 1H-2-(2-pyrindinio), 6,7-dihydro-5H-1-(1-pyrindinio), 6,7-dihydro-5H-1-(2-pyrindinyl), etc.;

unsaturated, 3 to 8-membered heteromonocyclic group containing 1 to 2 oxygen atom(s) and 1 to 3 nitrogen atom(s), for example, oxazolyl, oxazolio, isoxazolyl, oxadiazolyl [e.g. 1,2,4-oxadiazolyl, 1,3,4-oxadiazolyl, 1,2,5-oxadiazolyl], oxadiazolio, etc.;

saturated, 3 to 8-membered heteromonocyclic group containing 1 to 2 oxygen atom(s) and 1 to 3 nitrogen atom(s), for example, morpholino, sydnonyl, etc.;

unsaturated, condensed heterocyclic group containing . 1 to 2 oxygen atom(s) and 1 to 3 nitrogen atom(s), for example, benzoxazolyl, benzoxadiazolyl, etc.;

unsaturated, 3 to 8-membered heteromonocyclic group containing 1 to 2 sulfur atom(s) and 1 to 3 nitrogen atom(s), for example, thiazolyl, thiazolio, isothiazolyl, thiadiazolyl [e.g. 1,2,3-thiadiazolyl, 1,2,4-thiadiazolyl, 1,3,4-thiadiazolyl, 1,2,5-thiadiazolyl], thiadiazolio, dihydrothiazinyl, etc.;

saturated, 3 to 8-membered heteromonocyclic group containing 1 to 2 sulfur atom(s) and 1 to 3 nitrogen atom(s), for example, thiazolidinyl, etc.; unsaturated, 3 to 8-membered heteromonocyclic group containing 1 to 2 sulfur atom(s), for example, thienyl, etc.;

unsaturated, condensed heterocyclic group containing 1 to 2 sulfur atom(s) and 1 to 3 nitrogen atom(s), for example, benzothiazolyl, benzothiadiazolyl, etc.;

unsaturated, 3 to 8-membered heteromonocyclic group containing an oxygen atom, for example, furyl, etc.;

unsaturated, 3 to 8-membered heteromonocyclic group containing an oxygen atom and 1 to 2 sulfur atom(s), for example, oxathiolyl, oxathiinyl, etc.;

unsaturated, condensed heterocyclic group containing 1 to 2 sulfur atom(s), for example, benzothienyl, etc.;

unsaturated, condensed heterocyclic group containing an oxygen atom and 1 to 2 sulfur atom(s), for example, benzoxathiinyl, etc., or the like.

Suitable "protected carboxy" may be a conventional one used in penicillin or cephalosporin field such as an esterified carboxy, or the like, and concrete examples of the ester moiety in said esterified carboxy group may be the ones such as lower alkyl ester [e.g. methyl ester, ethyl ester, propyl ester, isopropyl ester, butyl ester, isobutyl ester, tert-butyl ester, pentyl ester, hexyl ester, 1-cyclopropylethyl ester, etc.] which may have suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, 2-acetoxyethyl ester, 2-propionyloxyethyl ester, hexanoyloxymethyl ester, etc.] lower alkanesulfonyl(lower)alkyl ester [e.g. 2-mesylethyl ester, etc.] or mono(or di or tri)halo(lower)alkyl ester [e.g. 2-iodoethyl ester, 2,2,2-trichloroethyl ester, etc.]; lower alkenyl ester [e.g. vinyl ester, allyl ester, etc.]; lower alkynyl ester [e.g. ethynyl ester, propynyl ester, etc.]; ar(lower)alkyl ester which may have suitable substituent(s) [e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tertbutylbenzyl ester, etc.]; aryl ester which may have suitable substituent(s) [e.g. phenyl ester, 4-chlorophenyl ester, tolyl ester, 4-tert-butylphenyl ester, xylyl ester, mesityl ester, cumenyl ester, etc.]; or the like.

Suitable "halogen" may include chlorine, bromine, fluorine and iodine.

Suitable "lower alkoxy" may be methoxy, ethoxy, propoxy, isopropoxy, butoxy, isobutoxy, tert-butoxy, pentyloxy, hexyloxy or the like, in which the preferred one may be $C_1-C_4$ alkoxy.

Suitable "acyloxy" may be lower alkanoyloxy [e.g. formyloxy, acetoxy, propionyloxy, hexanoyloxy, pivaloyloxy, etc.], halo(lower)alkanoyloxy e.g. chloroacetoxy, bromopropionyloxy, trifluoroacetoxy, etc.], lower alkoxycarbonyloxy [e.g. methoxycarbonyloxy, ethoxycarbonyloxy, tert-butoxycarbonyloxy, tert-pentyloxycarbonyloxy, hexyloxycarbonyloxy, etc.], aroyloxy [e.g. benzoyloxy, toluoyloxy, naphthoyloxy, etc.], ar(lower)alkanoyloxy [e.g. phenylacetoxy, phenylpropionyloxy, etc.], aryloxycarbonyloxy [e.g. phenoxycarbonyloxy, naphthyloxycarbonyloxy, etc.], aryloxy(lower)alkanoyloxy [e.g. phenoxyacetoxy, phenoxypropionyloxy, etc.], arylglyoxyloyloxy [e.g. phenylglyoxyloyloxy, naphthylglyoxyloyloxy, etc.], ar(lower)alkoxycarbonyloxy [e.g. benzyloxycarbonyloxy, phenethyloxycarbonyloxy, etc.], carbamoyloxy, lower alkanesulfonyloxy [e.g. methanesulfonyloxy, ethanesulfonyloxy, etc.], arenesulfonyloxy [e.g. benzenesulfonyloxy, toluenesulfonyloxy, etc.], or the like, in which the preferred one may be $C_1-C_4$ alkanoyloxy and carbamoyloxy.

Suitable "lower alkylthio" may be methylthio, ethylthio, propylthio, isopropylthio, butylthio, isobutylthio, tert-butylthio, pentylthio, hexylthio or the like, in which the preferred one may be $C_1-C_7$ alkylthio Suitable "lower alkenyl" may be vinyl, allyl, 3-butenyl, 4-pentenyl, 5-hexenyl, isopropenyl or the like, in which the preferred one may be $C_2-C_4$ alkenyl.

Suitable "lower alkenylthio" may be vinylthio, allylthio, 3-butenylthio, 4-pentenylthio, 5-hexenylthio, isopentenylthio or the like, in which the preferred one may be $C_2-C_4$ alkenylthio.

Suitable "lower alkynyl" may be ethynyl, 1-propynyl, propargyl, 3-butynyl, 4-pentynyl, 5-hexynyl, or the like, in which the preferred one may be $C_2-C_4$ alkynyl.

Suitable "arylthio" may be phenylthio, tolylthio, xylylthio, naphthylthio or the like, in which the preferred one may be $C_6-C_{10}$ arylthio.

Suitable "lower alkylene" may be straight or branched ones such as methylene, ethylene, trimethylene, tetramethylene, pentamethylene, hexamethylene, propylene, ethylethylene, propylethylene, isopropylethylene, methylpentamethylene or the like, in which the preferred one may be $C_1-C_4$ alkylene and the most preferred one is methyl.

Suitable "a heterocyclic group having a quaternary nitrogen atom" may be pyridinio, imidazolio, pyrazolio, pyrimidinio, pyrazinio, pyridazinio, triazinio, triazolio, tetrazinio, tetrazolio, oxazolio, oxadiazolio, thiazolio, thiadiazolio, pyrindinio [e.g. 5H-1-(1-pyrindinio), 1H-2-(2-pyrindinio), 6,7-dihydro-5H-1-(1-pyrindinio), etc.], benzimidazolio, indazolio, quinolinio, isoquinolino, or the like.

Suitable "an N-containing unsaturated heterocyclic compound" may be pyridine, imidazole, pyrazole, pyrimidine, pyrazine, pyridazine, triazine, triazole, tetrazine, tetrazole, oxazole, oxadiazole, thiazole, thiadiazole, pyrindine [e.g. 5H-1-pyrindine, 1H-2-pyrindine, 6,7-dihydro-5H-1-pyrindine, etc.], benzimidazole, indazole, quinoline, isoquinoline, or the like.

Suitable "pyridyl(lower)alkenylthio" may be 2-(2-pyridyl)vinylthio, 2-(3-pyridyl)vinylthio, 2-(4-pyridyl)-vinylthio, 3-(3-pyridyl)allylthio, 4-(3-pyridyl)-3-butenylthio, or the like.

Suitable "pyridylthio(lower)alkenyl" may be 2-(2-pyridyl)thiovinyl, 2-(3-pyridyl)thiovinyl, 2-(4-pyridyl)-thiovinyl, 3-(3-pyridyl)thioallyl, 4-(3-pyridyl)thio-3-butenyl, or the like.

Suitable "[[1-lower alkylpyridinio](lower)alkenylthio" may be 2-(1-methyl-2-pyridinio)vinylthio, 2-(1-methyl-3-pyridinio)vinylthio, 2-(1-ethyl-3-pyridinio)vinylthio, 2-(1-methyl-4-pyridinio)vinylthio, 3-(1-methyl-3-pyridinio)allylthio, 4-(1-methyl-3-pyridinio)-3-butenylthio, or the like.

Suitable "[1-lower alkylpyridinio]thio(lower)alkenyl" may be 2-(1-methyl-2-pyridinio)thiovinyl, 2-(1-methyl-3pyridinio)thiovinyl, 2-(1-ethyl-3-pyridinio)thiovinyl, 2-(1-methyl-4-pyridinio)thiovinyl, 3-(1-methyl-3)pyridinio)thioallyl, 4-(1-methyl-3-pyridinio)thio-3butenyl, or the like.

Suitable protective group in the protected amino group may be lower alkanoyl [e.g. formyl, acetyl, propionyl, hexanoyl, pivaloyl, etc.], mono(or di or tri)halo(lower)alkanoyl [e.g. chloroacetyl, trifluoroacetyl, etc.], lower alkoxycarbonyl [e.g. methoxycarbonyl, ethoxycarbonyl, tert-butoxycarbonyl, tert-pentyloxycarbonyl, hexyloxycarbonyl, etc.], aroyl [e.g. benzoyl, toluoyl, naphthoyl, etc.], ar(lower)alkanoyl [e.g. phenylacetyl, phenylpropionyl, etc.], aryloxycarbonyl [e.g. phenoxycarbonyl, naphthyloxycarbonyl, etc.], aryloxy(lower)alkanoyl [e.g. phenoxyacetyl, phenoxypropionyl, etc.], arylglyoxyloyl [e.g. phenylglyoxyloyl, naphthylglyoxyloyl, etc.], ar(lower)alkoxycarbonyl which may have suitable substituent(s) [e.g. benzyloxycarbonyl, phenethyloxycarbonyl, p-nitrobenzyloxycarbonyl, etc.], ar(lower)alkyl such as mono or di or triphenyl(lower)alkyl [e.g. benzyl, phenethyl, benzhydryl, trityl, etc.], or the like.

The lower alkyl, lower alkanoyl, aryl, ar(lower)alkyl and heterocyclic groups for $R^1$ may have suitable substituent(s) such as amino, hydroxy, the above-mentioned lower alkyl, halogen [e.g. chlorine, bromine, fluorine and iodine protected amino as exemplified above, lower alkoxy [e.g. methoxy, ethoxy, propoxy, isopropoxy, butoxy, isobutoxy, tert-butoxy, pentyloxy, hexyloxy, etc.], halo(lower)alkyl [e.g. chloromethyl, chloroethyl, dibromomethyl, trifluoromethyl, iodopropyl, etc.]or the like.

The lower alkylthio, lower alkenylthio and heterocyclicthio groups for $R^3$, $R_a{}^3$ and $R_b{}^3$; the lower alkenyl and heterocyclic groups for $R^3$; the heterocyclic group having a quaternary nitrogen atom for $R_a{}^3$; and the N-containing unsaturated heterocyclic compound for $R^7$ may have suitable substituent(s) such as hydroxy; oxo; carboxy; cyano; carbamoy; or the above-mentioned halogen lower alkyl, lower alkylthio, lower alkenyl, a heterocyclic or heterocyclicthio group as exemplified for $R^1$ and $R^3$; or the like, in which a heterocyclic and heterocyclicthio group may substituted with lower alkyl as exemplified above.

Suitable "leaving group" for $X^1$ may be an acid residue such as the above-mentioned acyloxy, azido, halide [e.g. chloride, bromide, iodide, etc.] or the like.

Suitable anion may be halide anion such as chloride anion, bromide anion, fluoride anion, iodide anion, or the like.

Particularly, the preferred embodiments of the symbols "$R^1$", "$R^2$", "$R^3$", "$R^4$", "$R^5$", "A" and "n" of the object compounds [I] are as follows: The symbol "$R^1$" may be represented by the following formula:

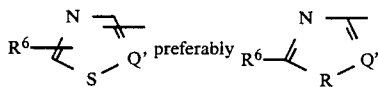

in which $R^6$ is amino or protected amino [preferably acylamino {more preferably lower alkanoylamino (e.g. formylamino, acetylamino, propionylamino, butyrylamino, valerylamino, pentanoylamino, hexanoylamino, etc.) and mono(or di or tri)halo(lower)alkanoylamino (e.g. chloroacetylamino, dichloroacetylamino, trifluoroacetylamino, etc.)} and ar(lower)alkylamino {more preferably mono or di or triphenyl(lower)alkylamino (e.g. benzylamino, phenethylamino, benzhydrylamino, tritylamino, etc.)}] and Q is CH or N.

The partial formula:

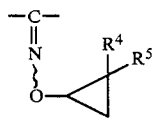

may be a syn isomer of the formula:

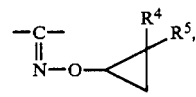

in which $R^4$ and $R^5$ are each hydrogen, halogen (e.g. chlorine, bromine, fluorine, iodine) and arylthio [preferably $C_6$–$C_{10}$ arylthio (e.g. phenylthio, tolylthio, xylylthio, cumenylthio, naphthylthio, etc.)].

The partial formula: $-(A)_{\overline{n}}R^3$ may alternatively be represented by the single symbol "Z", in which Z is hydrogen; halogen [e.g. chlorine, bromine, fluorine, iodine]; lower alkoxy [e.g. methoxy, ethoxy, propoxy, isopropoxy, butoxy, isobutoxy, tert-butoxy, pentyloxy, hexyloxy, etc ]; lower alkylthio [e.g. methylthio, ethylthio, propylthio, isopropylthio, butylthio, isobutylthio, tert-butylthio, pentylthio, hexylthio, etc.]; lower alkenyl [e.g. vinyl, allyl, 3-butenyl, 4-pentenyl, 5-hexenyl, isopropenyl, etc.]; dihalo(lower)alkenyl [e.g. dichlorovinyl, dibromovinyl, difluorovinyl, etc.]; lower alkynyl [e.g. ethynyl, 1-propynyl, propargyl, 3-butynyl, 4-pentynyl, 5-hexynyl, etc.]; hydroxymethyl; acyloxymethyl [preferably lower alkanoyloxymethyl (e.g. formyloxymethyl, acetoxymethyl, propionyloxymethyl, hexanoyloxymethyl, pivaloyloxymethyl, etc.) and carbamoyloxymethyl]; halomethyl [e.g. chloromethyl, bromomethyl, iodomethyl, etc.]; heterocyclicmethyl optionally substituted with lower alkyl or carbamoyl [preferably unsaturated 5- or 6-membered heteromonocyclicmethyl containing 1 to 2 nitrogen atoms optionally substituted with lower alkyl or carbamoyl {more preferably pyridiniomethyl optionally substituted with one or two lower alkyl or carbamoyl (e.g. pyridiniomethyl, methylpyridiniomethyl, dimethylpyridiniomethyl, carbamoylpyridiniomethyl, etc.), pyrazoliomethyl optionally substituted with lower alkyl (e.g. pyrazoliomethyl, methylpyrazoliomethyl, etc.) and tetrahydropyridylmethyl (e.g. 1,2,3,6-tetrahydropyridylmethyl, etc.)} and pyrindiniomethyl {more preferably dihydropyrindiniomethyl (e.g. 6,7-dihydro-5H-pyrindiniomethyl, etc.)}]; heterocyclicthiomethyl optionally substituted with one to three substituents selected from lower alkyl, lower alkenyl, hydroxy, oxo and carboxy [preferably unsaturated 5- or 6-membered heteromonocyclicthiomethyl containing 1 to 4 nitrogen atoms optionally substituted with one to three substituents selected from lower alkyl, lower alkenyl and oxo {more preferably tetrazolylthiomethyl optionally substitutedwith lower alkyl or lower alkenyl (e.g. tetrazolylthiomethyl, methyltetrazolylthiomethyl, ethyltetrazolylthiomethyl, vinyltetrazolylthiomethyl, allyltetrazolylthiomethyl, etc.), tetrahydrotriazinylthiomethyl optionally substituted with lower alkyl and oxo (e.g. 5,6-dioxo-2-methyl-1,2,5,6-tetrahydro-1,2,4-triazinyl, 5,6-dioxo-4-methyl-1,4,5,6-tetrahydro-1,2,4-triazinyl, etc.) and 1-lower alkylpyridiniothiomethyl (e.g. 1-methylpyridiniothiomethyl, etc.)}, unsaturated 5-membered heteromonocyclicthiomethyl containing 1 to 2 nitrogen atoms and one sulfur atom optionally substituted with one or two substituents selected from lower alkyl, hydroxy and carboxy {more preferably isothiazolylthiomethyl optionally substituted with hydroxy and carboxy (e.g. isothiazolylthiomethyl, 3-hydroxy-4-carboxyisothiazolylthiomethyl, etc.), thiadiazolylthiomethyl optionally substituted with lower aklyl (e.g. 1,2,3-thiadiazolylthiomethyl, 1,2,4-thiadiazolylthiomethyl, 1,2,5-thiadiazolylthiomethyl, 1,3,4-thiadiazolylthiomethyl, 3-methyl-1,2,4-thiadiazolylthiomethyl, 5-methyl-1,3,4-thiadiazolylthiomethyl, etc.)} and tetrazolopyridazinylthiomethyl (e.g. tetrazolo[1,5-b]pyridazinylthiomethyl, etc.)]; heterocyclicthio(lower)alkenyl optionally substituted with lower alkyl [preferably unsaturated 6-membered heteromonocyclicthio(lower)alkenyl optionally substituted with lower alkyl {more preferably pyridylthio(lower)alkenyl (e.g. pyridylthiovinyl, etc.) and 1-lower alkylpyridiniothio(lower)alkenyl (e.g. 1-methyl-pyridiniothiovinyl, etc.}]; heterocyclic(lower)alkenylthio optionally substituted with lower alkyl [preferably unsaturated 6-membered heteromonocyclic(lower)alkenylthio optionally substituted with lower alkyl {more preferably pyridyl(lower)alkenylthio (e.g. pyridylvinylthio, etc.) and 1-lower alkylpyridinio(lower)alkenylthio (e.g. 1-methylpyridiniovinylthio, etc.]; or heterocyclic(lower)alkenylthiomethyl optionally substituted with lower alkyl [preferably unsaturated 6-membered heteromonocyclic(lower)alkenylthiomethyl optionally substituted with lower alkyl {more preferably pyridyl(lower)alkenylthiomethyl (e.g. pyridylvinylthiomethyl, etc.) and 1-lower alkylpyridinio(lower)alkenylthiomethyl (e.g. 1-methylpyridiniovinylthiomethyl, etc.].

The symbol "$R^2$" may be carboxy or pharmaceutically acceptable, or easily removable esterified carboxy [preferably ar(lower)alkoxycarbonyl optionally substituted with nitro, more preferably mono or di or triphenyl(lower)alkoxycarbonyl optionally substituted with nitro (e.g. benzyl, nitrobenzyl, benzhydryl, trityl, etc.), and the carboxy group can also be represented by the carboxy anion of the formula: $COO^{\ominus}$, in case that the heterocyclic moiety in $R^3$ bears a quaternary nitrogen atom in its moiety.

Suitable pharmaceutically acceptable salts of the object compounds [I] are conventional non-toxic salts and include a metal salt such as ah alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], an organic acid salt, [e.g. formate, acetate, trifluoroacetate, maleate, tartrate, methanesulfonate, benzenesulfonate, toluenesulfonate, etc.], an inorganic acid salt, hydrochloride, hydrobromide, sulfate, phosphate, etc.], a salt with an amino acid [e.g. arginine salt, aspartic acid salt, glutamic acid salt, etc.], an intermolecular or intramolecular quaternary salt, and the like.

The said intermolecular quaternary salt can be formed in case that the symbol "$R^3$" of the compounds [I] bears a heterocyclic moiety having nitrogen atom(s) such as pyridyl, pyrazolyl, pyrindinyl, or the like, and suitable examples of such salts may be pyridinium trifluoroacetate, pyridinium chloride, pyridinium iodide, pyridinium nitrate, pyrazolium trifluoroacetate, pyrazolium chloride, pyrazolium iodide, pyrindinium trifluoroacetate, pyrindinium chloride, pyrindinium iodide, or the like.

Further, the said intramolecular quaternary salt can be formed in case that the symbol "$R^3$" of the compounds[I] bears a heterocyclic moiety having quaternary nitrogen atom(s) such as pyridinio, pyrazolio, pyrindinio, or the like, and in such a case the symbol "$R^2$" are represented by a carboxy anion of the formula: $COO^{\ominus}$.

With respect to the salts of the compounds [Ia] to [Ik], it is to be noted that these compounds are included within the scope of the compounds [I], and accordingly the suitable salts of these compounds are to be referred to those as exemplified for the object compounds [I].

The processes for preparing the object compounds of the present invention are explained in detail in the following.

PROCESS 1

The compound [I] and its salt can be prepared by reacting a compound [II] or its reactive derivative at the amino group or a salt thereof with a compound [III] or its reactive derivative at the carboxy group or a salt thereof.

Suitable reactive derivative at the amino group of the compound [II] may include Schiff's base type imino or its tautomeric enamine type isomer formed by the reaction of the compound [II] with a carbonyl compound such as aldehyde, ketone or the like; a silyl derivative formed by the reaction of the compound [II] with a silyl compound such as bis(trimethylsilyl)acetamide. N-trimethylsilylacetamide, bis(trimethylsilyl)urea or the like; a derivative formed by reaction of the compound [II] with phosphorus trichloride or phosgene, and the like.

Suitable salts of the compound [II] and its reactive derivative can be referred to the ones as exemplified for the compounds [I].

Suitable reactive derivative at the carboxy group of the compound [III] may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl [$(CH_3)_2N^+=CH—$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester, with an N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, 1-hydroxy-6-chloro-1H-benzotriazole, etc.], and the like. These reactive derivatives can optionally be selected from them according to the kind of the compound [III] to be used.

Suitable salts of the compound [III] and its reactive derivative can be referred to the ones as exemplified for the compound [I].

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

When the compound [III] is used in a free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine, diphenylketene-N-cyclohexylimine; ethoxyacetylene; 1-alkoxy-1-chloroethylene, trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like.

The reaction temperature is not critical, and the reaction is usually carried out under cooling to warming.

PROCESS 2

The compound [Ib] and its salt can be prepared by subjecting a compound [Ia] or its salt to elimination reaction of the amino protective group.

This reaction is carried out in accordance with a conventional method such as hydrolysis, reduction or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, alkali metal alkanoate [e.g. sodium acetate, etc.] trialkylamine [e.g. trimethylamine, triethylamine, etc.], picoline, 1,5-diazabicyclo[4.3.0]-non-5-ene, 1,4-diazabicyclo[2.2.2]octane, 1,8-diazabicyclo[5.4.0]undec-7-ene, or the like. Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reaction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the abovementioned solvent, and other conventional solvent such as diethyl ether, dioxane, tetrahydrofuran, etc., or a mixture thereof. The reaction temperature is not critical and the reaction is usually carried out under cooling to warming.

PROCESS 3

The compound [Id] and its salt can be prepared by subjecting a compound [Ic] or its salt to elimination reaction of the carboxy protective group.

This reaction can be carried out in a similar manner to that of Process 2 mentioned in the above, and therefore the reaction mode and reaction conditions [e.g. base, acid, catalyst, solvent, reaction temperature, etc.] of this reaction are to be referred to those as explained in Process 2.

In case that the object compounds [Id] are intermolecular quaternary salts, they can be converted to the corresponding intramolecular quaternary salts by a conventional method, for example, by adjustment of pH value, by the treatment of non-ionic adsorption resin such as macroporous non-ionic adsorption resin, or the like.

PROCESS 4

The compound [Ie] and its salt can be prepared by reacting a compound [IV] or its salt with a compound [V] or its salt.

Suitable salts of the compounds [IV] and [V] can be referred to the ones as exemplified for the compounds [I], and further in case that the compound [V] is one of the formula: $R_b^3$—H, wherein $R_b^3$ is as defined above, a metal salt [e.g. silver salt, etc.] thereof can also be used.

The present reaction may be carried out in a solvent such as water, phosphate buffer, acetone, chloroform, acetonitrile, nitrobenzene, methylene chloride, ethylene chloride, formamide, N,N-dimethylformamide, methanol ethanol, diethyl ether, tetrahydrofuran, dimethyl sulfoxide, or any other organic solvent which does not adversely affect the reaction, preferably in ones having strong polarities. Among the solvents, hydrophilic solvents may be used in a mixture with water. The reaction is preferably carried out in around neutral medium. When the compound [IV] is used in a free form, the reaction is preferably conducted in the presence of a base, for example, inorganic base such as alkali metal hydroxide, alkali metal carbonate, alkali metal bicarbonate, organic base such as trialkylamine, and the like. The reaction temperature is not critical, and the reaction is usually carried out at ambient temperature, under warming or under heating. The present reaction is preferably carried out in the presence of alkali metal halide [e.g. sodium iodide, potassium iodide, etc.], alkali metal thiocyanate [e.g. sodium thiocyanate, potassium thiocyanate, etc.] or the like.

PROCESS 5

The compound [I] and its salt can be prepared by reducing a compound [VI] or its salt.

Suitable salts of the compound [VI] can be referred to the ones as exemplified for the compound [I].

The present reduction can be carried out by a conventional method which is applied for the transformation of

into —S—, for example, by using phosphorus trichloride, a combination of stannous chloride and acetyl chloride, a combination of an alkali metal iodide [e.g. sodium iodide, etc.] and trihaloacetic anhydride [e.g. tetrafluoroacetic anhydride, etc.], and the like.

The present reduction is usually carried out in a solvent such as acetone, dioxane, acetonitrile, N,N-dimethylformamide, benzene, hexane, chloroform, methylene chloride, ethylene chloride, tetrahydrofuran, ethyl acetate, or any other solvent which does not adversely affect the reaction.

The reaction temperature is not critical and the reaction is usually carried out under cooling or at ambient temperature.

PROCESS 6

The compound [Ig] and its salt can be prepared by lower alkylating a compound [If] or its salt.

In this reaction, the pyridyl moiety in $R_c^3$ starting compound is converted to 1-lower alkylpyridinio moiety in the object compound [Ig].

Suitable lower alkylating agents may be lower alkyl halide [e.g. methyl iodide, ethyl iodide, propyl iodide, butyl iodide, butyl chloride, pentyl chloride, etc.], lower alkyl sulfonate [e.g. methyl benzenesulfonate, ethyl mesylate, etc.], di(lower)alkyl sulfate [e.g. dimethyl sulfate, diethyl sulfate, etc.] or the like.

This reaction is usually carried out in a conventional solvent such as water, alcohol [e.g. methanol, ethanol, propanol, etc.], tetrahydrofuran, dioxane, ethyl acetate, methylene chloride, N,N-dimethylformamide, dimethyl sulfoxide, diethyl ether or any other organic solvent which does not adversely influence the reaction. And in case that the abovementioned lower alkylating agent is in liquid, it can be also used as a solvent.

The reaction temperature is not critical, and the reaction is usually carried out under cooling, at ambient temperature or under warming or heating.

PROCESS 7

The compound [Ii] and its salt can be prepared by reducing a compound [Ih] or its salt.

The present reduction may include reduction using hydride-transfer reagent, combination of metal and organic acid, catalytic hydrogenation and the like.

In case of using hydride-transfer reagent, suitable hydride-transfer reagent may include alkali metal borohydride [e.g. sodium borohydride, etc.], alkali metal alminum hydride [e.g. lithium alminum hydride, etc.], alkali metal cyanoborohydride [e.g. sodium cyanoborohydride, etc.], alkali metal alkoxyborohydride [e.g. lithium tri-tert-butoxyaluminum hydride, etc.] and the like.

The solvent to be used in this reaction can be selected according to the kind of the hydride-transfer reagent to be used and the reaction can be carried out in the solvent such as water, alcohol [e.g. methanol, ethanol, etc.], ether [e.g. diethyl ether, tetrahydrofuran, 1,2-dimethoxyethane, etc.] or any other solvent which does not adversely affect the reaction.

The reaction temperature is not critical and the reaction is usually carried out under cooling, at ambient temperature or under warming.

In case of using combination of metal and organic acid, suitable metals may be the ones such as iron, zinc or the like and suitable organic acids may be the ones such as formic acid, acetic acid or the like.

In case of using catalytic hydrogenation, suitable catalysts may be the ones such as platinum metal catalysts [e.g. platinum oxide, etc.], palladium metal catalysts [e.g. palladium on carbon, etc.] or the like, and suitable solvents may be the ones, which are commonly used in this reaction, such as alcohol [e.g. methanol, ethanol, etc.], acetic acid, ether [e.g. diethyl ether, dioxane, tetrahydrofuran, 1,2-dimethoxyethane, etc.] cyclohexane, water, ethyl acetate, N,N-dimethylformamide or the like.

PROCESS 8

The compound [Ik] and its salt can be prepared by hydrolizing a compound [Ij] or its salt.

The hydrolysis is preferably carried out in the presence of a base. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base can be also used as the solvent.

The reaction temperature is not critical and the reaction is usually carried out under cooling to warming.

The stating compounds [III] and [VI] are novel and can be prepared by the processes as illustrated in the following.

PREPARATION OF THE STARTING COMPOUND [III]

Process A $$R^1-\underset{\underset{O-CH=CH_2}{\overset{\|}{N}}}{C}-R^8 \quad \xrightarrow[\text{reaction}]{:C{<}^{R^4}_{R^5} \text{ [VIII]} \text{ or Simmos-Smith}} \quad R^1-\underset{\underset{O}{\overset{\|}{N}}}{C}-R^8 \overset{R^4}{\underset{R^5}{\triangleleft}}$$

[VII] or its salt  →  [IX] or its salt

Process B $$R^1-\underset{\underset{O}{\overset{\|}{N}}}{C}-R^8 \overset{R_a^4}{\underset{R_a^5}{\triangleleft}} \quad \xrightarrow{\text{Reduction}} \quad R^1-\underset{\underset{O}{\overset{\|}{N}}}{C}-R^8 \overset{R_b^4}{\underset{R_b^5}{\triangleleft}}$$

[IXa] or its salt  →  [IXb] or its salt

Process C $$X^2-CH_2-CO-\underset{\underset{O}{\overset{\|}{N}}}{C}-R^8 \overset{R^4}{\underset{R^5}{\triangleleft}} \quad \xrightarrow{H_2N-\overset{S}{\overset{\|}{C}}-NH_2}$$

[IXc] or its salt $$H_2N-\underset{S}{\overset{N}{\diagup}}\diagdown\underset{\underset{O}{\overset{\|}{N}}}{C}-R^8 \overset{R^4}{\underset{R^5}{\triangleleft}}$$

[IXd] or its salt

Process D $$H_3C-CO-\underset{\underset{O}{\overset{\|}{N}}}{C}-R_a^8 \overset{R^4}{\underset{R^5}{\triangleleft}} \quad \xrightarrow[\text{Step 1}]{\text{Oxidation}}$$

[IXe]

$$HO_2C-\underset{\underset{O}{\overset{\|}{N}}}{C}-R_a^8 \overset{R^4}{\underset{R^5}{\triangleleft}} \quad \xrightarrow[\text{Step 2}]{\text{Formation of amide}}$$

[X] or its salt $$H_2NCO-\underset{\underset{O}{\overset{\|}{N}}}{C}-R_a^8 \overset{R^4}{\underset{R^5}{\triangleleft}} \quad \xrightarrow[\text{Step 3}]{\text{iminoetherification}}$$

[XI]

$$R^9O-\underset{HN}{\overset{\|}{C}}-\underset{\underset{O}{\overset{\|}{N}}}{C}-R_a^8 \overset{R^4}{\underset{R^5}{\triangleleft}} \quad \xrightarrow[\text{Step 4}]{\text{Amidination}}$$

[XII] or its salt $$\underset{HN}{\overset{H_2N}{\diagdown}}C-\underset{\underset{O}{\overset{\|}{N}}}{C}-R_a^8 \overset{R^4}{\underset{R^5}{\triangleleft}}$$

[XIII] or its salt

Process E $$\underset{HN}{\overset{H_2N}{\diagdown}}C-\underset{\underset{O}{\overset{\|}{N}}}{C}-R_a^8 \overset{R^4}{\underset{R^5}{\triangleleft}} \quad \xrightarrow{\text{(i) Halogenation (ii) MSCN [XIV]}}$$

[XIII] or its salt $$H_2N-\underset{S}{\overset{N}{\diagup}}\underset{N}{\diagdown}C-R_a^8 \overset{R^4}{\underset{R^5}{\triangleleft}}$$

[IXf] or its salt

Process F $$H_2N-\underset{S}{\overset{N}{\diagup}}\diagdown_Q\underset{\underset{O}{\overset{\|}{N}}}{C}-R^8 \overset{R^4}{\underset{R^5}{\triangleleft}} \quad \xrightarrow{\text{Introduction of the amino protective group}}$$

[IXg] or its reactive derivative at the amino group or a salt thereof $$R_a^6-\underset{S}{\overset{N}{\diagup}}\diagdown_Q\underset{\underset{O}{\overset{\|}{N}}}{C}-R^8 \overset{R^4}{\underset{R^5}{\triangleleft}}$$

[IXh] or its salt

Process G $$R_a^6-\underset{S}{\overset{N}{\diagup}}\diagdown_Q\underset{\underset{O}{\overset{\|}{N}}}{C}-R^8 \overset{R^4}{\underset{R^5}{\triangleleft}} \quad \xrightarrow{\text{Elimination of the amino protective group}}$$

[IXh] or its salt

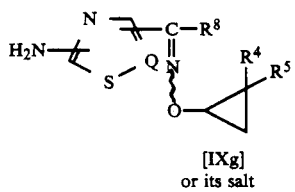

[IXg] or its salt

Process H

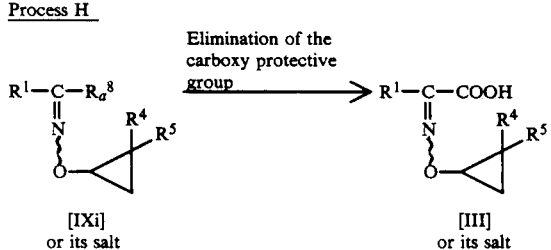

Elimination of the carboxy protective group

[IXi] or its salt → [III] or its salt

PREPARATION OF THE STARTING COMPOUND [VI]

Process I

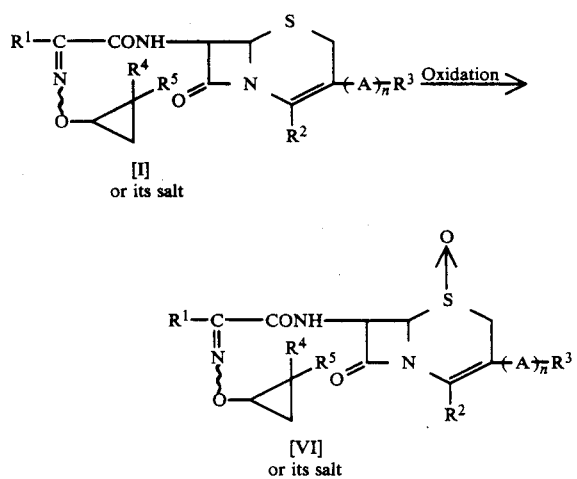

[I] or its salt → [VI] or its salt (Oxidation)

Process J

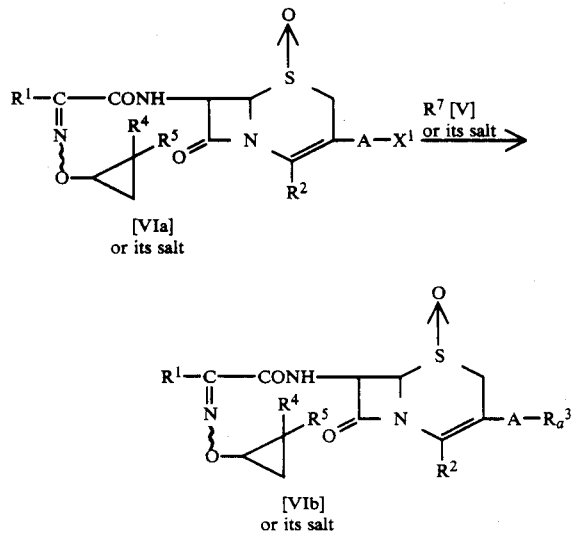

[VIa] or its salt → [VIb] or its salt wherein one of $R_a{}^4$ and $R_a{}^5$ is halogen and the other is hydrogen or halogen, one of $R_b{}^4$ and $R_b{}^5$ is hydrogen and the other is hydrogen or halogen, $R^8$ is carboxy or protected carboxy, $R_a{}^8$ is protected carboxy, $R^9$ is hydrogen or lower alkyl, M is alkali metal, $X^2$ is a leaving group, and $R^1$, $R^2$, $R^3$, $R_a{}^3$, $R^4$, $R^5$, $R_a{}^6$, $R^7$, A, n, Q and Xhu 1 are each as defined above.

Suitable examples of the leaving group for $X^2$ may be halogen [e.g. chloro, bromo, iodo, etc.], sulfonyloxy [e.g. methanesulfonyloxy, benzenesulfonyloxy, toluenesulfonyloxy, etc.] or the like.

The processes for preparing the starting compounds [III] and [VI] are explained in detail in the following.

PROCESS A

The compound [IX] and its salt can be prepared by reacting a compound [VII] or its salt with carbene [VIII] or by subjecting a compound [VII] to Simmons-Smith reaction.

Suitable salts of the compounds [VII] and [IX] can be referred to the acid addition salt as exemplified for the compounds [I].

Carbene [VIII] can be prepared by exposing diazo compound [e.g. diazomethane, chlorodiazomethane, bromodiazomethane, diethyl diazomalonate, etc.] to ultraviolet light; by reacting the above-mentioned diazo compound with catalyst [e.g. cupric acetate, rhodium acetate, etc.]; by pyrolyzing phenyl(trihalomethyl)mercury [e.g. phenyl(tribromomethyl)mercury, phenyl(trichloromethyl)mercury, phenyl(bromodichloromethyl)mercury, etc.], sodium (trihalo)acetate [e.g. sodium chlorodifluoroacetate, sodium trichloroacetate, etc.] or the like; by reacting halogenated methane with a strong base.

Suitable examples of the halogenated methane may be chloroform, bromoform, methylene iodide, methylene chloride, methylene bromide, chloromethyl phenyl sulfide, dichlorofluoromethane, dibromofluoromethane, or the like.

Suitable examples of the strong base may be alkali metal [e.g. lithium, sodium, potassium, etc.], alkali metal hydride [e.g. sodium hydride, etc.], alkaline earth metal hydride [e.g. calcium hydride, etc.], alkali metal hydroxide [e.g. sodium hydroxide, potassium hydroxide, etc.], alkali metal alkoxide [e.g. sodium methoxide, sodium ethoxide, potassium tert-butoxide, etc.], 1,8-diazabicyclo5.4.0]undec-7-ene, or the like.

Simmons-Smith reaction is carried out in the presence of methylene iodide and zinc reagent [e.g. diethylzinc, zinc-copper couple, etc.].

The reaction of this process is usually carried out in a conventional solvent such as, water, acetone, dioxane, acetonitrile, ethylene chloride, tetrahydrofran, N,N-dimethylformamide, diethyl ether or any other organic solvent which does not adversely influence the reaction. These organic solvent may also be used in a mixture with water. The di(or tri)halogenated methane can also be used as the solvent.

The reaction temperature is not critical and the reaction is usually carried out under cooling to heating.

PROCESS B

The compound [IXb] and its salt can be prepared by reducing a compound [IXa] or its salt.

Suitable salts of the compounds [IXa] and [IXb] can be referred to the ones as exemplified for the compounds [I].

The reduction is carried out in the presence of a reducing agent.

Suitable examples of the reducing agent may be a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.]; sodium borohydride; trialkyltin hydride [e.g. trimethyltin hydride, tri-n-butyltin hydride, etc.]; triphenyltin hydride; a combination of liquid ammonia and alkali metal [e.g. lithium, sodium, potassium, etc.]; or the like. When the trialkyltin hydride is used as the reducing agent, the reaction is usually carried out in the presence of a radical initiator such as azobisisobutyronitrile, tertbutyl perbenzoate, dibenzyl peroxide, di-tert-butyl peroxide or the like.

The reaction is usually carried out in a conventional solvent such as water, alcohol [e.g. methanol, ethanol, etc.], dioxane, acetonitrile, tetrahydrofuran, diethyl ether, benzene, N,N-dimethylformamide or any other organic solvent which does not adversely influence the reaction.

The reaction temperature is not critical, and the reaction is usually carried out under cooling to heating.

PROCESS C

The compound [IXd] and its salt can be prepared by reacting a compound [IXc] or its salt with thiourea.

Suitable salts of the compounds [IXc] can be referred to the acid addition salt as exemplified for the compounds [I], and those of the compound [IXd] can be referred to all the salt as exemplified for the same.

This reaction is usually carried out in a conventional solvent such as water, methanol, ethanol, isopropyl alcohol, tetrahydrofuran, dioxane, chloroform, methylene chloride, N,N-dimethylformamide, N,N-dimethylacetamide or any other organic solvent which does not adversely influence the reaction. Among these solvent, hydrophilic solvents may be used in a mixture with water.

The reaction temperature is not critical, and the reaction is usually carried out under cooling to heating.

PROCESS D

Step 1

The compound [X] and its salt can be prepared by oxidizing a compound [IXe].

Suitable salts of the compound [X] can be referred to the base salt as exemplified for the compounds [I].

This oxidation reaction is carried out in the presence of a conventional oxidizing agent which is capable of converting an acetyl group to a carboxy group such as ozone.

In this reaction, enol form of the compound [IXe] can also be used as a starting compound and such enol form of the compound [IXe] can be prepared from the compound [IXe] by a conventional method, for example, reacting the compound [IXe] with silane compound [e.g. tert-butyldimethylchlorosilane, etc.] in the presence of strong base.

This oxidation reaction is usually carried out in a solvent which does not adversely influence the reaction such as methylene chloride, methanol, or the like.

The reaction temperature is not critical and the reaction is usually carried out under cooling to warming.

Step 2

The compound [XI] can be prepared by reacting a compound [X] or its salt with ammonia.

This reaction can be carried out in a similar manner to that of Process 1 mentioned before, and therefore the reaction mode and reaction conditions [e.g. reagent, solvent, reaction temperature, etc.] of this reaction are to be referred to those as explained in Process 1.

Step 3

The compound [XII] and its salt can be prepared by subjecting a compound [XI] to iminoetherification reaction.

Suitable salts of the compound [XII] can be referred to the acid addition salt as exemplified for the compounds [I].

This reaction can be carried out by a conventional method, for example, by using triethyloxonium fluoroborate in a solvent such as methylene chloride, tetrahydrofuran or the like.

The reaction temperature is not critical and the reaction is usually carried out under cooling to warming.

Step 4

The compound [XIII] and its salt can be prepared by reacting a compound [XII] or its salt with ammonia compound [e.g. ammonia, ammonium chloride, etc.].

Suitable salts of the compound [XIII] can be referred to acid addition salt as exemplified for the compound [I].

This reaction is usually carried out in a solvent which does not adversely influence the reaction such as methanol, or the like.

The reaction temperature is not critical and the reaction is usually carried out under cooling to warming.

PROCESS E

The compound [IXf] and its salt can be prepared by reacting the compound [XIII] or its salt with halogenating agent and then the compound [XIV].

In this process, the compound of the following formula are firstly obtained by the reaction of the compound [XIII] or its salt with a halogenating agent.

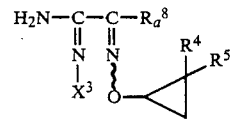

wherein $X^3$ is halogen and $R^4$, $R^5$ and $R_a^8$ are each as defined above.

Suitable halogenating agent to be used in the present reaction may include bromine, chlorine and the like.

Suitable salts of the compound [IXf] can be referred to acid addition salt as exemplified for the compound [I].

Suitable alkali metal for M may include sodium, potassium and the like.

The present reaction is preferably carried out in the presence of a base such as an inorganic base or an organic base, for example, alkali metal carbonate, alkali metal alkoxide, trialkylamine or the like.

The reaction is usually carried out in a solvent such as an alcohol [e.g., methanol, ethanol, etc.] or any other solvent which does not adversely affect the reaction.

The reaction temperature is not critical and the reaction is usually carried out under cooling or at ambient temperature.

PROCESS F

The compound [IXh] and its salt can be prepared by subjecting a compound [IXg] or its reactive derivative at the amino group or a salt thereof to introduction reaction of the amino protective group.

Suitable reactive derivatives at the amino group of the compound [IXg] can be referred to the ones as exemplified for the compound [II].

Suitable salts of the compound [IXg], itsreactive derivative at the amino group and the compound [IXh] can be referred to the ones as exemplified for the compound [I].

The agents used in this reaction may be one which is capable of introducing the amino protective group as exemplified before such as a conventional acylating agent, ar(lower)alkylating agent, or the like.

This reaction can be carried out in a similar manner to that of Process 1 mentioned before, and therefore the reaction mode and reaction conditions [e.g. base, reagent, solvent, reaction temperature, etc.] of this reaction are to be referred to those as explained in Process 1.

PROCESS G

The compound [IXg] and its salt can be prepared by subjecting a compound [IXh] or its salt to elimination reaction of the aminoprotective group.

This reaction can be carried out in a similar manner to that of Process 2 as mentioned before, and therefore the reaction mode and the reaction conditions [e.g. base, acid, catalyst, solvent, reaction temperature, etc.] of this reaction and to be referred to those as explained in Process 2.

PROCESS H

The compound [III] and its salt can be prepared by subjecting a compound [IXi] or its salt to elimination reaction of the carboxy protective group.

Suitable salts of the compound [IXi] can be referred to the acid addition salt as exemplified for the compounds [I].

This reaction can be carried out in a similar manner to that of Process 2 as mentioned before, and therefore the reaction mode and the reaction conditions [e.g. base, acid, catalyst, solvent, reaction temperature, etc.] of this reaction and to be referred to those as explained in Process 2.

PROCESS I

The compound VI] and its salt can be prepared by oxidizing a compound [I] or its salt.

The oxidizing agent used in this reaction is conventional one which is capable of converting a thio group to a sulfinyl group such as m-chloroperbenzoic acid or the like.

This reaction is usually carried out in a conventional solvent which does not adversely influence the reaction such as methlene chloride, or the like, under cooling to heating.

PROCESS J

The compound [VIb] and its salt can be prepared by reacting a compound [VIa] or its salt with a compound [V] or its salt.

Suitable salts of the compounds [VIa] and [VIb] can be referred to the salt as exemplified for the compounds [I].

This reaction can be carried out in a similar manner to that of Process 4 mentioned before, and therefore the reaction mode and the reaction conditions [e.g. reagent, solvent, reaction temperature, base, etc.] of this reaction are to be referred to those as explained in Process 4.

The compounds [I], [Ib], [Id] [Ie], [Ig], [Ii], [Ik], [III], [VI], [VIb], [IX] to [XIII], [IXb], [IXd], [IXf], [IXg] and [IXh] obtained by the processes illustrated before can be isolated and purified by a conventional manner such as pulverization, recrystallization, column chromatography, reprecipitation or the like.

It is to be noted the compounds [I] to [VIII], [Ia] to [Ik], [VIa], [VIb], [IX] to [XIII] and [IXa] to [IXi] may include one or more stereoisomers due to asymmetric carbon atoms and/or carbon and carbon double bond (i.e. Z-isomer and E-isomer), and all of such isomers and a mixture thereof are included within the scope of this invention.

The object compounds [I] and the pharmaceutically acceptable salts thereof are novel and exhibit high antimicrobial activity, inhibiting the growth of a wide variety of pathogenic microorganisms including Gram-positive and Gram-negative microorganisms and are useful as antimicrobial agents.

Now in order to show the utility of the object compounds [I], the test data on MIC (minimal inhibitory concentration) of representative compounds [I] of this invention are shown in the following.

Test method:

In vitro antibacterial activity was determined by the two-fold agar-plate dilution method as described below.

One loopful of an overnight culture of each test strain in Trypticase-soy broth ($10^6$ viable cells per ml) was streaked on heart infusion agar (HI-agar) containing graded concentrations of representative test compound, and the minimal inhibitory concentration (MIC) was expressed in terms of $\mu$g/ml after incubation at 37° C. for 20 hours.

Test Compounds:

(1) 7β-2-8(2-Aminothiazol-4-yl)-2-(cyclopropyloxyimino)acetamido]-3-(1-pyridinio)methyl-3-cephem-4-carboxylate (syn isomer)

(2) 7β-2-8(2-Aminothiazol-4-yl)-2-(cyclopropyloxyimino)acetamido]-3-(1,3,4-thiadiazol-2-yl)thiomethyl-3-cephem-4-carboxylic acid (syn isomer)

(3) 7β-[2-(2-Aminothiazol-4-yl)-2-(cyclopropyloxyimino)acetamido]-3-(5,6-dioxo-4-methyl-14,5,6-tetrahydro-1,2,4-triazin-3-yl)thiomethyl-3-cephem-4-carboxylic acid (syn isomer)

(4) 7β-[2-(2-Aminothiazol-4-yl)-2-(cyclopropyloxyimino)acetamido]-3-(tetrazolo[,15-b]pyridazin-6-yl)-thiomethyl-3-cephem-4-carboxylic acid (syn isomer)

(5) 7β-[2-(2-Aminothiazol-4-yl)-2-(cyclopropyloxyimino)acetamido]-3-(1,2,4-thiadiazol-5-yl)thiomethyl-3-cephem-4-carboxylic acid (syn isomer)

(6) 7β-[2-(2-Aminothiazol-4-yl)-2-(2,2-dichlorocyclopropyloxyimino)acetamido]-3-(1-pyridinio)methyl-3-cephem-4-carboxylate (syn isomer)

(7) 7β-[2-(2-Aminothiazol-4-yl)-2-(2-chlorocyclopropyloxyimino)acetamido]-3-(1,3,4-thiadiazol-2- yl)thiomethyl-3-cephem-4-carboxylic acid (syn isomer, isomer B)
(8) 7β-[2-(2-Aminothiazol-4-yl)-2-(cyclopropyloxyimino)acetamido]-3-(1,2,3-thiadiazol-5-yl)thiomethyl-3-cephem-4-carboxylic acid (syn isomer)
(9) 7β-[2-(2-Aminothiazol-4-yl)-2-(cyclopropyloxyimino)acetamido]cephalosporanic acid (syn isomer)
(10) 7β-[2-(5-Amino-1,2,4-thiadiazol-3-yl)-2-(cyclopropyloxyimino)acetamido]-3-(1-pyridinio)methyl-3-cephem-4-carboxylat (syn isomer)

thoxyimino)-3,3-ethylenedioxybutyrate (syn isomer)(333.3 g) as an oil.

IR (film): 3000, 2900, 1730, 1615, 1375, 1290, 1230, 1215 cm$^{-1}$

NMR (CDCl$_3$, δ): 1.34 (3H, t, J=7 Hz), 1.67 (3H, s), 3.50 (2H, t, J=7 Hz), 4.02 (4H, s), 4.36 (2H, q, J=7 Hz), 4.38 (2H, t, J=7 Hz)

PREPARATION 2

To a solution of ethyl 2-(2-chloroethoxyimino)-3-

Test results:
MIC (μg/ml)

| Test Strain | Test Compound | | | | | | | | | |
|---|---|---|---|---|---|---|---|---|---|---|
| | (1) | (2) | (3) | (4) | (5) | (6) | (7) | (8) | (9) | (10) |
| S. aureus 209P JC-1 | 0.39 | 0.39 | 0.39 | 0.39 | 0.39 | 0.39 | 0.39 | 0.78 | 1.56 | 0.78 |
| E. coli 31 | ≦0.025 | ≦0.025 | ≦0.025 | ≦0.025 | ≦0.025 | 0.05 | ≦0.025 | ≦0.025 | 0.05 | <0.025 |
| E. coli 58 | 0.05 | ≦0.025 | ≦0.025 | 0.05 | ≦0.025 | 0.2 | 0.05 | 0.05 | 0.05 | 0.2 |
| P. mirabilis 1 | 0.1 | 0.05 | 0.05 | 0.1 | 0.05 | 1.56 | 0.2 | 0.1 | 0.05 | 0.2 |
| P. vulgaris IAM 1025 | 0.05 | ≦0.025 | 0.05 | 0.05 | ≦0.025 | 0.05 | ≦0.025 | 0.1 | ≦0.025 | 0.1 |

For therapeutic administration, the object compounds [I] and the pharmaceutically acceptable salt thereof of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound [I] may vary from and also depend upon the age, conditions of the patient, a kind of diseases, a kind of the compound [I] to be applied, etc. In general, amounts between 1 mg and about 4,000 mg or even more per day may be administered to a patient. An average single dose of about 50 mg, 100 mg, 250 mg, 500 mg, 1000 mg, 2000 mg of the object compound [I] of the present invention may be used in treating diseases infected by pathogenic microorganisms.

The following Preparations and Examples are given for the purpose of illustrating the present invention in more detail.

PREPARATION 1

A mixture of ethyl 2-(2-bromoethoxyimino)-3-oxobutyrate (syn isomer)(218.9 g), ethylene glycol (156 ml), and benzene (400 ml) was refluxed in the presence of p-toluenesulfonic acid monohydrate under an azeotropic dehydration condition for 3 days. The mixture was poured into a mixture of ethyl acetate and saturated aqueous solution of sodium bicarbonate under ice-cooling. The organic layer was separated, washed with water, dried over magnesium sulfate and concentrated in vacuo to give a residue. The residue was distilled at 2 mmHg at 144° to 149° C. to give ethyl 2-(2-bromoeoxobutyrate (syn isomer)(10.0 g) and conc. sulfuric acid (0.72 ml) in methanol (20 ml) was dropwise added trimethyl orthoformate (15.9 ml) under reflux during 20 minutes in the presence of Molecular Sieves 4A (Trade Mark, maker: Union Carbide Co.)(3g). The mixture was refluxed for 3 hours. The mixture was poured into a solution of sodium bicarbonate (2.3 g) in ice-water (200 ml) and extracted with diisopropyl ether (200 ml). The extract was washed with water and saturated aqueous solution of sodium chloride successively, dried over magnesium sulfate, and concentrated under reduced pressure to give ethyl 2-(2-chloroethoxyimino-3,3-dimethoxybutyrate (syn isomer)(11.7 g) as an oil.

IR (film): 1740, 1630, 1460, 1370, 1300, 1245, 1195 cm$^{-1}$

NMR (CDCl$_3$, δ): 1.32 (3H, t, J=7 Hz), 1.59 (3H, s), 3.27 (6H, s), 3.66 (2H, t, J=6 Hz), 4.31 (2H, q, J=7 Hz), 4.32 (2H, t, J=6 Hz)

PREPARATION 3

To a solution of ethyl 2-(2-bromoethoxyimino)-3,3-ethylenedioxybutyrate (syn isomer)(50 g) in dimethyl sulfoxide (50 ml) was dropwise added potassium tert-butoxide (21.7 g) in tetrahydrofuran (190 ml) under ice-cooling. The mixture was stirred at the same temperature for 10 minutes. The mixture was poured into ice-water and extracted with diethyl ether. The extract was washed with water, dried over magnesium sulfate and evaporated in vacuo to give ethyl 2-vinyloxyimino-3,3-ethylenedioxybutyrate (syn isomer) (35.1 g) as an oil.

IR (film): 1735, 1620, 1375, 1280, 1230, 1160, 1140, 1065, 1035, 985 cm$^{-1}$

NMR (CDCl$_3$, δ): 1.35 (3H, t, J=7 Hz), 1.69 (3H, s), 4.03 (2H, s), 4.17 (1H, dd, J=2 Hz,7 Hz), 4.36 (2H, q, J=7 Hz), 4.58 (1H, dd, J=2 Hz, 15 Hz), 6.86 (1H, dd, J=7 Hz, 15 Hz)

PREPARATION 4

Ethyl 2-vinyloxyimino-3,3-dimethoxybutyrate (syn isomer) was obtained according to a similar manner to that of Preparation 3.

IR (film): 1730, 1610, 1455, 1365, 1290, 1240, 1160 cm$^{-1}$ 1

NMR (CDCl$_3$, δ): 1.34 (3H, t, J=7 Hz), 1.62 (3H, s), 3.27 (6H, s), 4.17 (1H, dd, J=7 Hz and 2 Hz), 4.34 (2H, q, J=7 Hz), 4.58 (1H, dd, J=14 Hz and 2 Hz), 6.85 (1H, dd, J=14 Hz and 7 Hz)

PREPARATION 5

To a solution of ethyl 2-vinyloxyimino-3,3-ethylenedioxybutyrate (syn isomer)(15 g) and benzyltriethylammonium chloride (164 mg) in a mixture of methylene chloride (13 ml), bromoform (11.4 ml) and ethanol (0.65 ml) was added 50% aqueous solution of sodium hydroxide (105 ml) under ice-cooling. The mixture was stirred for 1 hour at the same temperature and allowed to be stirred at ambient temperature overnight. The mixture was extracted with diethyl ether. The extract was washed with water, dried over magnesium sulfate and concentrated in vacuo. The residue was subjected to column chromatography on silica gel using a mixture of chloroform and ethyl acetate (4:1 V/V) as an eluent to give ethyl 2-(2,2-dibromocyclopropyloxyimino)-3,3-ethylenedioxybutyrate (syn isomer)(15.4 g) as an oil.

NMR (CDCl$_3$, δ) 1.31 (3H, t, J=7 Hz), 1.50-2.12 (2H, m), 1.70 (3H, s), 4.05 (4H, s), 4.25-4.50 (1H, m), 4.30 (2H, q, J=7 Hz)

PREPARATION 6

Ethyl 3,3-dimethoxy-2-(2-phenylthiocyclo propyloxyimino)butyrate (syn isomer) was obtained by using chloromethyl phenyl sulfide instead of bromoform according to a similar manner to that of Preparation 5.

IR (film): 1730, 1580, 1475, 1435, 1365, 1300, 1240, 1185, 1150 cm$^{-1}$

NMR (CDCl$_3$, δ): 0.83-1.63 (2H, m), 1.23 (3H, t, J=7 Hz), 1.46 (3H, s), 2.21-2.46 (1H, m), 3.18 (3H, s), 3.21 (3H, s), 4.16 (2H, q, J=7 Hz), 4.23-4.55 (1H, m), 6.92-7.64 (5H, m).

PREPARATION 7

To a solution of ethyl 2-vinyloxyimino-3,3-ethylenedioxybutyrate (syn isomer)(1.15 g) and benzyltriethylammonium chloride (114 mg) in a mixture of chloroform (2.4 ml) and ethanol (0.05 ml) was added 50% sodium hydroxide (2.4 ml) under ice-cooling. The mixture was stirred at the same temperature for 30 minutes, allowed to be stirred at ambient temperature for 3 hours and finally stirred at 50° C. for an hour. The mixture was poured into ice-water and extracted with diethyl ether. The extract was washed with water, dried over magnesium sulfate and concentrated in vacuo to give ethyl 2-(2,2-dichlorocyclopropyloxyimino)-3,3-ethylenedioxybutyrate (syn isomer)(1.41 g) as an oil.

IR (film): 3000, 2910, 1735, 1375, 1300-1280, 1220, 1165, 1060, 1030 cm$^{-1}$

NMR (CDCl$_3$, δ): 1.30 (3H, t, J=7 Hz), 1.33-1.95 (2H, m), 1.69 (3H, s), 4.04 (4H, s), 4.19 (2H, q, J=7 Hz), 4.20-4.43 (1H, m)

PREPARATION 8

Ethyl 2-(2-chloro-2-fluorocyclopropyloxyimino)-3,3-ethylenedioxybutyrate (syn isomer) was obtained by using dichlorofluoromethane instead of chloroform according to a similar manner to that of Preparation 7.

IR (film): 1735, 1630, 1450, 1380, 1280, 1225, 1170 cm$^{-1}$

NMR (CDCl$_3$, δ): 1.23-2.05 (2H, m), 1.31 (3H, t, J=7 Hz), 1.67 (3H, s), 4.03 (4H, s), 4.15-4.56 (1H, m), 4.28 (2H, q, J=7 Hz)

PREPARATION 9

Ethyl 2-(2-bromo-2-fluorocyclopropyloxyimino)-3,3-ethylenedioxybutyrate (syn isomer) was obtained by using dibromofluoromethane instead of chloroform according to a similar manner to that of Preparation 7.

IR (film): 1735, 1630, 1430, 1380, 1280, 1225, 1165, 1125 cm$^{-1}$

NMR (CDCl$_3$, δ): 1.30 and 1.32 (3H, each t, J=7 Hz), 1.38-2.11 (2H, m), 1.67 and 1.68 (3H, each s), 4.01 and 4.02 (4H, each s), 4.16-4.56 (1H, m), 4.30 (2H, q, J=7 Hz)

PREPARATION 10

To a solution of ethyl 2-(2,2-dibromocyclopropyloxyimino)-3,3-ethylenedioxybutyrate (syn isomer)(16.4 g) in benzene (300 ml) was dropwise added tri-n-butyltin hydride (33 ml). To the mixture was added 2,2'-azobisisobutyronitrile (0.5 g) and the resulting mixture was refluxed for 2 hours under nitrogen atmosphere. The mixture was concentrated in vacuo and the residue was subjected to column chromatography on silica gel using a mixture of chloroform and ethyl acetate (4:1 V/V) as an eluent to give ethyl 2-cyclopropyloxyimino-3,3-ethylenedioxybutyrate (syn isomer)(10.36 g) as an oil.

NMR (CDCl$_3$, δ): 0.50-0.73 (4H, m), 1.30 (3H, t, J=7 Hz), 1.66 (3H, s), 3.90-4.10 (1H, m), 4.00 (4H, s), 4.28 (2H, q, J=7 Hz).

PREPARATION 11

A solution of ethyl 2-(2,2-dichlorocyclopropyloxyimino)-3,3-ethylenedioxybutyrate (syn isomer)(312 mg) and tri-n-butyltinhydride (0.55 ml) in toluene (2 ml) was refluxed under nitrogen atmosphere in the presence of catalytic amount of 2,2'-azobisisobutyronitrile for 2 hours. The reaction mixture was concentrated in vacuo. The residue was subjected to column chromatography on silica gel (24 g) and eluted with a mixture of diethyl ether and n-hexane (1:2 V/V). The fractions containing the compound, which had higher Rf-value on TLC [development solvent system: diethyl ether and n-hexane (2:1 V/V)], were collected and concentrated in vacuo to give ethyl 2-(2-chlorocyclopropyloxyimino)-3,3-ethylenedioxybutyrate (syn isomer)(94 mg).

NMR (CDCl$_3$, δ): 0.90-1.70 (2H, m), 1.31 (3H, t, J=7 Hz), 1.65 (3H, s), 3.18 (1H, ddd, J=8.5 Hz, 6 Hz, 1.5 Hz), 4.01 (4H, s), 4.05-4.30 (1H, m), 4.28 (2H, q, J=7 Hz)

Regarding stereochemical configuration at the cyclopropyl moiety, this type of isomer is hereinafter called "isomer A".

The fractions containing the compound, which had lower Rf-value, were collected and concentrated in vacuo to give ethyl 2-(2-chlorocyclopropyloxyimino)-3,3-ethylenedioxybutyrate (syn isomer)(80 mg).

NMR (CDCl$_3$, δ): 0.90-1.55 (2H, m), 1.32 (3H, t, J=7 Hz), 1.68 (3H, s), 3.05 (1H, dt, J=8 Hz, 6 Hz), 4.00-4.25 (1H, m), 4.03 (4H, s), 4.32 (2H, q, J=7 Hz)

This type of isomer is hereinafter called "isomer B".

PREPARATION 12

A solution of ethyl 2-(2-bromo-2-fluorocyclopropyloxyimino)-3,3-ethylenedioxybutyrate (syn isomer)(4 g) and tri-n-butyltinhydride (2.28 ml) in benzene (30 ml) was refluxed under nitrogen atmosphere in the presence of 2,2'-azobisisobutyronitrile (250 mg) for 2 hours. The reaction mixture was concentrated in vacuo.

The residue was subjected to column chromatography on silica gel and eluted with benzene. The fractions containing the compound, which had higher Rf-value on TLC [development solvent system: benzene], were collected and concentrated in vacuo to give ethyl 2-(2-fluorocyclopropyloxyimino)-3,3-ethylenedioxybutyrate (syn isomer)(1.36 g).

IR (film): 1740, 1630, 1450, 1380, 1300, 1290, 1230, 1155 cm$^{-1}$

NMR (CDCl$_3$, δ): 1.06–1.66 (2H, m), 1.31 (3H, t, J=7 Hz), 1.63 (3H, s), 4.00 (4H, s), 4.10–4.45 (1.5H, m), 4.28 (2H, q, J=7 Hz), 4.90–5.07 (0.5H, m).

Regarding stereochemical configuration at the cyclopropyl moiety, this type of isomer is hereinafter called "isomer A".

The fractions containing the compound, which had lower Rf-value, were collected and concentrated in vacuo to give ethyl 2-(2-fluorocyclopropyloxyimino)-3,3-ethylenedioxybutyrate (syn isomer)(0.83 g).

IR (film): 1730, 1630, 1435, 1370, 1335, 1285, 1205, 1145 cm$^{-1}$

NMR (DMSO-d$_6$, δ): 0.84–1.55 (2H, m), 1.31 (3H, t, J=7 Hz), 1.67 (3H, s), 3.66–4.22 (1.5H, m), 4.02 (4H, s), 4.30 (2H, q, J=7 Hz), 4.73–4.92 (0.5H, m).

This type of isomer is hereinafter called "isomer B".

PREPARATION 13

To a solution of ethyl 2-(2-bromoethoxyimino)-3,3-ethylenedioxybutyrate (syn isomer)(50 g) in N,N-dimethylformamide (100 ml) was portionwise added potassium tert-butoxide (21 g) under −10° C. and the resulted mixture was allowed to be stirred under ice-cooling for 20 minutes. The mixture was poured into ice-water (400 ml) and extracted with methylene chloride (200 ml). The extract was washed with water (200 ml×3) and saturated aqueous solution of sodium chloride (400 ml) successively, dried over magnesium sulfate, and added methylene iodide (16.2 ml). To the solution was dropwise added a 35% (W/W) solution of diethylzinc in cyclohexane (55 ml) under reflux during 40 minutes under nitrogen. atmosphere. After refluxed for 18 hours, the mixture was poured into ice-water (400 ml) and adjusted to pH 40 with 1N hydrochloric acid. The organic layer was separated, washed with an aqueous solution of sodium bicarbonate and a saturated aqueous solution of sodium chloride successively, dried over magnesium sulfate, and concentrated in vacuo. The residue was subjected to column chromatography on silica gel (50 g) using diisopropyl ether as an eluent to give ethyl 2-cyclopropyloxyimino-3,3-ethylenedioxybutyrate (syn isomer)(15 g), the physical data of which were identical to those of the compound prepared in Preparation 10.

PREPARATION 14

To a solution of ethyl 2-cyclopropyloxyimino-3,3-ethylenedioxybutyrate (syn isomer)(487 mg) in methylene chloride (0.8 ml) was added 90% trifluoroacetic acid (0.8 ml) under ice-cooling. The mixture was stirred at ambient temperature for 2 hours. The mixture was concentrated in vacuo to give a residue. The residue was dissolved in diethyl ether and washed successively with saturated aqueous solution of sodium bicarbonate and water, dried over magnesium sulfate and concentrated in vacuo to give ethyl 2-cyclopropyloxyimino-3-oxobutyrate (syn isomer)(382 mg) as an oil.

IR (film): 1725, 1690, 1595, 1440, 1365, 1340, 1305, 1230, 1155, 1060, 1010, 970 cm$^{-1}$ NMR (CDCl$_3$, δ): 0.62–0.95 (4H, m), 1.31 (3H, t, J=7 Hz), 2.32 (3H, s), 3.87–4.30 (1H, m), 4.32 (2H, q, J=7 Hz)

The following compounds (Preparations 15 to 20) were obtained according to a similar manner to that of Preparation 14.

PREPARATION 15

Ethyl 2-(2,2-dichlorocyclopropyloxyimino)-3-oxobutyrate (syn isomer).

IR (film): 1740, 1700, 1610, 1415, 1370, 1310, 1215, 1155, 1055, 1015 cm$^{-1}$

NMR (CDCl$_3$, δ) 1.31 (3H, t, J=7 Hz), 1.46 (3H, s), 1.64–2.07 (2H, m), 4.32–4.57 (1H, m), 4.34 (2H, q, J=7 Hz).

PREPARATION 16

Ethyl 2-(2-chlorocyclopropyloxyimino)-3-oxobutyrate (syn isomer, isomer A).

IR (neat): 3550, 2980, 1785, 1740, 1700, 1605, 1370, 1310, 1230, 1170, 1150 cm$^{-1}$ NMR (CDCl$_3$, δ): 1.15–1.65 (2H, m), 1.31 (3H, t, J=7 Hz), 2.42 (3H, s), 3.28 (1H, ddd, J=8.5 Hz, 6 Hz, 1.5 Hz), 4.15–4.50 (1H, m), 4.32 (2H, q, J=7 Hz).

PREPARATION 17

Ethyl 2-(2-chlorocyclopropyloxyimino)-3-oxobutyrate (syn isomer, isomer B).

IR (neat): 3550, 3000, 1790, 1740, 1700, 1610, 1370, 1310, 1240, 1160 cm$^{-1}$

NMR (CDCl$_3$, δ): 1.10–1.60 (2H, m), 1.33 (3H, t, J=7 Hz), 2.44 (3H, s), 3.12 (1H, dt, J=8 Hz, 6Hz), 4.10–4.50 (1H, m), 4.34 (2H, q, J=7 Hz)

PREPARATION 18

Ethyl 2-(2-phenylthiocyclopropyloxyimino)-3-oxobutyrate (syn isomer).

IR (film): 1740, 1690, 1600, 1580, 1480, 1435, 1370, 1310, 1240, 1200 cm$^{-1}$

NMR (CDCl$_3$, δ): 1.00–1.70 (2H, m), 1.26 (3H, t, J=7 Hz), 2.17 (3H, s), 2.28–2.70 (1H, m), 4.23 (2H, q, J=7 Hz), 4.27–4.67 (1H, m), 7.00–7.50 (5H, m).

PREPARATION 19

Ethyl 2-(2-fluorocyclopropyloxyimino)-3-oxobutyrate (syn isomer, isomer A).

IR (film): 1740, 1700, 1605, 1445, 1370, 1310, 1235, 1145 cm$^{-1}$

NMR (CDCl$_3$, δ): 1.10–1.73 (2H, m), 1.31 (3H, t, J=7 Hz), 2.42 (3H, s), 4.24–4.65 (1.5H, m), 4.32 (2H, q, J=7 Hz), 5.00–5.17 (0.5H, m)

PREPARATION 20

Ethyl 2-(2-fluorocyclopropyloxyimino)-3-oxobutyrate (syn isomer, isomer B)

IR (film): 1735, 1695, 1600, 1430, 1370, 1310, 1240, 1210 cm$^{-1}$

NMR (CDCl$_3$, δ): 0.92–1.68 (2H, m), 1.31 (3H, t, J=7 Hz), 2.42 (3H, s), 3.83–4.52 (1.5H, m), 4.33 (2H, q, J=7 Hz), 4.80–5.00 (0.5H, m)

PREPARATION 21

A solution of ethyl 2-cyclopropyloxyimino-3-oxobutyrate (syn isomer)(358 mg) and pyridinium hydrobromide perbromide (633 mg) in acetic acid (2 ml) was heated at 50° C. for 30 minutes. The mixture was poured into ice-water and extracted with ethyl acetate. The extract was washed successively with saturated aqueous solution of sodium bicarbonate and water, dried over magnesium sulfate and concentrated in vacuo to give ethyl 4-bromo-2-cyclopropyloxyimino-3-oxobutyrate (syn isomer)(470 mg). To a solution of the compound obtained above in N,N-dimethylacetamide (2.2 ml) was added thiourea (126 mg) at ambient temperature. The mixture was stirred at the same temperature for an hour. The mixture was pouredd into ice-water and extracted with ethyl acetate. The extract was washed with water, dried over magnesium sulfate and concentrated in vacuo. The residue was subjected to column chromatography on silica gel using a mixture of chloroform and ethyl acetate (4:1 V/V) as an eluent to give ethyl 2-(2-aminothiazol-4-yl)-2-(cyclopropyloxyimino)acetate (syn isomer)(177 mg) as a crystal.

NMR (CDCl$_3$, $\delta$): 0.57–0.90 (4H, m), 1.36 (3H, t, J=7 Hz), 4.02–4.23 (1H, m), 4.37 (2H, q, J=7 Hz), 5.57 (2H, br s), 6.72 (1H, s).

The following compounds (Preparations 22 to 27) were obtained according to a similar manner to that of Preparation 21.

PREPARATION 22

Ethyl 2-(2-aminothiazol-4-yl)-2-(2,2-dichlorocyclopropyloxyimino)acetate (syn isomer).

NMR (DMSO-d$_6$, $\delta$): 1.25 (3H, t, J=7 Hz), 1.73 (1H, dd, J=6 Hz, 9 Hz), 2.03 (1H, t, J=9 Hz), 4.27 (2H, q, J=7 Hz), 4.50 (1H, dd, J=6 Hz, 9 Hz), 7.00 (1H, s), 7.25 (2H, br s)

PREPARATION 23

Ethyl 2-(2-aminothiazol-4-yl)-2-(2-chlorocyclopropyloxyimino)acetate (syn isomer, isomer A).

IR (Nujol): 3470, 3270, 3120, 1725, 1620, 1545, 1280 cm$^{-1}$

NMR (DMSO-d$_6$, $\delta$): 0.80–1.60 (2H, m), 1.27 (3H, t, J=7 Hz), 3.30 (1H, ddd, J=8 Hz, 6 Hz, 1Hz), 4.00–4.40 (1H, m), 4.28 (2H, q, J=7 Hz), 6.70–7.50 (2H, br ), 6.96 (1H, s).

PREPARATION 24

Ethyl 2-(2-aminothiazol-4-yl)-2-(2-chlorocyclopropyloxyimino)acetate (syn isomer, isomer B).

IR (Nujol): 3450, 3270, 3130, 1725, 1620, 1545, 1260 cm$^{-1}$

NMR (DMSO-d$_6$, $\delta$): 1.10–1.70 (2H, m), 1.28 (3H, t, J=7 Hz), 3.40 (1H, dt, J=8 Hz, 6 Hz), 4.10–4.40 (1H, m), 4.29 (2H, q, J=7 Hz), 6.98 (1H, s), 7.26 (2H, br s).

PREPARATION 25

Ethyl 2-(2-aminothiazol-4-yl)-2-(2-phenylthiocyclopropyloxyimino)acetate (syn isomer)

IR (Nujol): 3430, 3250, 3110, 1715, 1620, 1540, 1455, 1370, 1250 cm$^{-1}$

NMR (CDCl$_3$, $\delta$): 0.90–1.63 (2H, m), 1.27 (3H, t, J=7 Hz), 2.20–2.60 (1H, m), 4.25 (2H, q, J=7 Hz), 4.27–4.60 (1H, m), 5.77 (2H, br s), 6.63 (1H, s), 7.00–7.53 (5H, m).

PREPARATION 26

Ethyl 2-(2-aminothiazol-4-yl)-2-(2-fluorocyclopropyloxyimino)acetate (syn isomer, isomer A).

IR (Nujol): 3460, 3250, 3100, 1720, 1610, 1535, 1300, 1280, 1190 cm$^-$

NMR (DMSO-d$_6$ $\delta$): 0.95–1.70 (2H, m), 1.26 (3H, t, J=7 Hz), 4.20–4.62 (1.5H, m), 4.26 (2H, q, J=7 Hz), 5.10–5.30 (0.5H, m), 6.97 (1H, s), 7.23 (2H, br s).

PREPARATION 27

Ethyl 2-(2-aminot.ihazol-4-yl)-2-(2-fluorocyclopropyloxyimino)acetate (syn isomer, isomer B).

IR (Nujol): 3460, 3270, 3150, 1730, 1620, 1545, 1335, 1270, 1220, 1195 cm$^-$

NMR (DMSO-d$_6$, $\delta$): 0.85–1.55 (2H, m), 1.26 (3H, t, J=7 Hz), 3.77–4.05 (1H, m), 4.25–4.45 (0.5H, m), 4.27 (2H, q, J=7 Hz), 4.92–5.13 (0.5H, m), 6.94 (1H, s), 7.20 (2H, br s).

PREPARATION 28

To a solution of ethyl 2-(2-aminothiazol-4-yl)-2-(cyclopropyloxyimino)acetate (syn isomer)(1.88 g) in 1,4-dioxane (16.7 ml) was added 1N sodium hydroxide (16.7 ml). The mixture was stirred for 1.5 hours at 33° C. After the mixture was cooled under ice-bath, 1N hydrochloric acid (16.7 ml) was added to the mixture. The mixture was concentrated in vacuo to give a residue. The residue was suspended in ethanol, concentrated in vacuo and triturated with ethyl acetate to give crude 2-(2-aminothiazol-4-yl)-2-(cyclopropyloxyimino)acetic acid (syn isomer)(2.63 g). This compound was used for Preparation 33 without further purification.

PREPARATION 29

The following compounds were prepared according to a similar manner to that of Preparation 28.

(a) 2-(2-Aminothiazol-4-yl)-2-(2,2-dichlorocyclopropyloxyimino)acetic acid (syn isomer)

(b) 2-(2-Aminothiazol-4-yl)-2-(2-chlorocyclopropyloxyimino)acetic acid (syn isomer, isomer A)

(c) 2-(2-Aminothiazol-4-yl)-2-(2-chlorocyclopropyloxyimino)acetic acid (syn isomer, isomer B)

(d) 2-(2-Aminothiazol-4-yl)-2-(2-phenylthiocyclopropyoxyimino)acetic acid (syn isomer)

IR (Nujol): 3250, 1640, 1590, 1430, 1380, 1290 cm$^{-1}$

NMR (DMSO-d$_6$, $\delta$): 0.70–1.07 (1H, m), 1.28–1.77 (1H, m), 2.33–2.63 (1H, m), 4.18–4.52 (1H, m), 6.75 (1H, s), 6.88–7.60 (7H, m).

PREPARATION 30

To a suspension of ethyl 2-cyclopropyloxyimino-2-(2-formamidothiazol-4-yl)acetate (syn isomer)(9.92 g) in methanol (99.2 ml) was dropwise added 2N aqueous solution of sodium hydroxide (122 ml) below 10° C. The mixture was stirred under ice-cooling for 4 hours. The mixture was poured into ice-water, washed with ethyl acetat, adjusted to pH 2 with 6N hydrochloric acid under ice-cooling, and extracted with ethyl acetate. The extract was washed with saturated aqueous solution of sodium chloride, dried over magnesium sulfate and concentrated in vacuo. The residue was triturated with petroleum ether to give 2-cyclopropyloxyimino-2-(2-formamidothiazol-4-yl)acetic acid (syn isomer)(6.97 g).

IR (Nujol): 3190, 1700, 1660 cm$^{-1}$

NMR (DMSO-d$_6$, $\delta$) 0.57–0.80 (4H, m), 3.93–4.19 (1H, m), 7.55 (1H, s), 8.50 (1H, s).

PREPARATION 31

2-(2-Fluorocyclopropyloxyimino)-2-(2-formamidothiazol-4-yl)acetic acid (syn isomer, isomer A) was obtained according to a similar manner to that of Preparation 30.

IR (Nujol): 3200, 1690, 1620, 1550, 1290 cm$^{-1}$

NMR (DMSO-d$_6$, $\delta$): 1.00–1.60 (2H, m), 4.20–4.66 (1.5H, m), 5.15–5.35 (0.5H, m), 7.59 (1H, s), 8.49 (1H, s), 12.53 (1H, br s)

PREPARATION 32

2-(2-Fluorocyclopropyloxyimino)-2-(2-formamidothiazol-4-yl)acetic acid (syn isomer, isomer B) was obtained according to a similar manner to that of Preparation 30.

IR (Nujol): 3180, 1690, 1590, 1545, 1280 cm$^{-1}$

NMR (DMSO-d$_6$, δ): 0.96–1.38 (2H, m), 3.80–4.04 (1H, m), 4.23–4.45 (0.5H, m), 4.93–5.15 (0.5H, m), 7.57 (1H, s), 8.50 (1H, s), 12.53 (1H, br s)

PREPARATION 33

To a suspension of crude 2-(2-aminothiazol-4-yl)-2-(cyclopropyloxyimino)acetic acid (syn isomer)(2.63 g) in a mixture of N,N-dimethylformamide (50 ml), tetrahydrofuran (20 ml) and pyridine (2 ml) was added trifluoroacetic anhydride (1.77 ml) under ice-cooling. The mixture was stirred for 30 minutes at the same temperature. The mixture was poured into ice-water, adjusted to pH 2.5 with 1N hydrochloric acid and extracted with ethyl acetate. The extract was washed with water, dried over magnesium sulfate and concentrated in vacuo. The residue was triturated with petroleum ether to give 2-cyclopropyloxyimino-2-(2-trifluoroacetamidothiazol-4-yl)acetic acid (syn isomer)(1.70 g) as a solid.

IR (Nujol): 1730, 1580, 1345, 1290, 1265, 1220, 1210, 1180, 1160, 975 cm$^{-1}$

NMR (CDCl$_3$–DMSO-d$_6$, δ): 0.58–0.9-5 (4H, m), 3.97–4.25 (1H, m), 7.47 (1H, s)

PREPARATION 34

To a solution of crude 2-(2-aminothiazol-4-yl)-2-(2,2-dichlorocyclopropyloxyimino)acetic acid (syn isomer) (2.03 g) in a mixture of tetrahydrofuran (40 ml) and pyridine (1.68 ml) was dropwise added trifluoroacetic anhydride (1.47 ml) at −20° C. The mixture was stirred under ice-cooling for 30 minutes. The mixture was poured into ice-water, adjusted to pH 6.5 with saturated aqueous solution of sodium bicarbonate and washed with ethyl acetate. The aqueous solution was adjusted to pH 2 with 1N hydrochloric acid and extracted with ethyl acetate. The extract was washed with saturated aqueous solution of sodium chloride, dried over magnesium sulfate and concentrated in vacuo to give 2-(2-trifluoroacetamidothiazol-4-yl)-2-(2,2-dichlorocyclopropyloxyimino)acetic acid (syn isomer)(1.88 g) as a solid.

NMR (DMSO-d$_6$, δ): 1.85 (1H, dd, J=6 Hz, 9 Hz), 2.08 (1H, t, J=9 Hz), 4.58 (1H, dd, J=6 Hz, 9 Hz), 7.82 (1H, s)

The following compounds (Preparations 35 to 37) were obtained according to a similar manner to that of Preparation 33.

PREPARATION 35

2-(2-Chlorocyclopropyloxyimino)-2-(2-trifluoroacetamidothiazol-4-yl)acetic acid (syn isomer, isomer A).

IR (Nujol): 1725, 1585, 1350, 1295, 1265, 1215 cm$^{-1}$

NMR (DMSO-d$_6$, δ): 1.00–1.80 (2H, m),3.55 (1H, ddd, J=2 Hz, 6 Hz, 9 Hz), 4.30 (1H, ddd, J=2 Hz, 4 Hz, 6 Hz), 7.77 (1H, s)

PREPARATION 36

2-(2-Chlorocyclopropyloxyimino)-2-(2-trifluoroacetamidothiazol-4-yl)acetic acid (syn isomer, isomer B).

IR (Nujol): 1730, 1580, 1350, 1290, 1260, 1220 cm$^{-1}$

NMR (DMSO-$_6$, δ): 0.90–1.70 (2H, m), 3.35 (1H, dt, J=8 Hz, 6 Hz), 4.00–4.40 (1H, m), 7.77 (1H, s)

PREPARATION 37

2-(2-Phenylthiocyclopropyloxyimino)-2-(2-trifluoroacetamidothiazol-4-yl)acetic acid (syn isomer).

IR (Nujol): 1715, 1580, 1345, 1265, 1210, 1165 cm$^{-1}$

NMR (DMSO-d$_6$, δ): 0.82–1.08 (1H, m), 1.36–1.69 (1H, m), 2.33–2.64 (1H, m), 4.29–4.55 (1H, m), 6.95–7.62 (5H, m), 7.53 (1H, s)

PREPARATION 38

A mixture of formic acid (13.1 ml) and acetic anhydride (32.6 ml) was warmed at 45° C. for 45 minutes. After the mixture was cooled until ambient temperature, ethyl 2-(2-aminothiazol-4-yl)-2-cyclopropyloxyiminoacetate (syn isomer)(22 g) was added thereto. The suspension was turned to a clear solution and soon a precipitate was appeared. To the suspension was added diisopropyl ether (50 ml) and the mixture was stirred at ambient temperature for additional an hour. The mixture was cooled in ice-bath and the precipitate was collected and washed with diisopropyl ether to give ethyl 2-cyclopropyloxyimino-2-(2-formamidothiazol-4-yl)acetate (syn isomer)(20.5 g).

NMR (DMSO-d$_6$, δ): 0.60–0.87 (4H, m), 1.30 (3H, t, J=7 Hz), 3.90–4.30 (1H, m), 4.30 (2H, q, J=7 Hz), 7.63 (1H, s), 8.53 (1H, s).

PREPARATION 39

Ethyl 2-(2-fluorocyclopropyloxyimino)-2-(2-formamidothiazol-4-yl)acetate (syn isomer, isomer A) was obtained according to a similar manner to that of Preparation 38.

IR (Nujol): 3150, 3050, 1725, 1690, 1560, 1270 cm$^{-1}$

NMR (DMSO-d$_6$, δ): 1.23–1.78 (2H, m), 1.27 (3H, t, J=7 Hz), 4.33 (2H, q, J=7 Hz), 4.33–4.70 (1.5H, m), 5.20–5.38 (0.5H, m), 7.67 (1H, s), 8.55 (1H, s).

PREPARATION 40

Ethyl 2-(2-fluorocyclopropyloxyimino)-2-(2-formamidothiazol-4-yl)acetate (syn isomer, isomer B) was obtained according to a similar manner to that of Preparation 38.

IR (Nujol): 3140, 3040, 1715, 1675, 1550, 1270 cm$^{-1}$

NMR (DMSO-d$_6$, δ): 0.87–1.30 (2H, m), 1.27 (3H, t, J=7 Hz), 3.87–4.13 (1H, m), 4.23–4.43 (0.5H, m), 4.33 (2H, q, J=7 Hz), 5.00–5.17 (0.5H, m), 7.65 (1H, s), 8.56 (1H, s)

PREPARATION 41

To a suspension of 2-cyclopropyloxyimino-2-(2-formamidothiazol-4-yl)acetic acid (syn isomer)(761mg) and triethylamine (1.04 ml) in tetrahydrofuran (3.8 ml) was dropwise added trifluoroacetic anhydride (1.05 ml) at −20° C. The mixture was stirred under ice-cooling for an hour. The mixture was poured into ice-water and adjusted to pH 8 with saturated aqueous solution of sodium bicarbonate. The solution was washed with ethyl acetate, adjusted to pH 2 with 6N hydrochloric acid and extracted with ethyl acetate. The extract was washed with saturated aqueous solution of sodium chloride, dried over magnesium sulfate and concentrated in vacuo. The residue was triturated with diisopropyl ether to give 2-cyclopropyloxyimino-2-(2-trifluoroacetamidothiazol-4-yl)acetic acid (syn isomer) (400 mg).

IR (Nujol): 1730, 1580, 1345, 1290, 1265, 1220, 1210, 1180, 1160, 975 cm$^{-1}$

PREPARATION 42

To a solution of diisopropylamine (1.32 ml) in tetrahydrofuran (10 ml) was added dropwise 1.55N n-butyl lithium in n-hexane (4.57 ml) at 0° C. The mixture was stirred at 0° C. for 30 minutes. To the mixture was added dropwise a solution of ethyl 2-cyclopropyloxyimino-3-oxobutyrate (syn isomer)(940 mg) in tetrahydrofuran (1 ml) at −60° C. The mixture was stirred at the same temperature for 30 minutes. To the mixture was added tert-butyldimethylsilyl chloride (1.42 g) at −60° C. and the mixture was gently warmed to ambient temperature. After stirred at ambient temperature for an hour, the mixture was poured into saturated aqueous solution of ammonium chloride and extracted with diethyl ether. The extract was washed successively with cold 1N hydrochloric acid, saturated aqueous solution of sodium bicarbonate, saturated aqueous solution of sodium chloride quickly, dried over magnesium sulfate, and concentrated under reduced pressure to give a residue. The residue was subjected to column chromatography on silica gel (15 g) using a mixture of n-hexane and diisopropyl ether (3:1 V/V) as an eluent to give ethyl 3-tert-butyldimethylsilyloxy-2-cyclopropyloxyimino-3-butenoate (syn isomer)(1.09 g) as an oil.

NMR (CDCl$_3$, δ): 0.09 (3H, s), 0.10 (3H, s), 0.24–0.80 (4H, m), 0.82 and 0.85 (9H, each s), 1.20 (3H, t, J=7 Hz), 3.78–4.05 (1H, m), 4.18 (2H, q, J=7 Hz), 4.55 (2H, s).

PREPARATION 43

Ozone was bubbled into a solution of ethyl 3-tert-butyldimethylsilyloxy-2-cyclopropyloxyimino-3-butenoate (syn isomer) 1.2 g) in a mixture of methylene chloride (24 ml) and methanol (3 ml) at −55° C. until a blue colour appeared. Excess of ozone was removed by bubbling of nitrogen gas and ozonide was decomposed by addition of dimethyl sulfide (2 ml) at −55° C. The mixture was allowed to be warmed at ambient temperature and concentrated in vacuo. The residue was subjected to column chromatography on silica gel (20 g) using a mixture of chloroform and methanol (100:1 V/V) as an eluent to give ethyl hydrogen α-(cyclopropyloxyimino)malonate (syn isomer)(385 mg) as an oil.

IR (film): 1730–1700, 1600, 1440 cm$^{-1}$

NMR (CDCl$_3$, δ): 0.55–0.95 (4H, m), 1.34 (3H, t, J=7 Hz), 4.10–4.35 (1H, m), 4.34 (2H, q, J=7 Hz), 6.97 (1H, br s)

PREPARATION 44

An activated acid, prepared from ethyl hydrogen α-(cyclopropyloxyimino)malonate (syn isomer)(19.78 g), phosphorus oxychloride (11.9 ml) and N,N-dimethylformamide (9.91 ml) by a conventional manner, was added to a saturated ammonia solution in tetrahydrofuran at −30° C. The mixture was gently warmed to ambient temperature. The mixture was poured into a mixture of ethyl acetate (1 l) and ice-water (1 l) and adjusted to pH 7 with saturated aqueous solution of sodium bicarbonate. The organic layer was separated washed with saturated aqueous solution of sodium chloride, dried over magnesium sulfate and concentrated in vacuo. The residue was subjected to column chromatography on silica gel (200 g) using chloroform as an eluent to give ethyl 2-carbamoyl-2-(cyclopropyloxyimino)acetate (syn isomer) as a crystal (10.51 g).

mp: 48°–50° C.

IR (Nujol): 3410, 3300, 3170, 1720, 1680, 1610, 1445, 1410, 1350, 1290, 1210 cm$^{-1}$ NMR (DMSO-d$_6$, δ): 0.60–0.80 (4H, m), 1.21 (3H, t, J=7 Hz), 4.03–4.25 (1H m) 4.22 (2H q, J=7 Hz), 7.70 (2H, br s)

PREPARATION 45

A mixture of ethyl 2-carbamoyl-2-(cyclopropyloxyimino)acetate (syn isomer)(84.1 g) and triethyloxonium fluoroborate (11.5 g) in methylene chloride (110 ml) was stirred at ambient temperature for 16 hours. To the mixture was added triethylamine (17 ml) under ice-cooling. The mixture was washed with water, dried over sodium sulfate, and concentrated in vacuo to give a residue. The residue was dissolved in diisopropyl ether. The solution was washed with water, dried over sodium sulfate, and concentrated in vacuo to give ethyl 3-ethoxy-3-imino-2-(cyclopropyloxyimino)propionate (syn isomer) (9.60 g) as an oil.

IR (neat): 3320, 3000, 1760, 1655, 1605, 1455, 1375, 1335, 1280 cm$^{-1}$

NMR (CDCl$_3$, δ): 0.60–0.90 (4H, m), 1.32 (6H, t, J=7 Hz), 4.00–4.30 (1H, m), 4.27 (2H, q, J=7 Hz), 4.31 (2H, q, J=7 Hz).

PREPARATION 46

A mixture of ethyl 3-ethoxy-3-imino-2-(cyclopropyloxyimino)propionate (syn isomer)(9.6 g) and ammonium chloride (3.27 g) in methanol (70 ml) was stirred at ambient temperature for 3 days. The mixture was concentrated in vacuo and triturated with diethyl ether to give crude ethyl 2-amidino-2(cyclopropyloxyimino)acetate hydrochloride (syn isomer) (9.00 g) as a solid.

IR (Nujol): 1740, 1670 cm$^{-1}$

PREPARATION 47

To a solution of ethyl 2-amidino-2-(cyclopropoxyimino)acetate hydrochloride (syn isomer) (1.44 g) in methanol (11 ml) was added triethylamine (3.06 ml) at −15° C. To the solution was dropwise added bromine (852 mg) at −5° C. After the solution was stirred at −5° C. for 2 minutes, to the solution was added a solution of potassium thiocyanate (518 mg) in methanol (5 ml) at −5° C. The mixture was allowed to be stirred under ice-cooling for 2 hours. The mixture was concentrated in vacuo to give a residue. The residue was dissolved in ethyl acetate. The solution was washed successively with 1N hydrochloric acid, saturated aqueous solution of sodium bicarbonate, and saturated aqueous solution of sodium chloride, dried over magnesium sulfate, concentrated in vacuo, and triturated with diethyl ether to give ethyl 2-(5-amino-1,2,4-thiadiazol3-yl)-2-(cyclopropyloxyimino)acetate (syn isomer)(769 mg) as a crystal.

mp: 154°–155° C.

IR (Nujol): 3440, 1725, 1615, 1530 cm$^{-1}$

NMR (CDCl$_3$, δ): 0.63–0.95 (4H, m), 1.36 (3H, t, J=7 Hz , 4.06–4.35 (1H, m), 4.38 (2H, q, J=7 Hz) 6.22 (2H, brs)

PREPARATION 48

A suspension of ethyl 2-(5-amino-1,2,4-thiadiazol-3-yl)-2-(cyclopropyloxyimino)acetate (syn isomer)(763 mg) in 1N sodium hydroxide (6 ml) was stirred at ambient temperature for 2 hours to give a clear solution. The mixture was adjusted to pH 4.5 with 1N hydrochloric acid and washed with ethyl acetate. The aqueous solution was adjusted to pH 3 with 1N hydrochloric acid and extracted with ethyl acetate. The extract was washed with saturated aqueous sodium chloride, dried over magnesium sulfate, and crystallized from diethyl ether to give 2-(5-amino-1,2,4-thiadiazol-3-yl)-2-cyclopropyloxyiminoacetic acid (syn isomer) (110 mg) as a crystal.

mp: 163° C. (dec.)

IR (Nujol): 3600, 3440, 3350, 3250, 1715, 1610, 1525, 1410, 1345, 1260 cm$^{-1}$ NMR (DMSO-d$_6$, δ): 0.57–0.80 (4H, m), 4.00–4.23 (1H, m), 8.13 (2H, br s).

PREPARATION 49

A mixture of ethyl 2-(5-amino-1,2,4-thiadiazol-3-yl)-2-(cyclopropyloxyimino)acetate (syn isomer)(5.26 g), trityl chloride (12.9 g) and 4-dimethylaminopyridine (224 mg) in pyridine (25 ml) was stirred at 50°–60° C. for 4 hours. The mixture was concentrated in vacuo and the residue was dissolved in ethyl acetate. The organic solution was washed successively with 1N hydrochloric acid, saturated aqueous sodium bicarbonate, and saturated aqueous solution of sodium chloride, dried over magnesium sulfate, and concentrated in vacuo to give a crystal. The crystal was washed with n-hexane and diisopropyl ether, heated in methanol (80 ml) under reflux, and finally cooled to give ethyl 2-cyclopropyloxyimino-2-(5-tritylamino-1,2,4-thiadiazol-3-yl)acetate (syn isomer) (11 g) as a crystal.

IR (Nujol): 1730, 1530, 1405 cm$^{-1}$

NMR (CDCl$_3$, δ): 0.60–1.00 (4H, m), 1.31 (3H, t, J=7 Hz), 4.06–4.30 (1H, m), 4.34 (2H, q, J=7 Hz), 7.10–7.40 (15H, m), 7.50 (1H, br s).

PREPARATION 50

A solution of ethyl 2-cyclopropyloxyimino-2-(5-tritylamino-1,2,4-thiadiazol-3-yl)acetate (syn isomer)(11 g) in a mixture of tetrahydrofuran (72 ml), methanol (72 ml) and 2N sodium hydroxide (72 ml) was stirred at ambient temperature overnight. The mixture was concentrated in vacuo. The residue was dissolved in a mixture of ethyl acetate and water and adjusted to pH 2 with 3N hydrochloric acid. The organic layer was separated, washed with water and saturated aqueous solution of sodium chloride, dried over magnesium sulfate, concentrated in vacuo, and triturated with petroleum ether to give 2-cyclopropyloxyimino-2-(5-tritylamino-1,2,4-thiadiazol-3-yl)acetic acid (syn isomer) (7.75 g) as a solid.

mp:173°–176° C.

IR (Nujol): 1710, 1520 cm$^{-1}$

NMR (DMSO-d$_6$, δ): 0.55–0.95 (4H, m), 4.05–4.33 (1H, m), 7.10–7.40 (15H, m)

PREPARATION 51

To a solution of 2-cyclopropyloxyimino-2-(5-tritylamino-1,2,4-thiadiazol-3-yl)acetic acid (syn isomer)(1 g) in anisole (2 ml) was added trifluoroacetic acid (8 ml) under ice-cooling. After stirring for 2 hours at ambient temperature, the mixture was concentrated in vacuo. The residue was poured into ice-water (50 ml). The mixture was adjusted to pH 7 with saturated aqueous solution of sodium bicarbonate and an insoluble material was filtered off. After washing with a mixture of ethyl acetate and tetrahydrofuran, the filtrate was adjusted to pH 2 with 6N hydrochloric acid and extracted with ethyl acetate. The extract was washed with saturated aqueous sodium chloride, dried over magnesium sulfate, concentrated in vacuo, and triturated with diisopropyl ether to give 2-(5-amino-1,2,4-thiadiazol-3-yl)-2-(cyclopropyloxyimino)acetic acid (syn isomer) as a crystal. The physical data of this compound were identical to those of the compound prepared in Preparation 48.

PREPARATION 52

A mixture of 2-cyclopropyloxyimino-2-(2-formamidothiazol-4-yl) acetic acid (syn isomer) (255 mg) and conc. hydrochloric acid (0.21 ml) in methanol (1.3 ml) was stirred at 30° to 32° C. for 1.5 hours. The mixture was concentrated in vacuo, triturated with diisopropyl ether, diethyl ether and ethyl acetate in turn. The resultant solid was dried over phosphorus pentoxide to give 2-(2-aminothiazol-4-yl)-2-cyclopropyloxyiminoacetic acid hydrochloride (syn isomer) (265 mg).

IR (Nujol):1735–1690, 1620, 1550 cm$^{-1}$

NMR (DMSO-d$_6$, δ): 0.55–0.85 (4H, m), 3.93–4.38 (1H, m), 7.05 (1H, s), 8.24 (3H, br s).

EXAMPLE 1

Phosphorus oxychloride (0.24 ml) was dropwise added to a mixture of N,N-dimethylformamide (0.2 ml) and tetrahydrofuran (0.4 ml) under ice-cooling. After being stirred for 10 minutes at the same temperature, the mixture was cooled until a precipitate appeared. To the suspension was added 2-cyclopropyloxyimino-2-(2-trifluoroacetamidothiazol-4-yl) acetic acid (syn isomer) (647 mg) and additional tetrahydrofuran (4 ml). The mixture was stirred at the same temperature for 30 minutes to give an activated acid solution. On the other hand, a mixture of 7β-amino-3-(1,3,4-thiadiazol-2-yl)thiomethyl-3-cephem-4-carboxylic acid (793 mg) and bis(trimethylsilyl)acetamide (2 ml) in tetrahydrofuran (20 ml) was stirred at 30° C. for 30 minutes to give a clear solution. To the clear solution was added the activated acid solution prepared above at −30° C. The mixture was stirred for 30 minutes at −20° C. to −15° C. The mixture was poured into ice-water, adjusted to pH 7.2 with saturated aqueous solution of sodium bicarbonate, and washed with ethyl acetate. The aqueous solution was adjusted to pH 2.5 with 1N hydrochloric acid and extracted with ethyl acetate. The extract was washed with water, dried over magnesium sulfate and concentrated in vacuo. The residue was triturated with diisopropyl ether to give 7β-[2-cyclopropyloxyimino-2-(2-trifluoroacetamidothiazol-4-yl)acetamido]-3-(1,3,4-thiadiazol-2-yl)thiomethyl-3-cephem-4-carboxylic acid (syn isomer) (1.21 g) as a solid.

IR (Nujol):1780, 1715, 1660, 1580, 1540, 1410 cm$^{-1}$

NMR (DMSO-d$_6$, δ):0.54–0.93 m), 3.56 and 3.83 (2H, ABq, J=18 Hz), 3.96–4.17 (1H, m), 4.25 and 4.59 (2H, ABq, J=14 Hz), 5.16 (1H, d, J=5 Hz), 5.81 (1H, dd, J=5 Hz and 8 Hz), 7.56 (1H, s), 9.53 (1H, s), 9.64 (1H, d, J=8 Hz)

The following compounds (Examples 2 to 20) were obtained according to a similar manner to that of Example 1.

EXAMPLE 2

7β-[2-Cyclopropyloxyimino-2-(2-trifluoroacetamidothiazol-4-yl) acetamido]cephalosporanic acid (syn isomer).

IR (Nujol):1790, 1730, 1660 cm$^{-1}$

EXAMPLE 3

7β-[2-(2,2-Dichlorocyclopropyloxyimino)-2-(2-trifluoroacetamidothiazol-4-yl)acetamido]-3-(1,3,4-thiadiazol-2-yl)thiomethyl-3-cephem-4-carboxylic acid (syn isomer).

IR (Nujol):1770, 1710, 1660 cm$^{-1}$

NMR (DMSO-d$_6$, δ):1.67–2.20 (2H, m), 3.57 and 3.80 (2H, ABq, J=18 Hz), 4.26 and 4.57 (2H, ABq, J=14 Hz), 4.40–4.60 (1H, m), 5.17 (1H, d, J=5 Hz), 5.72–5.92 (1H, m), 7.65 and 7.70 (1H, each s), 9.57 (1H, s), 9.76 and 9.82 (1H, each d, J=8 Hz)

EXAMPLE 4

7β-[2-(2-Chlorocyclopropyloxyimino)-2-(2-trifluoroacetamidothiazol-4-yl)acetamido]-3-(1,3,4-thiadiazol-2-yl)thiomethyl-3-cephem-4-carboxylic acid (syn isomer, isomer A).

IR (Nujol):1780, 1720, 1655, 1260, 1205 cm$^{-1}$

NMR (DMSO-d$_6$, δ):1.00–1.80 (2H, m), 3.40–3.80 (1H, m), 3.58 and 3.85 (2H, ABq, J=18 Hz), 4.00–4.40 (1H, m), 4.26 and 4.61 (2H, ABq, J=14 Hz), 5.16 (1H, d, J=5 Hz), 5.81 (1H, dd, J=5 Hz, 8 Hz), 7.62 and 7.63 (1H, each s), 9.53 (1H, s), 9.66 (1H, d, J=8 Hz)

EXAMPLE 5

7β-[2-(2-Chlorocyclopropyloxyimino)-2-(2-trifluoroacetamidothiazol-4-yl)acetamido]-3-(1,3,4-thiadiazol-2-yl)thiomethyl-3-cephem-4-carboxylic acid (syn isomer, isomer B).

IR (Nujol):1780, 1720, 1670, 1260, 1210 cm$^{-1}$

NMR (DMSO-d$_6$, δ):1.00–1.60 (2H, m), 3.20–3.60 (1H, m), 3.55 and 3.82 (2H, ABq, J=18 Hz), 3.90–4.30 (1H, m), 4.25 and 4.60 (2H, ABq, J=14 Hz), 5.16 (1H, d, J=5 Hz), 5.81 (1H, dd, J=5 Hz, 8 Hz), 7.55 and 7.60 (1H, each s), 9.53 (1H, s), 9.68 (1H, d, J=8 Hz)

EXAMPLE 6

7β-[2-Cyclopropyloxyimino-2-(2-formamidothiazol-4-yl)acetamido]-3-(1,3,4-thiadiazol-2-yl)thiomethyl-3-cephem-4-carboxylic acid (syn isomer).

IR (Nujol):1780, 1655, 1540 cm$^{-1}$

NMR (DMSO-d$_6$, δ):0.47–0.85 (4H, m), 3.49 and 3.75 (2H, ABq, J=18 Hz), 3.85–4.10 (1H, m), 4.16 and 4.52 (2H, ABq, J=14 Hz), 5.07 (1H, d, J=5 Hz), 5.72 (1H, dd, J=5 Hz, 8 Hz), 7.34 (1H, s), 8.42 (1H, s), 9.46 (1H, s), 9.49 (1H, d, J=8 Hz)

EXAMPLE 7

7β-[2-Cyclopropyloxyimino-2-(2-formamidothiazol-4-yl)acetamido]-3-(tetrazolo[1,5-b]pyridazin-6-yl)thiomethyl-3-cephem-4-carboxylic acid (syn isomer).

EXAMPLE 8

7β-[2-Cyclopropyloxyimino-2-(2-formamidothiazol-4-yl) acetamido]-3-(1,2,4-thiadiazol-5-yl)thiomethyl-3-cephem-4-carboxylic acid (syn isomer).

NMR (DMSO-d$_6$, δ):0.50–0.90 (4H, m), 3.51 and 3.87 (2H, ABq, J=18 Hz), 3.90–4.30 (1H, m), 4.27 and 4.65 (2H, ABq, J=14 Hz), 5.27 (1H, d, J=5 Hz), 5.82 (1H, dd, J=5 Hz and 8 Hz), 7.43 (1H, s), 8.50 (1H, s), 8.70 (1H, s), 9.56 (1H, d, J=8 Hz)

EXAMPLE 9

7β-[2-Cyclopropyloxyimino-2-(2-formamidothiazol-4-yl)acetamido]-3-(1,2,3-thiadiazol-5-yl)thiomethyl-3-cephem-4-carboxylic acid (syn isomer).

NMR (DMSO-d$_6$, δ):0.50–0.90 (4H, m), 3.63 (2H, br s), 3.85–4.20 (1H, m), 4.23 (2H, br s), 5.18 (1H, d, J=5 Hz), 5.78 (1H, dd, J=5 Hz and 8 Hz), 7.42 (1H, s), 8.50 (1H, s), 8.85 (1H, s), 9.58 (1H, d, J=8 Hz)

EXAMPLE 10

7β-[2-Cyclopropyloxyimino-2-(2-formamidothiazol-4-yl)acetamido]-3-methylthio-3-cephem-4-carboxylic acid (syn isomer).

NMR (DMSO-d$_6$, δ):0.50–0.90 (4H, m), 2.33 (3H, s), 3.73 (2H, broad s), 3.83–4.23 (1H, m), 5.12 (1H, d, J=5 Hz), 5.68 (1H, dd, J=5 Hz and 8 Hz), 7.43 (1H, s), 8.48 (1H, s), 9.54 (1H, d, J=8 Hz)

EXAMPLE 11

7β-[2-Cyclopropyloxyimino-2-(2-formamidothiazol-4-yl)acetamido]-3-cephem-4-carboxylic acid (syn isomer).

NMR (DMSO-d$_6$, δ):0.50–0.90 (4H, m), 3.57 (2H, m), 3.80–4.27 (1H, m), 5.10 (1H, d, J=5 Hz), 5.82 (1H, dd, J=5 Hz, 8 Hz), 6.37–6.57 (1H, m), 7.40 (1H, s), 8.43 (1H, s), 9.50 (1H, d, J=8 Hz)

EXAMPLE 12

7β-[2-Cyclopropyloxyimino-2-(2-formamidothiazol-4-yl)acetamido]-3-vinyl-3-cephem-4-carboxylic acid (syn isomer).

NMR (DMSO-d$_6$, δ):0.50–0.90 (4H, m), 3.47 and 3.87 (2H, ABq, J=18 Hz), 3.80–4.20 (1H, m), 5.17 (1H, d, J=5 Hz), 5.27 (1H, d, J=12 Hz), 5.53 (1H, d, J=18 Hz), 5.77 (1H, dd, J=5 Hz, 8 Hz), 6.90 (1H, dd, J=12 Hz, 18 Hz), 7.40 (1H, s), 8.47 (1H, s), 9.57 (1H, d, J=8 Hz)

EXAMPLE 13

7β-[2-Cyclopropyloxyimino-2-(2-formamidothiazol-4-yl)acetamido]-3-(1-allyl-1H-tetrazol-5-yl)thiomethyl-3-cephem-4-carboxylic acid (syn isomer).

NMR (DMSO-d$_6$, δ):0.50–0.90 (4H, m), 3.70 (2H, broad s), 3.90–4.17 (1H, m), 4.30 and 4.50 (2H, ABq, J=14 Hz), 4.87–5.47 (5H, m), 5.77–6.37 (2H, m), 7.40 (1H, s), 8.50 (1H, s), 9.57 (1H, d, J=8 Hz)

EXAMPLE 14

7β-[2-Cyclopropyloxyimino-2-(2-formamidothiazol-4-yl)acetamido]-3-(1,2,5-thiadiazol-3-yl) thiomethyl-3-cephem-4-carboxylic acid (syn isomer).

IR (Nujol):1770, 1660, 1540 cm$^{-1}$

NMR (DMSO-d$_6$, δ):0.50–0.90 (4H, m), 3.51 and 3.80 (2H, ABq, J=18 Hz), 3.90–4.20 (1H, m), 4.17 and 4.61 (2H, ABq, J=14 Hz), 5.14 (1H, d, J=8 Hz), 5.78 (1H, dd, J=5 Hz and 8 Hz), 7.42 (1H, s), 8.49 (1H, s), 8.74 (1H, s), 9.56 (1H, d, J=8 Hz)

EXAMPLE 15

7β-[2-(2-Phenylthiocyclopropyloxyimino)-2-(2-trifluoroacetamidothiazol-4-yl)acetamido]-3-(1,3,4-thiadiazol-2-yl)thiomethyl-3-cephem-4-carboxylic acid (syn isomer).

IR (Nujol):1780, 1675, 1580, 1260, 1215, 1165 cm$^{-1}$

NMR (DMSO-d$_6$, δ):0.83–1.20 (1H, m), 1.30–1.73 (1H, m), 2.33–2.66 (1H, m), 3.45–3.80 (2H, m), 4.33 and 4.60 (2H, ABq, J=14 Hz), 4.27–4.57 (1H, m), 5.13 (1H, d, J=5 Hz), 5.77 (1H, dd, J=5 Hz and 8 Hz), 7.00–7.53 (6H, m), 9.53 (1H, s), 9.57 (1H, d, J=8 Hz)

EXAMPLE 16

7β-[2-(2-Fluorocyclopropyloxyimino)-2-(2-formamidothiazol-4-yl)acetamido]-3-(1,3,4-thiadiazol-2-yl)thiomethyl-3-cephem-4-carboxylic acid (syn isomer, isomer A).

IR (Nujol):1765, 1655, 1535 cm$^{-1}$

NMR (DMSO-d$_6$, δ):1.03–1.53 (2H, m), 3.50 and 3.74 (2H, ABq, J=18 Hz), 3.93–4.67 (1.5H, m), 4.18 and 4.53 (2H, ABq, J=14 Hz), 5.02–5.23 (0.5H, m), 5.08 (1H, d, J=5 Hz), 5.72 (1H, dd, J=5 Hz and 8 Hz), 7.40 (1H, s), 8.42 (1H, s), 9.44 (1H, s), 9.48 (1H, d, J=8 Hz)

EXAMPLE 17

7β-[2-Cyclopropyloxyimino-2-(2-formamidothiazol-4-yl)acetamido]-3-(2,2-dibromovinyl)-3-cephem-4-carboxylic acid (syn isomer).

NMR (DMSO-d$_6$, δ):0.50–0.90 (4H, m), 3.63 (2H, br s), 3.93–4.20 (1H, m), 5.21 (1H, d, J=5 Hz), 5.85 (1H, dd, J=5 Hz and 8 Hz), 7.42 (2H, s), 8.50 (1H, s), 9.57 (1H, d, J=8 Hz)

EXAMPLE 18

7β-[2-Cyclopropyloxyimino-2-(2-formamidothiazol-4-yl) acetamido]-3-(3-methyl-1,2,4-thiadiazol-5-yl)-thiomethyl-3-cephem-4-carboxylic acid (syn isomer).

NMR (DMSO-d$_6$, δ):0.53–0.80 (4H, m), 2.55 (3H, s), 3.50 and 3.83 (2H, ABq, J=18 Hz), 3.93–4.17 (1H, m), 4.20 and 4.62 (2H, ABq, J=14 Hz), 5.15 (1H, d, J=5 Hz), 5.80 (1H, dd, J=5 Hz and 8 Hz), 7.42 (1H, s), 8.48 (1H, s), 9.55 (1H, d, J=8 Hz)

EXAMPLE 19

7β-[2-Cyclopropyloxyimino-2-(2-formamidothiazol-4-yl)acetamido]-3-(4-carboxy-3-hydroxyisothiazol-5-yl)thiomethyl-3-cephem-4-carboxylic acid (syn isomer).

IR (Nujol):1770, 1710, 1660, 1525 cm$^{-1}$

NMR (DMSO-d$_6$, δ):0.40–0.90 (4H, m), 3.42 and 3.79 (2H, ABq, J=18 Hz), 3.90–4.20 (1H, m), 4.04 and 4.28 (2H, ABq, J=14 Hz), 5.17 (1H, d, J=5 Hz), 5.78 (1H, dd, J=5 Hz and 8 Hz), 7.41 (1H, s), 8.48 (1H, s), 9.55 (1H, d, J=8 Hz)

EXAMPLE 20

7β-[2-Cyclopropyloxyimino-2-(5-tritylamino-1,2,4-thiadiazol-3-yl)acetamido]-3-(1,3,4-thiadiazol-2-yl)-thiomethyl-3-cephem-4-carboxylic acid (syn isomer).

IR (Nujol-):1770, 1660, 1515 cm$^{-1}$

NMR (DMSO-d$_6$, δ):0.55–0.90 (4H, m), 3.48 and 3.77 (2H, ABq, J=18 Hz), 3.95–4.20 (1H, m), 4.26 and 4.58 (2H, ABq, J=14 Hz), 5.06 (1H, d, J=8 Hz), 5.67 (1H, dd, J=5 Hz and 8 Hz), 7.10–7.50 (15H, m), 9.40 (1H, d, J=8 Hz), 9.52 (1H, s)

EXAMPLE 21

Phosphorus oxychloride (0.64 ml) was added to a solution of N,N-dimethylformamide (0.536 ml) in ethyl acetate (1.3 ml) under ice-cooling and the mixture was stirred at the same temperature for 10 minutes. To the mixture was added tetrahydrofuran (26 ml) and the mixture was stirred under ice-cooling for additional 10 minutes. To the mixture was added 2-cyclopropyloxyimino-2-(2-formamidothiazol-4-yl)acetic acid (syn isomer) (766 mg) and the mixture was stirred for 30 minutes under ice-cooling to give an activated acid solution. On the other hand, benzhydryl 78-amino-3-(5,6-dioxo-4-methyl-1,4,5,6-tetrahydro-1,2,4-triazin-3-yl)thiomethyl-3-cephem-4-carboxylate (1.61 g) was dissolved in a solution of bis(trimethylsilyl)acetamide (4.4 ml) in tetrahydrofuran (30 ml). To the solution was added the activated acid solution obtained above at −30° C. and the mixture was stirred for 30 minutes at −20° C. to −10° C. The mixture was poured into a mixture of ice-water (100 ml) and ethyl acetate (150 ml) and adjusted to pH 7 with saturated aqueous solution of sodium bicarbonate. The organic layer was separated, washed with saturated aqueous solution of sodium chloride, dried over magnesium sulfate and concentrated in vacuo. The residue was triturated with diethyl ether to give benzhydryl 7β-[2-cyclopropyloxyimino-2-(2-formamidothiazol-4-yl)acetamido]-3-(5,6-dioxo-4-methyl-1,4,5,6-tetrahydro-1,2,4-triazin-3-yl) thiomethyl-3-cephem-4-carboxylate (syn isomer) (1.13 g).

IR (Nujol):1775, 1700 cm$^{-1}$

NMR (DMSO-d$_6$, δ):0.52–0.87 (4H, m); 3.19 (3H, s), 3.70 (2H, br s), 3.75–4.25 (3H, m), 5.20 (1H, d, J=5 Hz), 5.90 (1H, dd, J=5 Hz, 8 Hz), 6.92 (1H, s), 7.10–7.70 (11H, m), 8.47 (1H, s), 9.59 (1H, d, J=8 Hz), 12.39 (1H, s)

The following compounds (Examples 22 to 27) were obtained according to a similar manner to that of Example 21.

EXAMPLE 22

Benzhydryl 7β-[2-cyclopropyloxyimino-2-(2-formamidothiazol-4-yl)acetamido]-3-chloromethyl-3-cephem-4-carboxylate (syn isomer).

IR (Nujol): 1780, 1720, 1650, 1540 cm$^{-1}$

NMR (DMSO-d$_6$, δ): 0.50–0.90 (4H, m), 3.67 (2H, broad s), 3.83–4.20 (1H, m), 4.30 (2H, broad s), 5.33 (1H, d, J=5 Hz), 5.90 (1H, dd, J=5 Hz and 8 Hz), 6.93 (1H, s), 7.10–7.67 (11H, m), 8.47 (1H, s), 9.60 (1H, d, J=8 Hz)

EXAMPLE 23

Benzhydryl 7β-[2-cyclopropyloxyimino-2-(2-formamidothiazol-4-yl)acetamido]-3-ethynyl-3-cephem-4-carboxylate (syn isomer).

NMR (DMSO-d$_6$, δ): 0.50–0.90 (4H, m), 3.51 and 3.82 (2H, ABq, J=18 Hz), 3.95–4.20 (1H, m), 4.65 (1H, s), 5.23 (1H, d, J=5 Hz), 5.92 (1H, dd, J=5 Hz and 8 Hz), 6.91 (1H, s), 7.10–7.63 (11 H, m), 8.50 (1H, s), 9.63 (1H, d, J=8 Hz)

EXAMPLE 24

Benzhydryl 7β-[2-cyclopropyloxyimino-2-(2-formamidothiazol-4-yl)acetamido]-3-[(E)-2-(3-pyridylthio)vinyl]-3-cephem-4-carboxylate (syn isomer).

NMR (DMSO-d$_6$, δ): 0.50–0.87 (4H, m), 3.65 and 4.10 (2H, ABq, J=18 Hz), 3.80–4.20 (1H, m), 5.27 (1H, d, J=5 Hz), 5.87 (1H, dd, J=5 Hz and 8 Hz), 6.83 and 7.25 (2H, ABq, J=16 Hz), 6.90 (1H, s), 7.30–7.63 (13H, m), 7.72–8.00 (1H, m), 8.40–8.70 (2H, m), 9.63 (1H, d, J=8 Hz)

EXAMPLE 25

Benzhydryl 7β-[2-cyclopropyloxyimino-2-(2-formamidothiazol-4-yl)acetamido]-3-[(Z)-2-(3-pyridyl)-vinylthio]-3-cephem-4-carboxylate (syn isomer).

IR (Nujol): 1775, 1720, 1685, 1655, 1560, 1540 cm$^{-1}$

NMR (DMSO-d$_6$, δ): 0.55–0.90 (4H, m), 3.78 and 4.11 (2H, ABq, J=18 Hz), 3.92–4.13 (1H, m), 5.27 (1H, d, J=5 Hz), 5.90 (1H, dd, J=5 Hz and 8 Hz), 6.77 (2H, s), 6.91 (1H, s), 7.04–7.56 (13H, m), 7.62–7.83 (1H, m), 8.35–8.62 (2H, m), 9.64 (1H, d, J=8 Hz)

EXAMPLE 26 p-Nitrobenzyl 7β-[2-cyclopropyloxyimino-2-(2-formamidothiazol-4-yl)acetamido]-3-chloro-3-cephem-4-carboxylate (syn isomer).

NMR (DMSO-d$_6$, δ): 0.50–0.90 (4H, m), 3.60 and 4.03 (2H, ABq, J=18 Hz), 3.85–4.10 (1H, m), 5.32 (1H, d, J=5 Hz), 5.45 (2H, s), 5.88 (1H, dd, J=5 Hz and 8 Hz), 7.08 (1H, s), 7.67 and 8.24 (4H, ABq, J=10 Hz), 8.50 (1H, s), 9.69 (1H, d, J=8 Hz)

EXAMPLE 27 p-Nitrobenzyl 7β-[2-cyclopropyloxyimino-2-(2-formamidothiazol-4-yl)acetamido]-3-methoxy-3-cephem-4-carboxylate (syn isomer).

NMR (DMSO-d$_6$, δ): 0.53–0.93 (4H, m), 3.56 (2H, br s), 3.84 (3H, s), 3.90–4.22 (1H, m), 5.21 (1H, d, J=5 Hz), 5.36 (2H, s), 5.67 (1H, dd, J=5 Hz and 8 Hz), 7.46 (1H, s), 7.64 and 8.26 (4H, ABq, J=9 Hz), 8.51 (1H, s), 9.54 (1H, d, J=8 Hz)

EXAMPLE 28

To a solution of 7β-amino-3-(5,6-dioxo-2-methyl-1,2,5,6-tetrahydro-1,2,4-triazin-3-yl)thiomethyl-3-cephem-4-carboxylic acid (966 mg) and sodium bicarbonate (437 mg) in a mixture of tetrahydrofuran (10 ml) and water (10 ml) was dropwise added the activated acid solution, prepared from 2-cyclopropyloxyimino-2-(2-formamidothiazol-4-yl)acetic acid (syn isomer) (500 mg) according to a similar manner to that described in Example 1, with stirring and keeping pH 7.0 to 8.0 with saturated aqueous solution of sodium bicarbonate at 0° to 5° C. The mixture was stirred for 20 minutes at the same temperature. To the mixture was added ethyl acetate (40 ml) and the mixture was adjusted to pH 1.5 with 6N hydrochloric acid. The resulting insoluble material was filtered off. The organic layer was separated from the filtrate, dried over magnesium sulfate and concentrated in vacuo. The residue was triturated with diethyl ether to give 7β-[2-cyclopropyloxyimino-2-(2-formamidothiazol-4-yl)acetamido]-3-(5,6-dioxo-2-methyl-1,2,5,6-tetrahydro-1,2,4-triazin-3-yl)thiomethyl-3-cephem-4-carboxylic acid (syn isomer) (685 mg).

IR (Nujol): 1780, 1665, 1545, 1345 cm$^{-1}$

NMR (DMSO-d$_6$, δ): 0.50–0.90 (4H, m), 3.40–3.90 (2H, m), 3.58 (3H, s), 3.83–4.20 (1H, m), 4.06 and 4.41 (2H, ABq, J=14 Hz), 5.15 (1H, d, J=5 Hz), 5.81 (1H, dd, J=5 Hz, 8 Hz), 7.42 (1H, s), 8.48 (1H, s), 9.55 (1H, d, J=8 Hz), 12.48 (1H, br s)

EXAMPLE 29

7β-[2-Cyclopropyloxyimino-2-(2-formamidothiazol-4-yl)acetamido]-3-(1-methyl-1H-tetrazol-5-yl)thiomethyl-3-cephem-4-carboxylic acid (syn isomer) was obtained according to a similar manner to that of Example 28.

NMR (DMSO-d$_6$, δ): 0.50–0.90 (4H, m), 3.74 (2H, br s), 3.97 (3H, s), 3.93–4.17 (1H, m), 4.34 (2H, br s), 5.17 (1H, d, J=5 Hz), 5.83 (1H, dd, J=5 Hz and 8 Hz), 7.47 (1H, s), 8.55 (1H, s), 9.62 (1H, d, J=8 Hz)

EXAMPLE 30

Vilsmeier reagent was prepared from N,N-dimethylformamide (0.36 ml) and phosphorus oxychloride (0.42 ml) in a usual manner. Vilsmeier reagent was suspended in ethyl acetate (7.5 ml), and 2-cyclopropyloxyimino-2-(2-formamidothiazol-4-yl)acetic acid (syn isomer, 0.98 g) was added thereto under ice-cooling. The mixture was stirred at the same temperature for 30 minutes to produce an activated acid solution. A solution of bis(trifluoroacetio acid) salts of 7β-amino-3-(2-methyl-1-pyrazolio)methyl-3-cephem-4-carboxylate (2 g) and N,O-bis(trimethylsilyl)acetamide (3.79 ml) in tetrahydrofuran (20 ml) was added to the above activated acid solution at −30° C., and the reaction mixture was stirred at −20° to −10° C. for 30 minutes. The mixture was added dropwise to diethyl ether (300 ml), and the precipitates were collected by filtration to give trifluoroacetic acid salt of 7β-[2-cyclopropyloxyimino-2-(2-formamidothiazol-4-yl)acetamido]-3-(2-methyl-1-pyrazolio)methyl-3-cephem-4-carboxylate (syn isomer, 2.41 g).

IR (Nujol): 1780, 1660 cm$^{-1}$

NMR (DMSO-d$_6$, δ): 0.55–0.83 (4H, m), 3.43 (2H, br s), 3.96–4.08 (1H, m), 4.10 (3H, s), 5.23 (1H, d, J=5 Hz), 5.56 (2H, br s), 5.88 (1H, dd, J=8, 5 Hz), 6.92 (1H, t, J=3 Hz), 7.43 (1H, s), 8.48 (1H, d, J=3 Hz), 8.52 (1H, s), 8.61 (1H, d, J=3 Hz), 9.63 (1H, d, J=8 Hz)

EXAMPLE 31

To a suspension of phosphorus pentachloride (240 mg) in methylene chloride (22 ml) was added 2-(5-amino-1,2,4-thiadiazol-3-yl)-2-(cyclopropyloxyimino)acetic acid (syn isomer) (250 mg) at −20° C. The mixture was stirred for 30 minutes at −20° to −10° C. and then for 30 minutes at −10° to 0° C. The mixture was concentrated in vacuo and dissolved in tetrahydrofuran. The solution was dropwise added to a solution of 7β-amino-3-(1,2,3-thiadiazol-5-yl)thiomethyl-3-cephem-4-carboxylic acid in a mixture of water (12 ml) and tetrahydrofuran (5 ml), keeping pH 8 with saturated aqueous solution of sodium bicarbonate, under ice-cooling. After stirring for 30 minutes at the same condition, the mixture was washed with ethyl acetate and adjusted to pH 3 with 1N hydrochloric acid. The mixture was extracted with ethyl acetate. The extract was washed with saturated aqueous solution of sodium chloride, dried over magnesium sulfate, concentrated in vacuo, and triturated with diethyl ether to give 7β-[2-(5-amino-1,2,4-thiadiazol-3-yl)-2-(cyclopropyloxyimino)acetamido]-3-(1,2,3-thiadiazol-5-yl)thiomethyl-3-cephem-4-carboxylic acid (syn isomer) (300 mg) as a solid.

mp: 146° C. (dec.)

IR (Nujol): 1770, 1670, 1620, 1520, 1405, 1260, 1215 cm$^{-1}$

NMR (DMSO-d$_6$, δ): 0.55–0.90 (4H, m), 3.54 and 3.80 (2H, ABq, J=18 Hz), 3.95–4.20 (1H, m), 4.25 (2H, s), 5.18 (1H, d, J=5 Hz), 5.79 (1H, dd, J=5 Hz and 8 Hz), 8.10 (2H, br s), 8.88 (1H, s), 9.52 (1H, d, J=8 Hz)

EXAMPLE 32

To a suspension of 7β-[2-cyclopropyloxyimino-2-(2-trifluoroacetamidothiazol-4-yl)acetamido]-3-(1,3,4-thiadiazol-2-yl)thiomethyl-3-cephem-4-carboxylic acid (syn isomer) (1.1 g) in a mixture of water (23.5 ml) and tetrahydrofuran (2 ml) was added sodium acetate trihydrate (2.35 g) at ambient temperature. The mixture was stirred at the same temperature overnight to give a clear solution. The solution was washed with ethyl acetate and adjusted to pH 2 with 1N hydrochloric acid. The mixture was extracted with tetrahydrofuran twice. The extract was washed with saturated aqueous solution of sodium chloride, dried over magnesium sulfate and concentrated in vacuo. The residue was triturated with ethyl acetate to give 7β-[2-(2-aminothiazol-4-yl)-2-(cyclopropyloxyimino)acetamido]-3-(1,3,4-thiadiazol-2-yl)thiomethyl-3-cephem-4-carboxylic acid (syn isomer) (780 mg) as a solid.

mp: 135° C. (dec.)

IR (Nujol): 1770, 1660 cm$^{-1}$

NMR (DMSO-d$_6$, δ): 0.52–0.85 (4H, m), 3.56 and 3.82 (2H, ABq, J=18 Hz), 3.90–4.20 (1H, m), 4.25 and 4.60 (2H, ABq, J=14 Hz), 5.14 (1H, d, J=5 Hz), 5.76 (1H, dd, J=5 Hz, 8 Hz), 6.83 (1H, s), 9.55 (1H, s), and 9.57 (1H, d, J=8 Hz)

The following compounds (Examples 33 to 36) were obtained according to a similar manner to that of Example 32.

EXAMPLE 33

7β-[2-(2-Aminothiazol-4-yl)-2-(cyclopropyloxyimino)acetamido]cephalosporanic acid (syn isomer).

mp: 139° C. (dec.)

IR (Nujol): 1770, 1720, 1650, 1540 cm$^{-1}$

NMR (DMSO-d$_6$, δ): 0.53–0.74 (4H, m), 2.04 (3H, s), 3.42 and 3.67 (2H, ABq, J=18 Hz), 3.87–4.12 (1H, m), 4.66 and 4.98 (2H, ABq, J=14 Hz), 5.13 (1H, d, J=5 Hz), 5.77 (1H, dd, J=5 Hz, 8 Hz), 6.78 (1H, s), 9.50 (1H, d, J=8 Hz)

EXAMPLE 34

7β-[2-(2-Aminothiazol-4-yl)-2-(2,2-dichlorocyclopropyloxyimino)acetamido]-3-(1,3,4-thiadiazol-2-yl)thiomethyl-3-cephem-4-carboxylic acid (syn isomer).

mp: 163° C. (dec.)

IR (Nujol): 1770, 1670 cm$^{-1}$

NMR (DMSO-d$_6$, δ): 1.67–2.17 (2H, m), 3.53 and 3.80 (2H, ABq, J=18 Hz), 4.25 and 4.62 (2H, ABq, J=14 Hz), 4.34–4.60 (1H, m), 5.17 (1H, d, J=5 Hz), 5.67–5.87 (1H, m), 6.85 and 6.90 (1H, each s), 7.26 (2H, br s), 9.53–9.70 (1H, m), 9.55 (1H, s)

EXAMPLE 35

7β-[2-(2-Aminothiazol-4-yl)-2-(2-chlorocyclopropyloxyimino)acetamido]-3-(1,3,4-thiadiazol-2-yl)thiomethyl-3-cephem-4-carboxylic acid (syn isomer, isomer B).

mp: 161° C. (dec.)

IR (Nujol): 1770, 1660, 1620, 1520 cm$^{-1}$

NMR (DMSO-d$_6$, δ): 0.90–1.50 (2H, m), 3.10–3.40 (1H, m), 3.54 and 3.80 (2H, ABq, J=18 Hz), 3.90–4.20 (1H, m), 4.24 and 4.58 (2H, ABq, J=14 Hz), 5.13 (1H, d, J=5 Hz), 5.75 (1H, dd, J=5 Hz, 8 Hz), 6.76 and 6.79 (1H, each s), 9.43 (1H, s), 9.49 (1H, d, J=8 Hz)

EXAMPLE 36

7β-[2-(2-Aminothiazol-4-yl)-2-(2-phenylthiocyclopropyloxyimino)acetamido]-3-(1,3,4-thiadiazol-2-yl)thiomethyl-3-cephem-4-carboxylic acid (syn isomer)

mp: 130° C. (dec.)

IR (Nujol): 1770, 1665, 1520 cm$^{-1}$

NMR (DMSO-d$_6$, δ): 0.82–1.08 (1H, m), 1.33–1.66 (1H, m), 2.20–2.55 (1H, m), 3.63 (2H, br s), 4.05–4.40 (1H, m), 4.22 and 4.58 (2H, ABq, J=14 Hz), 5.09 (1H, d, J=5 Hz), 5.68 (1H, dd, J=5 Hz and 8 Hz), 6.66 and 6.69 (1H, each s), 6.95–7.60 (7H, m), 9.38 (1H, d, J=8 Hz), 9.51 (1H, s)

EXAMPLE 37

A mixture of 7β-[2-cyclopropyloxyimino-2-(2-formamidothiazol-4-yl)acetamido]-3-(1,3,4-thiadiazol-2-yl)thiomethyl-3-cephem-4-carboxylic acid (syn isomer) (1.1 g) and concentrated hydrochloric acid (0.404 ml) in methanol (10.5 ml) was warmed at 33°–35° C. for 1.5 hours. The mixture was poured into ice-water, adjusted to pH 7.5 with saturated aqueous solution of sodium bicarbonate and washed with ethyl acetate. The aqueous solution was adjusted to pH 2 with 1N hydrochloric acid and extracted with a mixture of ethyl acetate and tetrahydrofuran. The extract was washed with saturated aqueous solution of sodium chloride, dried over magnesium sulfate and concentrated in vacuo. The residue was triturated with ethyl acetate to give 7β-[2-(2-aminothiazol-4-yl)-2-(cyclopropyloxyimino)acetamido]-3-(1,3,4-thiadiazol-2-yl)thiomethyl-3-cephem-4-carboxylic acid (syn isomer) (786 mg).

mp: 135° C. (dec.)

IR (Nujol): 1770, 1660 cm$^{-1}$

The following compounds (Examples 38 to 54) were obtained according to a similar manner to that of Example 37.

EXAMPLE 38

7β-[2-(2-Aminothiazol-4-yl)-2-(cyclopropyloxyimino)acetamido]-3-(tetrazolo[1,5-b]pyridazin-6-yl)thiomethyl-3-cephem-4-carboxylic acid (syn isomer)

mp: 170° C. (dec.)

IR (Nujol): 1765, 1665, 1515 cm$^{-1}$

NMR (DMSO-d$_6$, δ): 0.50–0.83 (4H, m), 3.58 and 3.85 (2H, ABq, J=18 Hz), 3.87–4.10 (1H, m), 4.16 and 4.62 (2H, ABq, J=14 Hz), 5.12 (1H, d, J=5 Hz), 5.76 (1H, dd, J=5 Hz, 8 Hz), 6.72 (1H, s), 7.15 (2H, br s), 7.72 (1H, d, J=10 Hz), 8.56 (1H, d, J=10 Hz), 9.45 (1H, d, J=8 Hz)

EXAMPLE 39

7β-[2-(2-Aminothiazol-4-yl)-2-(cyclopropyloxyimino)acetamido]-3-(1,2,4-thiadiazol-5-yl)thiomethyl-3-cephem-4-carboxylic acid (syn isomer).

mp: 156° C. (dec.) IR (Nujol): 1770, 1670, 1620, 1530 cm$^{-1}$

NMR (DMSO-d$_6$, δ): 0.50–0.80 (4H, m), 3.51 and 3.78 (2H, ABq, J=18 Hz), 3.83–4.10 (1H, m), 4.26 and 4.60 (2H, ABq, J=14 Hz), 5.12 (1H, d, J=5 Hz), 5.73 (1H, dd, J=5 Hz, 8 Hz), 6.72 (1H, s), 7.14 (2H, br s), 8.67 (1H, s), 9.44 (1H, d, J=8 Hz)

EXAMPLE 40

7β-[2-(2-Aminothiazol-4-yl)-2-(cyclopropyloxyimino)acetamido]-3-(1,2,3-thiadiazol-5-yl)thiomethyl-3-cephem-4-carboxylic acid (syn isomer).

mp: 145° C. (dec.)

IR (Nujol): 1770, 1665 cm$^{-1}$

NMR (DMSO-d$_6$, δ): 0.45–0.90 (4H, m), 3.52 and 3.77 (2H, ABq, J=18 Hz), 3.82–4.12 (1H, m), 4.25 (2H, br s), 5.17 (1H, d, J=5 Hz), 5.75 (1H, dd, J=5 Hz, 8 Hz), 6.75 (1H, s), 7.17 (2H, br s), 8.86 (1H, s), 9.48 (1H, d, J=8 Hz)

EXAMPLE 41

7β-[2-(2-Aminothiazol-4-yl)-2-(cyclopropyloxyimino)acetamido] -3-(5,6-dioxo-2-methyl-1,2,5,6-tetrahydro-1,2,4-triazin-3-yl)thiomethyl-3-cephem-4-carboxylic acid (syn isomer).

mp: 175° C. (dec.)

IR (Nujol): 1770, 1630, 1410, 1345 cm$^{-1}$

NMR (DMSO-d$_6$, δ): 0.50–0.90 (4H, m), 3.40–3.80 (2H, m), 3.59 (3H, s), 3.80–4.10 (1H, m), 4.07 and 4.40 (2H, ABq, J=14 Hz), 5.12 (1H, d, J=5 Hz), 5.76 (1H, dd, J=5 Hz, 8 Hz), 6.74 (1H, s), 7.16 (2H, br s), 9.45 (1H, d, J=8 Hz)

EXAMPLE 42

7β-[2-(2-Aminothiazol-4-yl)-2-(cyclopropyloxyimino)acetamido]-3-methylthio-3-cephem-4-carboxylic acid (syn isomer).

mp: 155° C. (dec.)

IR (Nujol): 1765, 1670, 1530 cm$^{-1}$

NMR (DMSO-d$_6$, δ): 0.51–0.92 (4H, m), 2.33 (3H, s), 2.76 (2H, broad s), 3.82–4.18 (1H, m), 5.12 (1H, d, J=5

Hz), 5.66 (1H, dd, J=5 Hz, 8 Hz), 6.77 (1H, s), 7.16 (2H, broad s), 9.45 (1H, d, J=8 Hz)

EXAMPLE 43

7β-[2-(2-Aminothiazol-4-yl)-2-(cyclopropyloxyimino)acetamido]-3-cephem-4-carboxylic acid (syn isomer).
mp: 164° C. (dec.)
IR (Nujol): 1765, 1660, 1620, 1520 cm$^{-1}$
NMR (DMSO-d$_6$, δ): 0.43–0.86 (4H, m), 3.60 (2H, broad s), 3.81–4.20 (1H, m), 5.08 (1H, d, J=5 Hz), 5.78 (1H, dd, J=5 Hz, 8 Hz), 6.45 (1H, m), 6.73 (1H, s), 7.17 (2H, broad s), 9.48 (1H, d, J=8 Hz)

EXAMPLE 44

7β-[2-(2-Aminothiazol-4-yl)-2-(cyclopropyloxyimino)acetamido]-3-vinyl-3-cephem-4-carboxylic acid (syn isomer).
mp: 155° C. (dec.)
IR (Nujol): 1770, 1660, 1520 cm$^{-1}$
NMR (DMSO-d$_6$, δ): 0.50–0.93 (4H, m), 3.52 and 3.88 (2H, ABq, J=18 Hz), 3.80–4.15 (1H, m), 5.17 (1H, d, J=5 Hz), 5.30 (1H, d, J=12 Hz), 5.57 (1H, d, J=16 Hz), 5.76 (1H, dd, J=5 Hz, 8 Hz), 6.76 (1H, s), 6.90 (1H, dd, J=12 Hz, 16 Hz), 7.16 (2H, broad s), 9.49 (1H, d, J=8 Hz)

EXAMPLE 45

7β-[2-(2-Aminothiazol-4-yl)-2-(cyclopropyloxyimino)acetamido]-3-(1-allyl-1H-tetrazol-5-yl)thiomethyl-3-cephem-4-carboxylic acid (syn isomer).
mp: 136° C. (dec.)
IR (Nujol): 1770, 1665, 1530 cm$^{-1}$
NMR (DMSO-d$_6$, δ): 0.50–0.90 (4H, m), 3.52 and 3.78 (2H, ABq, J=18 Hz), 3.82–4.10 (1H, m), 4.18 and 4.46 (2H, ABq, J=14 Hz), 4.82–5.37 (5H, m), 5.60–6.20 (2H, m), 6.73 (1H, s), 7.16 (2H, broad s), 9.46 (1H, d, J=8 Hz)

EXAMPLE 46

7β-[2-(2-Aminothiazol-4-yl)-2-(cyclopropyloxyimino)acetamido]-3-(1,2,5-thiadiazol-3-yl)thiomethyl-3-cephem-4-carboxylic acid (syn isomer).
mp: 164° C. (dec.)
IR (Nujol): 1775, 1670, 1630, 1535 cm$^{-1}$
NMR (DMSO-d$_6$, δ): 0.45–0.90 (4H, m), 3.50 and 3.78 (2H, ABq, J=18 Hz), 3.80–4.20 (1H, m), 4.15 and 4.59 (2H, ABq, J=14 Hz), 5.12 (1H, d, J=5 Hz), 5.72 (1H, dd, J=5 Hz and 8 Hz), 6.74 (1H, s), 6.80–7.70 (2H, broad), 8.73 (1H, s), 9.46 (1H, d, J=8 Hz)

EXAMPLE 47

7β-[2-(2-Aminothiazol-4-yl)-2-(2-fluorocyclopropyloxyimino)acetamido]-3-(1,3,4-thiadiazol-2-yl)thiomethyl-3-cephem-4-carboxylic acid (syn isomer, isomer A).
mp: 152° C. (dec.)
IR (Nujol): 1775, 1665, 1530 cm$^{-1}$
NMR (DMSO-d$_6$, δ): 1.00–1.53 (2H, m), 3.56 and 3.82 (2H, ABq, J=18 Hz), 3.95–4.65 (1.5H, m), 4.23 and 4.59 (2H, ABq, J=14 Hz), 5.05–5.40 (0.5H, m), 5.12 (1H, d, J=5 Hz), 5.73 (1H, dd, J=5 Hz and 8 Hz), 6.78 (1H, s), 7.18 (2H, br s), 9.47 (1H, d, J=8 Hz), 9.51 (1H, s)

EXAMPLE 48

7β-[2-(2-Aminothiazol-4-yl)-2-(cyclopropyloxyimino)acetamido]-3-(1-methyl-1H-tetrazol-5-yl)thiomethyl-3-cephem-4-carboxylic acid (syn isomer).
mp: 150° C. (dec.)
IR (Nujol): 1770, 1660, 1515 cm$^{-1}$
NMR (DMSO-d$_6$, δ): 0.50–0.90 (4H, m), 3.66 (2H, br s), 3.85–4.10 (1H, m), 3.91 (3H, s), 4.18 and 4.39 (2H, ABq, J=14 Hz), 5.12 (1H, d, J=5 Hz), 5.75 (1H, dd, J=5 Hz and 8 Hz), 6.73 (1H, s), 7.15 (2H, br s), 9.45 (1H, d, J=8 Hz)

EXAMPLE 49

7β-[2-(2-Aminothiazol-4-yl)-2-(cyclopropyloxyimino)acetamido]-3-(2,2-dibromovinyl)-3-cephem-4-carboxylic acid (syn isomer).
mp: 135° C. (dec.)
IR (Nujol): 1770, 1660, 1520 cm$^{-1}$
NMR (DMSO-d$_6$, δ): 0.48–0.93 (4H, m), 3.74 (2H, br s), 3.85–4.05 (1H, m), 5.16 (1H, d, J=5 Hz), 5.78 (1H, dd, J=5 Hz and 8 Hz), 6.73 (1H, s), 6.90–7.36 (2H, br), 7.40 (1H, s), 9.48 (1H, d, J=8 Hz)

EXAMPLE 50

7β-[2-(2-Aminothiazol-4-yl)-2-(cyclopropyloxyimino)acetamido]-3-chloro-3-cephem-4-carboxylic acid (syn isomer)
mp: 135° C. (dec.)
IR (Nujol): 1770, 1660, 1520 cm$^{-1}$
NMR (DMSO-d$_6$, δ): 0.50–0.90 (4H, m), 3.63 and 3.98 (2H, ABq, J=18 Hz), 3.87–4.05 (1H, m), 5.22 (1H, d, J=5 Hz), 5.78 (1H, dd, J=5 Hz and 8 Hz), 6.73 (1H, s), 7.16 (2H, br s), 9.51 (1H, d, J=8 Hz)

EXAMPLE 51

7β-[2-(2-Aminothiazol-4-yl)-2-cyclopropyloxyimino)acetamido]-3-methoxy-3-cephem-4-carboxylic acid (syn isomer).
mp: 150° C. (dec.)
IR (Nujol): 1755, 1655, 1520 cm$^{-1}$
NMR (D$_2$O, δ): 0.62–0.92 (4H, m), 3.39 and 3.72 (2H, ABq, J=18 Hz), 3.73 (3H, s), 4.02–4.30 (1H, m), 5.18 (1H, d, J=5 Hz), 5.60 (1H, d, J=5 Hz), 7.07 (1H, s)

EXAMPLE 52

7β-[2-(2-Aminothiazol-4-yl)-2-(cyclopropyloxyimino)acetamido]-3-(3-methyl-1,2,4-thiadiazol-5-yl)thiomethyl-3-cephem-4-carboxylic acid (syn isomer).
mp: 150° C. (dec.)
IR (Nujol): 1770, 1660, 1515 cm$^{-1}$
NMR (DMSO-d$_6$, δ): 0.50–0.87 (4H, m), 2.50 (3H, hidden), 3.50 and 3.77 (2H, ABq, J=18 Hz), 3.83–4.10 (1H, m), 4.22 and 4.62 (2H, ABq, J=14 Hz), 5.12 (1H, d, J=5 Hz), 5.72 (1H, dd, J=5 Hz and 8 Hz), 6.72 (1H, s), 6.83–7.57 (2H, br), 9.42 (1H, d, J=8 Hz)

EXAMPLE 53

7β-[2-(2-Aminothiazol-4-yl)-2-(cyclopropyloxyimino)acetamido]-3-(4-carboxy-3-hydroxyisothiazol-5-yl)thiomethyl-3-cephem-4-carboxylic acid (syn isomer).
mp: 149° C. (dec.)
IR (Nujol): 1760, 1650 cm$^{-1}$
NMR (DMSO-d$_6$, δ): 0.50–0.90 (4H, m), 3.52 and 3.77 (2H, ABq, J=18 Hz), 3.85–4.10 (1H, m), 4.05 and 4.27 (2H, ABq, J=14 Hz), 5.15 (1H, d, J=5 Hz), 5.75 (1H, dd, J=5 Hz and 8 Hz), 6.73 (1H, s), 9.45 (1H, d, J=8 Hz)

EXAMPLE 54

7β-[2-(2-Aminothiazol-4-yl)-2-(cyclopropyloxyimino)acetamido]-3-[(Z)-2-(1-methyl-3-pyridinio)-vinylthiomethyl]-3-cephem-4-carboxylate (syn isomer).
mp: 160° C. (dec.)
IR (Nujol): 1750, 1655, 1590, 1520, 1345 cm$^{-1}$ NMR (DMSO-d$_6$, δ): 0.43–0.87 (4H, m), 3.18–3.76 (2H, hidden), 3.81–4.08 (1H, m), 4.19 and 4.52 (2H, ABq, J=14 Hz), 4.38 (3H, s), 5.01 (1H, d, J=5 Hz), 5.56 (1H, dd, J=5 Hz and 8 Hz), 6.58 (1H, d, J=12 Hz), 6.72 (1H, s), 7.19 (2H, br s), 7.95–8.28 (1H, m), 7.98 (1H, d, J=12 Hz), 8.42–8.63 (1H, m), 8.64–8.85 (1H, m), 9.10–9.27 (1H, m), 9.40 (1H, d, J=8 Hz)

EXAMPLE 55

To a suspension of benzhydryl 7β-[2-cyclopropyloxyimino-2-(2-formamidothiazol-4-yl)acetamido]-3-(5,6-dioxo-4-methyl-1,4,5,6-tetrahydro-1,2,4-triazin-3-yl)thiomethyl-3-cephem-4-carboxylate (syn isomer) (1.10 g) in a mixture of methanol (7.5 ml) and tetrahydrofuran (4 ml) was added concentrated hydrochloric acid (0.44 ml) and the mixture was stirred at 35° C. for an hour. The mixture was poured into a mixture of ethyl acetate (100 ml) and ice-water (100 ml) and adjusted to pH 7 with saturated aqueous solution of sodium bicarbonate. The organic layer was separated, washed with saturated aqueous solution of sodium chloride and water successively and concentrated in vacuo. The residue was subjected to column chromatography on silica gel (30 g) using a mixture of chloroform and methanol (30:1 V/V) as an eluent to give benzhydryl 7β-[2-(2-aminothiazol-4-yl)-2-(cyclopropyloxyimino)acetamido]-3-(5,6-dioxo-4-methyl-1,4,5,6-tetrahydro-1,2,4-triazin-3-yl)thiomethyl-3-cephem-4-carboxylate (syn isomer) (356 mg).

IR (Nujol): 1780, 1710, 1590, 1520 cm$^{-1}$

NMR (DMSO-d$_6$, δ): 0.50–0.90 (4H, m), 3.20 (3H, s), 3.71 (2H, br s), 3.80–4.30 (3H, m), 5.18 (1H, d, J=5 Hz), 5.87 (1H, dd, J=5 Hz, 8 Hz), 6.76 (1H, s), 6.93 (1H, s), 7.10–7.70 (10H, m), 9.50 (1H, d, J=8 Hz), 12.34 (1H, s)

EXAMPLE 56

Benzhydryl 7β-[2-(2-aminothiazol-4-yl)-2-(cyclopropyloxyimino)acetamido]-3-[(Z)-2-(3-pyridyl)vinylthio]-3-cephem-4-carboxylate (syn isomer) was obtained according to a similar manner to that of Example 55.

IR (Nujol): 1770, 1720, 1665, 1605, 1525 cm$^{-1}$

NMR (DMSO-d$_6$, δ): 0.55–0.92 (4H, m), 3.78 and 4.12 (2H, ABq, J=18 Hz), 3.85–4.15 (1H, m), 5.26 (1H, d, J=5 Hz), 5.87 (1H, dd, J=5 Hz and 8 Hz), 6.78 (3H, s), 6.92 (1H, s), 7.03–7.59 (13H, m), 7.62–7.85 (1H, m), 8.35–8.64 (2H, m), 9.54 (1H, d, J=8 Hz)

EXAMPLE 57

Benzhydryl 7β-[2-(2-aminothiazol-4-yl)-2-(cyclopropyloxyimino)acetamido]-3-ethynyl-3-cephem-4-carboxylate (syn isomer) was obtained according to a similar manner to that of Example 55.

NMR (DMSO-d$_6$, δ): 0.47–0.90 (4H, m), 3.53 and 3.88 (2H, ABq, J=18 Hz), 3.83–4.15 (1H, m), 4.65 (1H, s), 5.25 (1H, d, J=5 Hz), 5.91 (1H, dd, J=5 Hz and 8 Hz), 6.78 (1H, s), 6.94 (1H, s), 7.00–7.70 (12H, m), 9.57 (1H, d, J=8 Hz)

EXAMPLE 58

To a solution of trifluoroacetic acid salt of 7β-[2-cyclopropyloxyimino-2-(2-formamidothiazol-4-yl)acetamido]-3-(2-methyl-1-pyrazolio)methyl-3-cephem-4-carboxylate (syn isomer, 2.35 g) in methanol (12 ml) was added conc. hydrochloric acid (0.8 ml) at ambient temperature, and the mixture was stirred at the same temperature for 2 hours. The reaction mixture was added to diethyl ether (300 ml), and the precipitates were collected by filtration. The precipitates were dissolved in water (20 ml) and the solution was adjusted to pH 5 with saturated aqueous solution of sodium bicarbonate. The solution was subjected to column chromatography on macroporous non-ionic adsorption resin "Diaion HP-20" (Trademark, manufactured by Mitsubishi Chemical Industries) and eluted with 15% aqueous solution of isopropyl alcohol. The fractions containing the object compound were collected and evaporated in vacuo to remove isopropyl alcohol. The solution was lyophilized to give 7β-[2-(2-aminothiazol-4-yl)-2-(cyclopropyloxyimino)acetamido]-3-(2-methyl-1-pyrazolio)methyl-3-cephem-4-carboxylate (syn isomer, 0.68 g).

IR (Nujol): 1770, 1670, 1610 cm$^{-1}$

NMR (D$_2$O, δ): 0.63–0.97 (4H, m), 3.22 and 3.53 (2H, ABq, J=17 Hz), 4.09–4.18 (1H, m), 4.13 (3H, s), 5.26 (1H, d, J=5 Hz), 5.28 and 5.55 (2H, ABq, J=16 Hz), 5.84 (1H, d, J=5 Hz), 6.81 (1H, t, J=3 Hz), 7.03 (1H, s), 8.22 (1H, d, J=3 Hz), 8.24 (1H, d, J=3 Hz)

EXAMPLE 59

To a solution of 7β-[2-(cyclopropyloxyimino)-2-(5-tritylamino-1,2,4-thiadiazol-3-yl)acetamido]-3-(1,3,4-thiadiazol-2-yl)thiomethyl-3-cephem-4-carboxylic acid (syn isomer) (1.1 g) in formic acid (11 ml) was added concentrated hydrochloric acid (0.29 ml) under ice-cooling. The mixture was stirred for 3.5 hours at the same temperature. The mixture was concentrated in vacuo and poured into a mixture of ethyl acetate and water. After the mixture was adjusted to pH 7.2 with saturated aqueous solution of sodium bicarbonate, the aqueous layer was separated, adjusted to pH 3 with 1N hydrochloric acid, and extracted with ethyl acetate. The extract was washed with saturated aqueous solution of sodium chloride, dried over magnesium sulfate, concentrated in vacuo, and triturated with diethyl ether to give 7β-[2-(5-amino-1,2,4-thiadiazol-3-yl)-2-(cyclopropyloxyimino)acetamido]-3-(1,3,4-thiadiazol-2-yl)thiomethyl-3-cephem-4-carboxylic acid (syn isomer) (459 mg) as a solid.

mp: 156° C. (dec.)

IR (Nujol): 1770, 1665, 1610, 1520 cm$^{-1}$

NMR (DMSO-d$_6$, δ): 0.50–0.88 (4H, m), 3.57 and 3.80 (2H, ABq, J=18 Hz), 3.96–4.15 (1H, m), 4.24 and 4.61 (2H, ABq, J=14 Hz), 5.14 (1H, d, J=5 Hz), 5.78 (1H, dd, J=5 Hz and 8 Hz), 8.12 (2H, br s), 9.50 (1H, d, J=8 Hz), 9.57 (1H, s)

EXAMPLE 60

The activated solution of 2-cyclopropyloxyimino-2-(2-trifluoroacetamidothiazol-4-yl)acetic acid (syn isomer) (824 mg) was prepared according to a similar manner described in Example 1. On the other hand, to a suspension of 1-[(7β-amino-4-carboxy-3-cephem-3-yl)methyl]pyridinium chloride hydrochloride (1.24 g) in tetrahydrofuran (30 ml) was added a mixture of N-trimethylsilylacetamide (1.61 g) and bis(trimethylsilyl)acetamide (3 ml). The suspension was stirred for an hour at 30° C. to give a clear solution. To the clear solution was added the activated acid solution at −30° C. The mixture was stirred for 30 minutes at −20° C. to −15° C. The mixture was poured into water (20 ml), adjusted to pH 5 with saturated aqueous solution of sodium bicarbonate and washed with ethyl acetate. The aqueous solution was adjusted to pH 6 with saturated aqueous solution of sodium bicarbonate. To the solution was added sodium acetate trihydrate (7.94 g) and the solution was stirred at ambient temperature overnight.

To the solution was added additional sodium acetate trihydrate (7.94 g) and the solution was warmed at 37° C. for 5 hours. The aqueous solution was adjusted to pH 3 with 1N hydrochloric acid, washed with ethyl acetate and subjected to a column chromatography on a non-ionic adsorption resin "Diaion HP-20" (25 ml). After the column was washed with water, the elution was carried out with 3% isopropyl alcohol and 5% isopropyl alcohol successively. The fractions containing the object compound were collected, combined, evaporated to remove isopropyl alcohol under reduced pressure, and lyophilized to give 7β-[2-(2-aminothiazol-4-yl)-2-(cyclopropyloxyimino)acetamido]-3-(1-pyridinio)methyl-3-cephem-4-carboxylate (syn isomer) (420 mg) as a solid.

mp: 150° C. (dec.)

IR (Nujol): 1760, 1660, 1520 cm$^{-1}$

NMR (D$_2$O-DSS, δ): 1.57–1.88 (4H, m), 3.17 and 3.65 (2H, ABq, J=18 Hz), 4.03–4.24 (1H, m), 5.24 (1H, d, J=5 Hz), 5.32 and 5.57 (2H, ABq, J=14 Hz), 5.82 (1H, d, J=5 Hz), 7.00 (1H, s), 8.08 (2H, t, J=7 Hz), 8.57 (1H, t, J=7 Hz), 8.92 (2H, d, J=7 Hz)

EXAMPLE 61

7β-[2-(2-Aminothiazol-4-yl)-2-(2-phenylthiocyclopropyloxyimino)acetamido]-3-(1-pyridinio)methyl-3-cephem-4-carboxylate (syn isomer) was obtained according to a similar manner to that of Example 60.

mp: 165° C. (dec.)

IR (Nujol): 1770, 1665, 1605, 1520, 1350 cm$^{-1}$

NMR (D$_2$O, δ): 0.74–1.10 (1H, m), 1.30–1.65 (1H, m), 2.24–2.45 (1H, m), 2.80–3.45 (2H, m), 4.10–4.43 (1H, m), 5.04 (1H, d, J=5 Hz), 5.15 and 5.67 (2H, ABq, J=14 Hz), 5.60 (1H, dd, J=5 Hz and 8 Hz), 6.60 and 6.64 (1H, each s), 6.93–7.45 (5H, m), 7.97–8.27 (2H, m), 8.42–8.69 (1H, m), 9.20–9.55 (2H, m)

EXAMPLE 62

Phosphorus oxychloride (0.31 ml) was added to a mixture of N,N-dimethylformamide (0.246 ml) and tetrahydrofuran (0.5 ml) under ice-cooling. The mixture was stirred at the same temperature for 10 minutes and the mixture was cooled until a precipitate appeared. To the suspension was added 2-(2,2-dichlorocyclopropyloxyimino)-2-(2-trifluoroacetamidothiazol-4-yl)acetic acid (syn isomer) (1 g) and tetrahydrofuran (5 ml) and the mixture was stirred under ice-cooling for 30 minutes to give an activated acid solution. On the other hand, to a suspension of 1-[7β-amino-4-carboxy-3-cephem-3-yl)methyl]pyridinium chloride hydrochloride (1.24 g) in tetrahydrofuran (30 ml) was added a mixture of N-trimethylsilylacetamide (1.61 g) and bis(trimethylsilyl)acetamide (3 ml). The suspension was stirred at 30° C. for an hour to give a clear solution. To the solution was added the activated acid solution prepared above at −30° C. and the mixture was stirred at −20° C. to 15° C. for 30 minutes. The mixture was poured into ice-water and adjusted to pH 3.5 with 1N hydrochloric acid. The solution was extracted with tetrahydrofuran. The extract was dried over magnesium sulfate and concentrated in vacuo to give a residue. The residue was dissolved in aqueous solution of sodium acetate trihydrate (3.47 g, 35 ml) and the solution was stirred at ambient temperature for 3 days. An insoluble material was filtered off and the filtrate was adjusted to pH 4 with 1N hydrochloric acid. The solution was subjected to column chromatography on a non-ionic adsorption resin "Diaion HP-20" (20 ml). After the column was washed successively with water, 3%, 5% and 10% isopropyl alcohol, the elution was carried out with 15%, 20% and 30% isopropyl alcohol successively. The fractions containing the object compound were collected, combined evaporated to remove isopropyl alcohol under reduced pressure and finally lyophylized to give 7β-[2-(2-aminothiazol-4-yl)-2-(2,2-dichlorocyclopropyloxyimino)acetamido]-3-(1-pyridinio)methyl-3-cephem-4-carboxylate (syn isomer) (280 mg) as a powder.

IR (Nujol): 1760, 1620–1600 cm$^{-1}$

NMR (DMSO-d$_6$, δ): 1.60–2.17 (2H, m), 3.05 and 3.53 (2H, ABq, J=18 Hz), 4.20–4.55 (1H, m), 5.13 and 5.70 (2H, ABq, J=14 Hz), 5.05 (1H, d, J=5 Hz), 5.55–5.83 (1H, m), 6.70 and 6.83 (1H, each s), 7.23 (2H, br s), 8.02–8.30 (2H, m), 8.45–8.77 (1H, m), 9.03–9.73 (3H, m)

EXAMPLE 63

1-[(7β-Amino-4-carboxy-3-cephem-3-yl)methyl]pyridinium chloride hydrochloride (960 mg) was dissolved in a solution of N-trimethylsilylacetamide (1.5 g) and bis(trimethylsilyl)acetamide (2.8 ml) in tetrahydrofuran (10 ml). To this solution was added the activated acid solution, which was prepared from 2-cyclopropyloxyimino-2-(2-formamidothiazol-4-yl)acetic acid (syn isomer) (500 mg) according to a similar manner to that described in Example 1, at −20° C. The mixture was stirred at −20° C. to −10° C. for 40 minutes. The mixture was poured into ethyl acetate (250 ml). The precipitate was collected and suspended in methanol (20 ml). To the suspension was added concentrated hydrochloric acid (0.62 ml) and the mixture was warmed at 30° to 35° C. for 2 hours. The mixture was poured into ice-water (50 ml), adjusted to pH 2.5 with saturated aqueous solution of sodium bicarbonate, and washed with ethyl acetate. The aqueous solution was subjected to column chromatography on a non-ionic adsorption resin "Diaion HP-20" (30 ml). After the column was washed with water (300 ml), 1% isopropyl alcohol (60 ml), and 3% isopropyl alcohol (60 ml) successively, the elution was carried out with 5% isopropyl alcohol (250 ml) and 10% isopropyl alcohol (150 ml) successively. The fractions containing the object compound were collected, combined, concentrated in vacuo to about 100 ml and lyophilized to give 7β-2-(2-aminothiazol-4-yl)-2-(cyclopropyloxyimino)acetamido]-3-(1-pyridinio)methyl-3-cephem-4-carboxylate (syn isomer) (553 mg).

mp: 150° C. (dec.)

IR (Nujol): 1760, 1600, 1520 cm$^{-1}$

The following compounds (Examples 64 to 69) were obtained according to a similar manner to that of Example 63.

EXAMPLE 64

7β-[2-(2-Aminothiazol-4-yl)-2-(cyclopropyloxyimino)acetamido]-3-(3-methyl-1-pyridinio)methyl-3-cephem-4-carboxylate (syn isomer). mp: 160° C. (dec.)

IR (Nujol): 3450–3150, 1770, 1670–1600, 1530, 1450 cm$^{-1}$

NMR (D$_2$O, δ): 0.50–0.90 (4H, m), 2.54 (3H, s), 3.17 and 3.63 (2H, ABq, J=18 Hz), 4.00–4.30 (1H, m), 5.24 (1H, d, J=5 Hz), 5.29 and 5.53 (2H, ABq, J=14 Hz), 5.82 (1H, d, J=5 Hz), 6.98 (1H, s), 7.80–8.07 (1H, m), 8.25–8.48 (1H, m), 8.65–8.84 (2H, m)

EXAMPLE 65

7β-[2-(2-Aminothiazol-4-yl)-2-(cyclopropyloxyimino)acetamido]-3-[6,7-dihydro-5H-1-(1-pyrindinio)]methyl-3-cephem-4-carboxylate (syn isomer).

mp: 165° C. (dec.)

IR (Nujol): 3450–3100, 1770, 1660, 1610, 1530, 1445, 1280, 1210 cm$^{-1}$

NMR (D$_2$O, δ): 0.60–0.95 (4H, m), 2.10–2.50 (2H, m), 2.90–3.60 (6H, m), 4.00–4.30 (1H, m), 5.21 (1H, d, J=5 Hz), 5.26 and 5.51 (2H, ABq, J=14 Hz), 5.82 (1H, d, J=5 Hz), 6.97 (1H, s), 7.60–7.88 (1H, m), 8.13–8.46 (1H, m), 8.40–8.60 (1H, m)

EXAMPLE 66

7β-[2-(2-Aminothiazol-4-yl)-2-(cyclopropyloxyimino)acetamido]-3-[(E)-2-(1-methyl-3-pyridinio)thiovinyl]-3-cephem-4-carboxylate (syn isomer).

mp: 135° C. (dec.)

IR (Nujol): 1755, 1650, 1590, 1520 cm$^{-1}$

NMR (DMSO-d$_6$, δ): 0.50–0.97 (4H, m), 3.50 and 3.69 (2H, ABq, J=18 Hz), 3.82–4.13 (1H, m), 4.33 (3H, s), 5.04 (1H, d, J=5 Hz), 5.59 (1H, dd, J=5 Hz and 8 Hz), 6.48 (1H, d, J=16 Hz), 6.73 (1H, s), 7.19 (2H, br s), 7.41 (1H, d, J=16 Hz), 7.83–8.06 (1H, m), 8.33–8.53 (1H, m), 8.66–8.83 (1H, m), 8.90–9.02 (1H, m), 9.46 (1H, d, J=8 Hz)

EXAMPLE 67

7β-[2-(2-Aminothiazol-4-yl)-2-(2-fluorocyclopropyloxyimino)acetamido]-3-(1-pyridinio)methyl-3-cephem-4-carboxylate (syn isomer, isomer A).

mp: 95° C. (dec.)

IR (Nujol): 1775, 1660, 1630, 1610, 1530 cm$^{-1}$

NMR (D$_2$O-NaHCO$_3$, δ): 1.13–1.75 (2H, m), 3.18 and 3.66 (2H, ABq, J=18 Hz), 4.20–4.60 (1.5H, m), 5.13–5.30 (0.5H, m), 5.25 (1H, d, J=5 Hz), 5.33 and 5.57 (2H, ABq, J=14 Hz), 5.81 (1H, d, J=5 Hz), 7.00 (1H, s), 7.93–8.20 (2H, m), 8.42–8.68 (1H, m), 8.82–9.00 (2H, m)

EXAMPLE 68

7β-[2-(2-Aminothiazol-4-yl)-2-(2-fluorocyclopropyloxyimino)acetamido]-3-(1-pyridinio)methyl-3-cephem-4-carboxylate (syn isomer, isomer B).

mp: 95° C. (dec.)

IR (Nujol): 1775, 1660, 1630, 1610, 1530 cm$^{-1}$

NMR (D$_2$O-NaHCO$_3$, δ): 0.98–1.63 (2H, m), 3.15 and 3.64 (2H, ABq, J=18 Hz), 3.89–4.15 (1H, m), 4.20–4.40 (0.5H, m), 4.88–5.13 (0.5H. m), 5.26 (1H, d, J=5 Hz), 5.32 and 5.56 (2H, ABq, J=14 Hz), 5.82 (1H, d, J=5 Hz), 6.99 (1H, s), 7.92–8.16 (2H, m), 8.40–8.66 (1H, m), 8.80–9.00 (2H, m)

EXAMPLE 69

7β-[2-(2-Aminothiazol-4-yl)-2-(cyclopropyloxyimino)acetamido]-3-(2,3-dimethyl-1-pyridinio)methyl-3-cephem-4-carboxylate (syn isomer).

mp: 140° C. (dec.)

IR (Nujol): 1760, 1650, 1600, 1520 cm$^{-1}$

NMR (D$_2$O, δ): 0.60–0.93 (4H, m), 2.46 (3H, s), 2.71 (3H, s), 3.11 and 3.46 (2H, ABq, J=18 Hz), 4.00–4.25 (1H, m), 5.18 (1H, d, J=5 Hz), 5.28 and 5.62 (2H, ABq, J=14 Hz), 5.80 (1H, d, J=5 Hz), 6.92 (1H, s), 7.16–7.81 (1H, m), 8.06–8.28 (1H, m), 8.42–8.62 (1H, m)

EXAMPLE 70

A mixture of syn isomer and anti isomer of 7β-[2-(2-aminothiazol-4-yl)-2-(cyclopropyloxyimino)acetamido]-3-(Z)-2-(1-methyl-3-pyridinio)vinylthio]-3-cephem-4-carboxylate were obtained from the syn isomer of the corresponding 2-formamidothiazolyl compound according to a similar manner to that of Example 63.

Syn Isomer:

mp: 160° C. (dec.)

IR (Nujol): 1760, 1650, 1600, 1520, 1340 cm$^{-1}$

NMR (DMSO-d$_6$, δ): 0.45–0.90 (4H, m), 3.13 and 3.64 (2H, ABq, J=18 Hz), 3.82–4.16 (1H, m), 4.38 (3H, s), 5.03 (1H, d, J=5 Hz), 5.57 (1H, dd, J=5 Hz and 8 Hz), 6.64 and 6.98 (2H, ABq, J=12 Hz), 6.74 (1H, s), 7.22 (2H, br s), 7.85–8.18 (1H, m), 8.34–8.58 (1H, m), 8.62–8.82 (1H, m), 9.16–9.30 (1H, m), 9.38 (1H, d, J=8 Hz)

Anti Isomer:

mp: 160° C. (dec.)

IR (Nujol): 1760, 1665, 1605, 1520, 1340 cm$^{-1}$

NMR (DMSO-d$_6$, δ): 0.45–0.90 (4H, m), 3.12 and 3.65 (2H, ABq, J=18 Hz), 3.95–4.21 (1H, m), 4.38 (3H, s), 5.01 (1H, d, J=5 Hz), 5.55 (1H, dd, J=5 Hz and 8 Hz), 6.66 and 6.98 (2H, ABq, J=12 Hz), 7.06 (2H, br s), 7.38 (1H, s), 7.86–8.14 (1H, m), 8.35–8.56 (1H, m), 8.60–8.80 (1H, m), 9.10–9.35 (2H, m)

EXAMPLE 71

Phosphorus oxychloride (0.53 ml) was dropwise added to N,N-dimethylformamide (0.42 ml) under ice-cooling. After stirring for 10 minutes at the same temperature, the mixture was cooled until a precipitate appeared. To the suspension was added 2-cyclopropyloxyimino-2-(2-formamidothiazol-4-yl)acetic acid (syn isomer) (1.12 g). The mixture was stirred at the same temperature for 30 minutes to give an activated acid solution. On the other hand, a mixture of 7β-amino-3-carbamoyloxymethyl-3-cephem-4-carboxylic acid (1.5 g), N-trimethylsilylacetamide (1.4 g) and bis(trimethylsilyl)acetamide (2.2 g) in tetrahydrofuran (26 ml) was stirred at 30° C. for 30 minutes to give a clear solution. To the clear solution was added the activated acid solution prepared above at −30° C. The mixture was stirred for 30 minutes at −20° C. to −15° C. The mixture was poured into ice-water, adjusted to pH 7.2 with saturated aqueous solution of sodium bicarbonate, and washed with ethyl acetate. The aqueous solution was adjusted to pH 2.5 with 1N hydrochloric acid and extracted with ethyl acetate. The extract was washed with water, dried over magnesium sulfate and concentrated in vacuo. The residue was triturated with diisopropyl ether to give 7β-[2-cyclopropyloxyimino-2-(2-formamidothiazol-4-yl)acetamido]-3-carbamoyloxymethyl-3-cephem-4-carboxylic acid (syn isomer) (2.1 g).

A mixture of 7β-[2-cyclopropyloxyimino-2-(2-formamidothiazol-4-yl)acetamido]-3-carbamoyloxymethyl-3-cephem-4-carboxylic acid (syn isomer) (2.0 g) and concentrated hydrochloric acid (1.2 ml) in a mixture of methanol (15 ml) and tetrahydrofuran (15 ml) was warmed at 33° to 35° C. for 1.5 hours. The mixture was poured into ice-water, adjusted to pH 7.5 with saturated aqueous solution of sodium bicarbonate and washed with ethyl acetate. The aqueous solution was adjusted to pH 2 with 1N hydrochloric acid and extracted with a mixture of ethyl acetate and tetrahydrofuran. The extract was washed with saturated aqueous solution of sodium chloride, dried over magnesium sulfate and concentrated in vacuo. The residue was triturated with ethyl acetate to give 7β-[2-(2-aminothiazol-4-yl)-2-(cyclopropyloxyimino)acetamido]-3-carbamoyloxymethyl-3-cephem-4-carboxylic acid (syn isomer) (0.86 g).

mp: 142° C. (dec.)

IR (Nujol): 1765, 1700, 1660, 1520 cm$^{-1}$

NMR (DMSO-d$_6$, δ): 0.50–0.90 (4H, m), 3.50 (2H, br s), 3.80–4.10 (1H, m), 4.57 and 4.87 (2H, ABq, J=14 Hz), 5.12 (1H, d, J=5 Hz), 5.72 (1H, dd, J=5 Hz and 8 Hz), 6.53 (2H, br s), 6.73 (1H, s), 7.15 (2H, br s), 9.42 (1H, d, J=8 Hz)

EXAMPLE 72

7β-[2-(2-Aminothiazol-4-yl)-2-(cyclopropyloxyimino)acetamido]-3-(5-methyl-1,3,4-thiadiazol-2-yl)thiomethyl-3-cephem-4-carboxylic acid (syn isomer) was obtained according to a similar manner to that of Example 71.

mp: 143° C. (dec.)

IR (Nujol): 1770, 1665, 1610, 1515 cm$^{-1}$

NMR (DMSO-d$_6$, δ): 0.50–0.90 (4H, m), 2.68 (3H, s), 3.53 and 3.77 (2H, ABq, J=18 Hz), 3.83–4.07 (1H, m), 4.16 and 4.52 (2H, ABq, J=14 Hz), 5.11 (1H, d, J=5 Hz), 5.72 (1H, dd, J=5 Hz and 8 Hz), 6.72 (1H, s), 7.13 (2H, br s), 9.43 (1H, d, J=8 Hz)

EXAMPLE 73

Phosphorus oxychloride (0.256 ml) was added to a solution of N,N-dimethylformamide (0.212 ml) in ethyl acetate (0.6 ml) under ice-cooling and the mixture was stirred at the same temperature for 10 minutes. To the mixture was added tetrahydrofuran (13 ml) and the mixture was stirred under ice-cooling for additional 10 minutes. To the mixture was added 2-cyclopropyloxyimino-2-(2-formamidothiazol-4-yl)acetic acid (syn isomer) (540 mg) and the mixture was stirred for 30 minutes under ice-cooling to give an activated acid solution. On the other hand, benzhydryl 7β-amino-3-[(Z)-2-(3-pyridyl)vinylthiomethyl]-3-cephem-4-carboxylate (1.03 g) was dissolved in a solution of bis(trimethylsilyl)acetamide (20 ml) in tetrahydrofuran (15 ml). To the solution was added the activated acid solution obtained above at −30° C. and the mixture was stirred for 30 minutes at −20° C. to −10° C. The mixture was poured into a mixture of ice-water (50 ml) and ethyl acetate (70 ml) and adjusted to pH 7 with saturated aqueous solution of sodium bicarbonate. The organic layer was separated, washed with saturated aqueous solution of sodium chloride, dried over magnesium sulfate and concentrated in vacuo. The residue was triturated with diethyl ether to give benzhydryl 7β-[2-cyclopropyloxyimino-2-(2-formamidothiazol-4-yl)acetamido]-3-[(Z)-2-(3-pyridyl)vinylthiomethyl]-3-cephem-4-carboxylate (syn isomer) (820 mg).

To a suspension of benzhydryl 7β-[2-cyclopropyloxyimino-2-(2-formamidothiazol-4-yl)acetamido]-3-[(Z)-2-3-pyridyl)vinylthiomethyl]-3-cephem-4-carboxylate (syn isomer) (1.32 g) in methanol (30 ml) was added concentrated hydrochloric acid (0.44 ml) and the mixture was stirred at 35° C. for an hour. The mixture was poured into a mixture of ethyl acetate and ice-water and adjusted to pH 7 with saturated aqueous solution of sodium bicarbonate. The organic layer was separated, washed with saturated aqueous solution of sodium chloride and water successively and concentrated in vacuo to give benzhydryl 7β-[2-(2-aminothiazol-4-yl)-2-(cyclopropyloxyimino)acetamido]-3-[(Z)-2-(3-pyridyl)-vinylthiomethyl]-3-cephem-4-carboxylate (syn isomer) (806 mg).

IR (Nujol): 1780, 1720, 1670, 1610, 1530 cm$^{-1}$

NMR (DMSO-d$_6$, δ): 0.50–0.90 (4H, m), 3.67 (2H, br s), 3.80–4.13 (3H, m), 5.25 (1H, d, J=5 Hz), 5.84 (1H, dd, J=5 Hz and 8 Hz), 6.37 and 6.52 (2H, ABq, J=9 Hz), 6.76 (1H, s), 6.95 (1H, s), 7.00–7.88 (14H, m), 8.27–8.60 (2H, m), 9.48 (1H, d, J=8 Hz)

EXAMPLE 74

Phosphorous oxychloride (0.31 ml) was added to a mixture of N,N-dimethylformamide (0.25 ml) and ethyl acetate (1 ml) under ice-cooling. The mixture was stirred at the same temperature for 10 minutes to give a suspension. To the suspension was added 2-cyclopropyloxyimino-2-(5-tritylamino-1,2,4-thiadiazol-3-yl)acetic acid (syn isomer) (1.18 g) and tetrahydrofuran (15 ml) and the mixture was stirred under ice-cooling for 30 minutes to give an activated acid solution. On the other hand, to a suspension of 1-(7β-amino-4-carboxy-3-cephem-3-yl)methyl]pyridinium chloride hydrochloride (1.3 g) in tetrahydrofuran (20 ml) was added N-trimethylsilylacetamide (8.5 g). The suspension was stirred at ambient temperature for an hour to give a clear solution. To the solution was added the activated acid solution prepared above at −30° C. and the mixture was stirred at −20° C. to −5° C. for 30 minutes and under ice-cooling for an hour. The mixture was poured into ethyl acetate (300 ml) to give precipitates. The precipitates were collected. To the precipitates was added a mixture of anisole (14 ml) and trifluoroacetic acid (4.3 ml) under ice-cooling. The mixture was stirred for 1.5 hours at ambient temperature. The mixture was concentrated in vacuo and poured into ice-water (50 ml). The mixture was adjusted to pH 5 with saturated aqueous solution of sodium bicarbonate. The aqueous solution was washed with ethyl acetate and subjected to column chromatography on a non-ionic adsorption resin "Diaion HP-20" (30 ml). After the column was washed with water, the elution was carried out with 2% isopropyl alcohol. The fractions containing the object compound were collected, combined, evaporated to remove isopropyl alcohol in vacuo, and finally lyophilized to give 7β-[2-(5-amino-1,2,4-thiadiazol-3-yl)-2-(cyclopropyloxyimino)acetamido]-3-(1-pyridinio)methyl-3-cephem-4-carboxylate (syn isomer)(260 mg).

mp: 150° C. (dec.)

IR (Nujol): 1770, 1660, 1610, 1520, 1350 cm$^{-1}$

NMR (DMSO-d$_6$, δ): 0.50–0.85 (4H, m), 3.07 and 3.53 (2H, ABq, J=18 Hz), 3.90–4.15 (1H, m), 5.06 (1H, d, J=5 Hz), 5.37 and 5.68 (2H, ABq, J=14 Hz), 5.67 (1H, dd, J=5 Hz and 8 Hz), 8.00–8.27 (2H, m), 8.15 (2H, br s), 8.43–8.70 (1H, m), 9.30–9.50 (2H, m), 9.42 (1H, d, J=8 Hz)

EXAMPLE 75

To a suspension of benzhydryl 7β-[2-(2-aminothiazol-4-yl)-2-(cyclopropyloxyimino)acetamido]-3-(5,6-dioxo-4-methyl-1,4,5,6-tertrahydro-1,2,4-triazin-3-yl)thiomethyl-3-cephem-4-carboxylate (syn isomer) (350 mg) in a mixture of anisol (0.5 ml) and methylene chloride (1.5 ml) was added trifluoroacetic acid (1 ml) under ice-cooling. The mixture was stirred at the same temperature for 30 minutes. The mixture was poured into diisopropyl ether (100 ml) and the resulted precipitate was collected. The precipitate was added to a mixture of ice-water and ethyl acetate and adjusted to pH 7 with saturated aqueous solution of sodium bicarbonate. The aqueous layer was separated and adjusted to pH 3 with 6N hydrochloric acid. The precipitate was collected and dried over phosphorus pentoxide to give 7β-[2-(2- aminothiazol-4-yl)-2-(cyclopropyloxyimino)acetamido]-3-(5,6-dioxo-4-methyl-1,4,5,6-tetrahydro-1,2,4-triazin-3-yl)thiomethyl-3-cephem-4-carboxylic acid (syn isomer) (157 mg).

mp: 170° C. (dec.)

IR (Nujol): 3250, 1770, 1700, 1590, 1530, 1350 cm$^{-1}$

NMR (DMSO-d$_6$, δ): 0.50–0.90 (4H, m), 3.29 (3H, s), 3.50–3.80 (2H, m), 3.80–4.30 (3H, m), 5.12 (1H, d, J=5 Hz), 5.76 (1H, dd, J=5 Hz, 8 Hz), 6.75 (1H, s), 9.47 (1H, d, J=8 Hz), 12.40 (1H, s)

The following compounds (Examples 76 to 79) were obtained according to a similar manner to that of Example 75.

EXAMPLE 76

7β-[2-(2-Aminothiazol-4-yl)-2-cyclopropyloxyimino)acetamido]-3-[(Z)-2-(3-pyridyl)vinylthio]-3-cephem-4-carboxylic acid (syn isomer)

mp: 175° C. (dec.)

IR (Nujol): 1770, 1665, 1530 cm$^{-1}$

NMR (DMSO-d$_6$, δ): 0.52–0.85 (4H, m), 3.68 and 4.06 (2H, ABq, J=18 Hz), 3.84–4.12 (1H, m), 5.19 (1H, d, J=5 Hz), 5.77 (1H, dd, J=5 Hz and 8 Hz), 6.75 (1H, s), 6.80 (2H, s), 7.40–7.60 (1H, m), 7.83–8.04 (1H, m), 8.39–8.55 (1H, m), 8.55–8.74 (1H, m), 9.52 (1H, d, J=8 Hz)

EXAMPLE 77

7β-[2-(2-Aminothiazol-4-yl)-2-(cyclopropyloxyimino)acetamido]-3-ethynyl-3-cephem-4-carboxylic acid (syn isomer).

mp: 143° C. (dec.)

IR (Nujol): 1775, 1660, 1515 cm$^{-1}$

NMR (DMSO-d$_6$, δ) 0.50–0.93 (4H, m), 3.47 and 3.77 (2H, ABq, J=18 Hz), 3.83–4.20 (1H, m), 4.49 (1H, s), 5.16 (1H, d, J=5 Hz), 5.78 (1H, dd, J=5 Hz and 8 Hz), 6.72 (1H, s), 7.14 (2H, br s), 9.48 (1H, d, J=8 Hz)

EXAMPLE 78

7β-[2-Cyclopropyloxyimino-2-(2-formamidothiazol-4-yl)acetamido]-3-[(Z)-2-(1-methyl-3-pyridinio)vinylthio]-3-cephem-4-carboxylate (syn isomer).

IR (Nujol): 1770, 1670, 1605, 1540 cm$^{-1}$

NMR (DMSO-d$_6$, δ): 0.50–0.95 (4H, m), 3.12 and 3.68 (2H, ABq, J=18 Hz), 3.92–4.18 (1H, m), 4.38 (3H, s), 5.03 (1H, d, J=5 Hz), 5.59 (1H, dd, J=5 Hz and 8 Hz), 6.63 and 6.98 (2H, ABq, J=12 Hz), 7.40 (1H, s), 7.83–8.10 (1H, m), 8.33–8.58 (1H, m), 8.52 (1H, s), 8.62–8.80 (1H, m), 9.12–9.28 (1H, m), 9.45 (1H, d, J=8 Hz)

EXAMPLE 79

7β-[2-Cyclopropyloxyimino-2-(2-formamidothiazol-4-yl)acetamido]-3-[(E)-2-(3)pyridyl)thiovinyl]-3-cephem-4-carboxylic acid (syn isomer).

NMR (DMSO-d$_6$, δ) 0.50–0.95 (4H, m), 3.55 and 4.05 (2H, ABq, J=18 Hz), 3.90–4.20 (1H, m), 5.14 (1H, d, J=5 Hz), 5.77 (1H, dd, J=5 Hz and 8 Hz), 7.00 (2H, s), 7.23–7.55 (1H, m), 7.38 (1H, s), 7.73–7.97 (1H, m), 8.37–8.63 (3H, m), 9.57 (1H, d, J=8 Hz)

EXAMPLE 80 p-Nitrobenzyl 7β-[2-cyclopropyloxyimino-2-(2-formamidothiazol-4-yl)acetamido]-3-methoxy-3-cephem-4-carboxylate (syn isomer) (0.9 g) was hydrogenated under 1 atmospheric pressure of hydrogen in the presence of 10% palladium on carbon (0.9 g) in a mixture of methanol (20 ml), tetrahydrofuran (400 ml), and acetic acid (0.01 ml) at ambient temperature for 2 hours. The catalyst was filtered off and washed successively diluted aqueous solution of sodium bicarbonate and tetrahydrofuran. The filtrate and the washings were combined and washed with ethyl acetate. The aqueous solution was adjusted to pH 3 with 1N hydrochloric acid and extracted with a mixture of ethyl acetate and tetrahydrofuran. The extract was washed with saturated aqueous solution of sodium chloride, dried over magnesium sulfate, concentrated in vacuo, and triturated in diisopropyl ether to give 7β-[2-cyclopropyloxyimino-2-(2-formamidothiazol-4-yl)acetamido]-3-methoxy-3-cephem-4-carboxylic acid (syn isomer) (0.35 g) as a solid.

NMR (DMSO-d$_6$, δ): 0.53–0.88 (4H, m), 3.60 (2H, br s), 3.71 (3H, s), 3.92–4.16 (1H, m), 5.13 (1H, d, J=5 Hz), 5.58 (1H, dd, J=5 Hz and 8 Hz), 7.44 (1H, s), 8.50 (1H, s), 9.52 (1H, d, J=8 Hz)

EXAMPLE 81

7β-[2-Cyclopropyloxyimino-2-(2-formamidothiazol-4-yl)acetamido]-3-chloro-3-cephem-4-carboxylic acid (syn isomer) was obtained according to a similar manner to that of Example 80.

NMR (DMSO-d$_6$, δ) 0.50–0.90 (4H, m), 3.62 and 4.02 (2H, ABq, J=18 Hz), 3.83–4.17 (1H, m), 5.26 (1H, d, J=5 Hz), 5.82 (1H, dd, J=5 Hz and 8 Hz), 7.41 (1H, s), 8.50 (1H, s), 9.67 (1H, d, J=8 Hz)

EXAMPLE 82

A solution of benzhydryl 7β-[2-(2-aminothiazol-4-yl)-2-(cyclopropyloxyimino)acetamido]-3-[(Z)-2-(3-pyridyl)vinylthiomethyl]-3-cephem-4-carboxylate (syn isomer) (0.69 g), anisole (0.69 ml), and trifluoroacetic acid (2.07 ml) in methylene chloride (1.38 ml) was stirred under ice-cooling for 40 minutes. The mixture was poured into diisopropyl ether to give a precipitate. The precipitate was dissolved into a mixture of water (30 ml) and ethyl acetate (15 ml) and the solution was adjusted to pH 7.1 with saturated aqueous solution of sodium bicarbonate. The aqueous layer was separated and adjusted to pH 5.6 with 1N hydrochloric acid. The solution was subjected to column chromatography on a non-ionic adsorption resin "Diaion HP-20" (12 ml). After the column was washed with water, the elution was carried out with 20% isopropyl alcohol. The fractions containing the object compound were combined, concentrated in vacuo to about 20 ml and lyophylized to give sodium 7β-[2-(2-aminothiazol-4-yl)-2-(cyclopropyloxyimino)acetamido]-3-[(Z)-2-(3-pyridyl)vinylthiomethyl]-3-cephem-4-carboxylate (syn isomer) (0.30 g).

mp: 160° C. (dec.)

IR (Nujol): 1760, 1660, 1600, 1530 cm$^{-1}$

NMR (DMSO-d$_6$, δ): 0.45–0.90 (4H, m), 3.48 (2H, br s), 3.58–4.37 (3H, m), 5.06 (1H, d, J=5 Hz), 5.62 (1H, dd, J=5 Hz and 8 Hz), 6.40 (1H, d, J=9 Hz), 6.73 (1H, s), 6.93–7.50 (2H, m), 7.82 (1H, d, J=9 Hz), 8.24–8.44 (1H, m), 8.52–8.67 (1H, m), 9.43 (1H, d, J=8 Hz)

EXAMPLE 83

To a suspension of benzhydryl 7β-[2-cyclopropyloxyimino-2-(2-formamidothiazol-4-yl)acetamido]-3-(1-methyl-3-pyridinio)thiomethyl-3-cephem-4-carboxylate trifluoroacetate (syn isomer) (1.65 g) in a mixture of anisol (1.3 ml) and methylene chloride (2.3 ml) was added trifluoroacetic acid (2.6 ml) under ice-cooling. The mixture was stirred at the same temperature for 30 minutes. The mixture was poured into diisopropyl ether (100 ml) and the resulted precipitate was collected and dried over phosphorus pentoxide to give trifluoroacetic acid salt of 7β-[2-cyclopropyloxyimino-2-(2-formamidothiazol-4-yl)acetamido]-3-(1-methyl-3-piridinio)thiomethyl-3-cephem-4-carboxylate (syn isomer) (1.27 g).

A mixture of trifluoroacetic acid salt of 7β-[2-cyclopropyloxyimino-2-(2-formamidothiazol-4-yl)acetamido]-3-(1-methyl-3-pyridinio)thiomethyl-3-cephem-4-carboxylate (syn isomer) (1.2 g) and concentrated hydrochloric acid (0.63 ml) in a mixture of methanol (10 ml) and tetrahydrofuran (5 ml) was warmed at 33° to 35° C. for 1.5 hours. The mixture was poured into ice-water, adjusted to pH 2.5 with saturated aqueous solution of sodium bicarbonate and washed with ethyl acetate. The aqueous solution was subjected to column chromatography on a non-ionic adsorption resin "Diaion HP-20" (30 ml). After the column was washed with water (300 ml), 1% isopropyl alcohol (60 ml), and 3% isopropyl alcohol (60 ml) successively, the elution was carried out with 5% isopropyl alcohol (250 ml) and 10% isopropyl alcohol (150 ml) successively. The fractions containing the object compound were collected, combined, concentrated in vacuo to about 100 ml and lyophylized to give 7β-[2-(2-aminothiazol-4-yl)-2-(cyclopropyloxyimino)acetamido]-3-(1-methyl-3-pyridinio)thiomethyl-3-cephem-4-carboxylate (syn isomer) (0.26 g).

mp: 138° C. (dec.)

IR (Nujol): 1760, 1660, 1600, 1515 cm⁻

NMR (D$_2$O, δ): 0.46–0.96 (4H, m), 3.43 and 3.73 (2H, ABq, J=18 Hz), 3.98 and 4.27 (2H, ABq, J=14 Hz), 4.03–4.25 (1H, m), 4.32 (3H, s), 5.11 (1H, d, J=5 Hz), 5.65 (1H, d, J=5 Hz), 6.94 (1H, s), 7.74–7.96 (1H, m), 8.27–8.62 (2H, m), 8.73–8.87 (1H, m)

EXAMPLE 84

A mixture of silver salt of (Z)-2-(3-pyridyl)ethenethiol (2.03 g) and sodium iodide (3.36 g) in acetonitrile (40 ml) was stirred for 20 minutes at 0° C. in the dark. To the mixture was added benzhydryl 7β-[2-cyclopropyloxyimino-2-(2-formamidothiazol-4-yl)acetamido]-3-chloromethyl-3-cephem-4-carboxylate (syn isomer) (2.03 g) at −20° C., and the mixture was stirred at 0° C. for 1.5 hours. The mixture was poured into a mixture of saturated aqueous solution of sodium chloride (200 ml) and ethyl acetate (100 ml). The insoluble material was filtered off and the organic layer was separated. The organic layer was washed with saturated aqueous solution of sodium chloride, dried over magnesium sulfate and concentrated in vacuo. The residue was triturated with diethyl ether to give benzhydryl 7β-[2-cyclopropyloxyimino-2-(2-formamidothiazol-4-yl)acetamido]-3-[(Z)-2-(3-pyridyl)vinylthiomethyl]-3-cephem-4-carboxylate (syn isomer) (1.41 g).

IR (Nujol): 1770, 1700, 1650, 1550, 1530 cm⁻¹

NMR (DMSO-d$_6$, δ): 0.50–0.90 (4H, m), 3.67 (2H, m), 3.76–4.20 (3H, m), 5.23 (1H, d, J=5 Hz), 5.87 (1H, dd, J=5 Hz, 8 Hz), 6.37 and 6.53 (2H, ABq, J=12 Hz), 6.93 (1H, s), 7.10–7.87 (13H, m), 8.23–8.63 (3H, m), 9.60 (1H, d, J=8 Hz)

The following compounds (Examples 85 to 111) were obtained according to a similar manner to that of Example 84.

EXAMPLE 85

7β-[2-Cyclopropyloxyimino-2-(2-trifluoroacetamidothiazol-4-yl)acetamido]-3-(1,3,4-thiadiazol-2-yl)thiomethyl-3-cephem-4-carboxylic acid (syn isomer).

IR (Nujol): 1780, 1715, 1660, 1580, 1540, 1410 cm⁻¹

NMR (DMSO-d$_6$, δ): 0.54–0.93 (4H, m), 3.56 and 3.83 (2H, ABq, J=118 Hz), 3.96–4.17 (1H, m), 4.25 and 4.59 (2H, ABq, J=14 Hz), 5.16 (1H, d, J=5 Hz), 5.81 (1H, dd, J=5 Hz and 8 Hz), 7.56 (1H, s), 9.53 (1H, s), 9.64 (1H, d, J=8 Hz)

EXAMPLE 86

7β-[2-(2,2-Dichlorocyclopropyloxyimino)-2-(2-trifluoroacetamidothiazol-4-yl)acetamido]-3-(1,3,4-thiadiazol-2-yl)thiomethyl-3-cephem-4-carboxylic acid (syn isomer).

IR (Nujol): 1770, 1710, 1660 cm⁻¹

NMR (DMSO-d$_6$, δ): 1.67–2.-20 (2H, m), 3.57 and 3.80 (2H, ABq, J=18 Hz), 4.26 and 4.57 (2H, ABq, J=14 Hz), 4.40–4.60 (1H, m), 5.17 (1H, d, J=5 Hz), 5.72–5.92 (1H, m), 7.65 and 7.70 (1H, each s), 9.57 (1H, s), 9.76 and 9.82 (1H, each d, J=8 Hz)

EXAMPLE 87

7β-[2-(2-Chlorocyclopropyloxyimino)-2-(2-trifluoroacetamidothiazol-4-yl)acetamido]-3-(1,3,4-thiadiazol-2-yl)thiomethyl-3-cephem-4-carboxylic acid (syn isomer, isomer A).

IR (Nujol): 1780, 1720, 1655, 1260, 1205 cm⁻¹

NMR (DMSO-d$_6$, δ): 1.00–1.80 (2H, m), 3.40–3.80 (1H, m), 3.58 and 3.85 (2H, ABq, J=18 Hz), 4.00–4.40 (1H, m), 4.26 and 4.61 (2H, ABq, J=14 Hz), 5.16 (1H, d, J=5 Hz), 5.81 (1H, dd, J=5 Hz, 8 Hz), 7.62 and 7.63 (1H, each s), 9.53 (1H, s), 9.66 (1H, d, J=8 Hz)

EXAMPLE 88

7β-[2-(2-Chlorocyclopropyloxyimino)-2-(2-trifluoroacetamidothiazol-4-yl)acetamido]-3-(1,3,4-thiadiazol-2-yl)thiomethyl-3-cephem-4-carboxylic acid (syn isomer, isomer B).

IR (Nujol): 1780, 1720, 1670, 1260, 1210 cm⁻¹

NMR (DMSO-d$_6$, δ): 1.00–1.60 (2H, m), 3.20–3.60 (1H, m), 3.55 and 3.82 (2H, ABq, J=18 Hz), 3.90–4.30 (1H, m), 4.25 and 4.60 (2H, ABq, J=14 Hz), 5.16 (1H, d, J=5 Hz), 5.81 (1H, dd, J=5 Hz, 8 Hz), 7.55 and 7.60 (1H, each s), 9.53 (1H, s), 9.68 (1H, d, J=8 Hz)

EXAMPLE 89

7β-[2-Cyclopropyloxyimino-2-(2-formamidothiazol-4yl)acetamido]-3-(1,3,4-thiadiazol-2-yl)thiomethyl-3-cephem-4-carboxylic acid (syn isomer).

IR (Nujol): 1780, 1655, 1540 cm⁻¹

NMR (DMSO-d$_6$, δ): 0.47–0.85 (4H, m), 3.49 and 3.75 (2H, ABq, J=18 Hz), 3.85–4.10 (1H, m), 4.16 and 4.52 (2H, ABq, J=14 Hz), 5.07 (1H, d, J=5 Hz), 5.72 (1H, dd, J=5 Hz, 8 Hz), 7.34 (1H, s), 8.42 (1H, s), 9.46 (1H, s), 9.49 (1H, d, J=8 Hz)

EXAMPLE 90

7β-[2-Cyclopropyloxyimino-2-(2-formamidothiazol-4-yl)acetamido]-3-(tetrazolo[1,5-b]pyridazin-6-yl)thiomethyl-3-cephem-4-carboxylic acid (syn isomer).

EXAMPLE 91

7β-[2-Cyclopropyloxyimino-2-(2-formamidothiazol-4-yl)acetamido]-3-(1,2,4-thiadiazol-5-yl)thiomethyl-3-cephem-4-carboxylic acid (syn isomer).

NMR (DMSO-d$_6$, δ): 0.50–0.90 (4H, m), 3.51 and 3.87 (2H, ABq, J=18 Hz), 3.90–4.30 (1H, m), 4.27 and 4.65 (2H, ABq, J=14 Hz), 5.27 (1H, d, J=5 Hz), 5.82 (1H, dd, J=5 Hz and 8 Hz), 7.43 (1H, s), 8.50 (1H, s), 8.70 (1H, s), 9.56 (1H, d, J=8 Hz)

EXAMPLE 92

7β-[2-Cyclopropyloxyimino-2-(2-formamidothiazol-4-yl)acetamido]-3-(1,2,3-thiadiazol-5-yl)thiomethyl-3-cephem-4-carboxylic acid (syn isomer).

NMR (DMSO-d$_6$, δ): 0.50–0.90 (4H, m), 3.63 (2H, br s), 3.85–4.20 (1H, m), 4.23 (2H, br s), 5.18 (1H, d, J=5 Hz), 5.78 (1H, dd, J=5 Hz and 8 Hz), 7.42 (1H, s), 8.50 (1H, s), 8.85 (1H, s), 9.58 (1H, d, J=8 Hz)

EXAMPLE 93

7β-[2-Cyclopropyloxyimino-2-(2-formamidothiazol-4-yl)acetamido]-3-(1-allyl-1H-tetrazol-5-yl)thiomethyl-3-cephem-4-carboxylic acid (syn isomer).

NMR (DMSO-d$_6$, δ): 0.50–0.90 (4H, m), 3.70 (2H, broad s), 3.90–4.17 (1H, m), 4.30 and 4.50 (2H, ABq, J=14 Hz), 4.87–5.47 (5H, m), 5.77–6.37 (2H, m), 7.40 (1H, s), 8.50 (1H, s), 9.57 (1H, d, J=8 Hz)

EXAMPLE 94

7β-[2-Cyclopropyloxyimino-2-(2-formamidothiazol-4-yl)acetamido]-3-(1,2,5-thiadiazol-3-yl)thiomethyl-3-cephem-4-carboxylic acid (syn isomer).

IR (Nujol): 1770, 1660, 1540 cm$^{-1}$

NMR (DMSO-d$_6$, δ): 0.50–0.90 (4H, m), 3.51 and 3.80 (2H, ABq, J=18 Hz), 3.90–4.20 (1H, m), 4.17 and 4.61 (2H, ABq, J=14 Hz), 5.14 (1H, d, J=8 Hz), 5.78 (1H, dd, J=5 Hz and 8 Hz),
7.42 (1H., s), 8.49 (1H, s), 8.74 (1H, s),
9.56 (1H, d, J=8 Hz)

EXAMPLE 95

Benzhydryl 7β-[2-cyclopropyloxyimino-2-(2-formamidothiazol-4-yl)acetamido]-3-(5,6-dioxo-4-methyl-1,4,5,6-tetrahydro-1,2,4-triazin-3-yl)thiomethyl-3-cephem-4-carboxylate (syn isomer).

IR (Nujol): 1775, 1700 cm$^{-1}$

NMR (DMSO-d$_6$, δ): 0.52–0.87 (4H, m), 3.19 (3H, s), 3.70 (2H, br s), 3.75–4.25 (3H, m), 5.20 (1H, d, J=5 Hz), 5.90 (1H, dd, J=5 Hz , 8 Hz), 6.92 (1H, s), 7.10–7.70 (11H, m), 8.47 (1H, s), 9.59 (1H, d, J=8 Hz), 12.39 (1H, s)

EXAMPLE 96

7β-[2-Cyclopropyloxyimino-2-(2-formamidothiazol-4-yl)acetamido]-3-(5,6-dioxo-2-methyl-1,2,5,6-tetrahydro-1,2,4-triazin-3-yl)thiomethyl-3-cephem-4-carboxylic acid (syn isomer).

IR (Nujol): 1780, 1665, 1545, 1345 cm$^{-1}$

NMR (DMSO-d$_6$, δ): 0.50–0.90 (4H, m), 3.40–3.90(2H, m), 3.58 (3H, s), 3.83–4.20 (1H, m), 4.06 and 4.41 (2H, ABq, J=14 Hz), 5.15 (1H, d, J=5 Hz), 5.81 (1H, dd, J=5 Hz, 8 Hz), 7.42 (1H, s), 8.48 (1H, s), 9.55 (1H, d, J=8 Hz), 12.48 (1H, br s)

EXAMPLE 97

7β-[2-(2-Aminothiazol-4-yl)-2-(cyclopropyloxyimino)acetamido]-3-(1,3,4-thiadiazol-2-yl)thiomethyl-3-cephem-4-carboxylic acid (syn isomer).

mp: 135° C. (dec.)

IR (Nujol): 1770, 1660 cm$^{-1}$

NMR (DMSO-d$_6$, δ): 0.52–0.85 (4H, m), 3.56 and 3.82 (2H, ABq, J=18 Hz), 3.90–4.20 (1H, m), 4.25 and 4.60 (2H, ABq, J=14 Hz), 5.14 (1H, d, J=5 Hz), 5.76 (1H, dd, J=5 Hz, 8 Hz), 6.83 (1H, s), 9.55 (1H, s), 9.57 (1H, d, J=8 Hz)

EXAMPLE 98

7β-[2-(2-Aminothiazol-4-yl)-2-(2,2-dichlorocyclopropyloxyimino)acetamido]-3-(1,3,4-thiadiazol-2-yl)thiomethyl-3-cephem-4-carboxylic acid (syn isomer).

mp: 163° C. (dec.)

IR (Nujol): 1770, 1670 cm$^{-1}$

NMR (DMSO-d$_6$, δ): 1.67–2.17 (2H, m), 3.53 and 3.80 (2H, ABq, J=18 Hz), 4.25 and 4.62 (2H, ABq, J=14 Hz), 4.34–4.60 (1H, m), 5.17 (1H, d, J=5 Hz), 5.67–5.87 (1H, m), 6.85 and 6.90 (1H, each s), 7.26 (2H, br s), 9.53–9.70 (1H, m), 9.55 (1H, s)

EXAMPLE 99

7β-[2-(2-Aminothiazol-4-yl)-2-(2-chlorocyclopropyloxyimino)acetamido]-3-(1,3,4-thiadiazol-2-yl)thiomethyl-3-cephem-4-carboxylic acid (syn isomer, isomer B).

mp: 161° C. (dec.)

IR (Nujol): 1770, 1660, 1620, 1520 cm$^{-1}$

NMR (DMSO-d$_6$, δ): 0.90–1.50 (2H, m), 3.10–3.40(1H, m), 3.54 and 3.80 (2H, ABq, J=18 Hz), 3.90–4.20 (1H, m), 4.24 and 4.58 (2H, ABq, J=14 Hz), 5.13 (1H, d, J=5 Hz), 5.75 (1H, dd, J=5 Hz, 8 Hz), 6.76 and 6.79 (1H, each s), 9.43 (1H, s), 9.49 (1H, d, J=8 Hz)

EXAMPLE 100

7η-[2-(2-Aminothiazol-4-yl)-2-(cyclopropyloxyimino)acetamido]-3-(tetrazolo[1,5-b]pyridazin-6-yl)thiomethyl-3-cephem-4-carboxylic acid (syn isomer)

mp: 170° C. (dec.)

IR (Nujol): 1765, 1665, 1515 cm$^{-1}$

NMR (DMSO-d$_6$, δ): 0.50–0.83 (4H, m), 3.58 and 3.85 (2H, ABq, J=18 Hz), 3.87–4.10 (1H, m), 4.16 and 4.62 (2H, ABq, J=14 Hz), 5.12 (1H, d, J=5 Hz), 5.76 (1H, dd, J=5 Hz, 8 Hz), 6.72 (1H, s), 7.15 (2H, br s), 7.72 (1H, d, J=10 Hz), 8.56 (1H, d, J=10 Hz), 9.45 (1H, d, J=8 Hz)

EXAMPLE 101

7β-[2-(2-Aminothiazol-4-yl)-2-(cyclopropyloxyimino)acetamido]-3-(1,2,4-thiadiazol-5-yl)thiomethyl-3-cephem-4-carboxylic acid (syn isomer).

mp: 156° C. (dec.)

IR (Nujol): 1770, 1670, 1620, 1530 cm$^{-1}$

NMR (DMSO-d$_6$, δ): 0.50–0.80 (4H, m), 3.51 and 3.78 (2H, ABq, J=18 Hz), 3.83–4.10 (1H, m), 4.26 and 4.60 (2H, ABq, J=14 Hz), 5.12 (1H, d, J=5 Hz), 5.73 (1H, dd, J=5 Hz, 8 Hz), 6.72 (1H, s), 7.14 (2H, br s), 8.67 (1H, s), 9.44 (1H, d, J=8 Hz)

EXAMPLE 102

7β-8-[2-(2-Aminothiazol-4-yl)-2-(cyclopropyloxyimino)acetamido]-3-(1,2,3-thiadiazol-5-yl)thiomethyl-3-4cephem-4-carboxylic acid (syn isomer).

mp: 145° C. (dec.)

IR (Nujol): 1770, 1665 cm$^{-1}$

NMR (DMSO-d$_6$, δ): 0.45–0.90 (4H, m), 3.52 and 3.77 (2H, ABq, J=18 Hz), 3.82–4.12 (1H, m), 4.25 (2H, br s), 5.17 (1H, d, J=5 Hz), 5.75 (1H, dd, J=5 Hz, 8 Hz), 6.75 (1H, s), 7.17 (2H, br s), 8.86 (1H, s), 9.48 (1H, d, J=8 Hz)

EXAMPLE 103

7β-8-[2-(2-Aminothiazol-4-yl)-2-(cyclopropyloxyimino)acetamido]-3-(5,6-dioxo-2-methyl-b 1,2,5,6-tetrahydro-1,2,4-triazin-3-yl)thiomethyl-3-cephem-4-carboxylic acid (syn isomer).

mp: 175° C. (dec.)

IR (Nujol): 5770, 1630, 1410, 1345 cm$^{-1}$

NMR (DMSO-d$_6$, δ): 0.50–0.90 (4H, m), 3.40–3.80 (2H, m), 3.59 (3H, s), 3.80–4.10 (1H, m), 4.07 and 4.40 (2H, ABq, J=14 Hz), 5.12 (1H, d, J=5 Hz), 5.76 (1H, dd, J=5 Hz, 8 Hz), 6.74 (1H, s), 7.16 (2H, br s), 9.45 (1H, d, J=8 Hz)

EXAMPLE 104

7β-[2-(2-Aminothiazol-4-yl)-2-(cyclopropyloxyimino)acetamido]-3-(1-allyl-1H-tetrazol-5-yl)thiomethyl-3-cephem-4-carboxylic acid (syn isomer).

mp: 136° C. (dec.)

IR (Nujol): 1770, 1665, 1530 cm$^{-1}$

NMR (DMSO-d$_6$, δ) 0.50–0.90 (4H, m), 3.52 and 3.78 (2H, ABq, J=18 Hz), 3.82–4.10 (1H, m), 4.18 and 4.46 (2H, ABq, J=14 Hz), 4.82–5.37 (5H, m), 5.60–6.20 (2H, m), 6.73 (1H, s), 7.16 (2H, br s), 9.46 (1H, d, J=8 Hz)

EXAMPLE 105

7β-8-[2-(2-Aminothiazol-4-yl)-2-(cyclopropyloxyimino)acetamido]-3-(1,2,5-thiadiazol-3-yl)thiomethyl-3-cephem-4-carboxylic acid (syn isomer).

mp: 164° C. (dec.)

IR (Nujol): 1775, 1670, 1630, 1535 cm$^{-1}$

NMR (DMSO-d$_6$, δ): 0.45–0.90 (4H, m), 3.50 and 3.78 (2H, ABq, J=18 Hz), 3.80–4.20 (1H, m), 4.15 and 4.59 (2H, ABq, J=14 Hz), 5.12 (1H, d, J=5 Hz), 5.72 (1H, dd, J=5 Hz and 8 Hz), 6.74 (1H, s), 6.80–7.70 (2H, br), 8.73 (1H, s), 9.46 (1H, d, J=8 Hz)

EXAMPLE 106

Benzhydryl 7β-[2-(2-aminothiazol-4-yl)-2(cyclopropyloxyimino)acetamido]-3-(5,6-dioxo-4-methyl-1,4,5,6-tetrahydro-1,2,4-triazin-3-yl)thiomethyl-3-cephem-4-carboxylate (syn isomer).

IR (Nujol): 1780, 1710, 1590, 1520 cm$^{-1}$

NMR (DMSO-d$_6$, δ): 0.50–0.90 (4H, m), 3.20 (3H, s), 3.71 (2H, br s), 3.80–4.30 (3H, m), 5.18 (1H, d, J=5 Hz), 5.87 (1H, dd, J=5 Hz, 8 Hz), 6.76 (1H, s), 6.93 (1H, s), 7.10–7.70 (10H, m), 9.50 (1H, d, J=8 Hz), 12.34 (1H, s)

EXAMPLE 107

7β-[2-(2-Aminothiazol-4-yl)-2-(cyclopropyloxyimino)acetamido]-3-(1-pyridinio)methyl-3-cephem-4-carboxylate (syn isomer).

mp: 150° C. (dec.)

IR (Nujol): 1760, 1600, 1520 cm$^{-1}$

NMR (D$_2$O-DSS, δ): 1.57–1.88 (4H, m), 3.17 and 3.65 (2H, ABq, J=18 Hz), 4.03–4.-24 (1H, m), 5.24 (1H, d, J=5 Hz), 5.32 and 5.57 (2H, ABq, J=14 Hz), 5.82 (1H, d, J=5 Hz), 7.00 (1H, s), 8.08 (2H, t, J=7 Hz), 8.57 (1H, t, J=7 Hz), 8.92 (2H, d, J=7 Hz)

EXAMPLE 108

7β-8-[2-(2-Aminothiazol-4-yl)-2-(2,2-dichlorocyclopropyloxyimino)acetamido]-3-(1-pyridinio)methyl-3-cephem-4-carboxylate (syn isomer).

IR (Nujol): 1760, 1620–1600 cm$^{-1}$

NMR (DMSO-d$_6$, δ: 1.60–2.17 (2H, m), 3.05 and 3.53 (2H, ABq, J=18 Hz), 4.20–4.55 (1H, m), 5.13 and 5.70 (2H, ABq, J=14 Hz), 5.05 (1H, d, J=5 Hz), 5.55–5.83 (1H, m), 6.70 and 6.83 (1H, each s), 7.23 (2H, br s), 8.02–8.30 (2H, m), 8.45–8.77 (1H, m), 9.03–9.73 (3H, m)

EXAMPLE 109

7β-[2-(2-Aminothiazol-4-yl)-2-(cyclopropyloxyimino)acetamido]-3-(3-methyl-1-pyridinio)methyl-3-cephem-4-carboxylate (syn isomer).

mp: 160° C. (dec.)

IR (Nujol): 3450–3150, 1770, 1670–1600, 1530, 1450 cm$^{-1}$

NMR (D$_2$O, δ): 0.50–0.90 (4H, m), 2.54 (3H, s), 3.17 and 3.63 (2H, ABq, J=18 Hz), 4.00–4.30 (1H, m), 5.24 (1H, d, J=5 Hz), 5.29 and 5.53 (2H, ABq, J=14 Hz), 5.82 (1H, d, J=5 Hz), (1H, s), 7.80–8.07 (1H, m), 8.25–8.48 (1H, m), 8.65–8.84 (2H, m)

EXAMPLE 110

7β-8-[2-(2-Aminothiazol-4-yl)-2-(cyclopropyloxyimino)acetamido]-3-[6,7-dihydro-5H-1-(1-pyrindinio)]methyl-3-cephem-4-carboxylate (syn isomer).

mp: 165° C. (dec.)

IR (Nujol): 3450–3100, 1770, 1660, 1610, 1530, 1445, 1280, 1210 cm$^{-1}$

NMR (D$_2$O, δ): 0.60–0.95 (4H, m), 2.10–2.50 (2H, m), 2.90–3.60 (6H, m), 4.00–4.30 (1H, m), 5.21 (1H, d, J=5 Hz), 5.26 and 5.51 (2H, ABq, J=14 Hz), 5.82 (1H, d, J=5 Hz), 6.97 (1H, s), 7.60–7.88 (1H, m), 8.13–8.46 (1H, m), 8.40–8.60 (1H, m)

EXAMPLE 111

7β-[2-(2-Aminothiazol-4-yl)-2-(cyclopropyloxyimino)acetamido]-3-(5,6-dioxo-4-methyl-1,4,5,6-tetrahydro-1,2,4-triazin-3-yl)thiomethyl-3-cephem-4-carboxylic acid (syn isomer).

mp: 170° C. (dec.)

IR (Nujol): 3250, 1770, 1700, 1590, 1530, 1350 cm$^{-1}$

NMR (DMSO-d$_6$, δ): 0.50–0.90 (4H, m), 3.29 (3H, s), 3.50–3.80 (2H, m), 3.80–4.30 (3H, m), 5.12 (1H, d, J=5 Hz), 5.76 (1H, dd, J=5 Hz, 8 Hz), 6.75 (1H, s), 9.47 (1H, d, J=8 Hz), 12.40 (1H, s)

EXAMPLE 112

A mixture of benzhydryl 7β-[2-cyclopropyloxyimino-2-(2-formamidothiazol-4-yl)acetamido]-3-chloromethyl-3-cephem-4-carboxylate (syn isomer) (1.5 g) and sodium iodide (2 g) in N,N-dimethylformamide (19 ml) was stirred at ambient temperature for 30 minutes. To the mixture was added 3-mercapto-1-methylpyridinium iodide (1.45 g) under ice-cooling. After stirred for an hour at the same temperature, the mixture was poured into water to give precipitates. The precipitates were washed with water and dissolved in a mixture of tetrahydrofuran and water (14:1 V/V) (50 ml). The solution was passed through a column of Amberlite IRA-400 (Trademark, manufactured by Rohm and Haas Co.) (trifluoroacetate type) (15 ml) and washed with a mixture of tetrahydrofuran and water (14:1 V/V) (45 ml). The eluent was concentrated under reduced pressure, triturated in diisopropyl ether, and dried over phosphorus pentoxide to give benzhydryl 7β-[2-cyclopropyloxyimino-2-(2-formamidothiazol-4-yl)acetamido]-3-(1-methyl-3-pyridinio)thiomethyl-3-cephem-4-carboxylate iodide (syn isomer) (1.70 g) as a solid.

NMR (DMSO-d$_6$, δ): 0.53–0.92 (4H, m), 3.30 (2H, br s), 3.83–4.36 (3H, m), 4.23 (3H, s), 5.27 (1H, d, J=5 Hz), 5.90 (1H, dd, J=5 Hz and 8 Hz), 6.86 (1H, s), 7.10–7.60 (11H, m), 7.70–8.00 (1H, m), 8.18–8.47 (1H, m), 8.53 (1H, s), 8.70–8.87 (1H, m), 8.93–9.07 (1H, m), 9.67 (1H, d, J=8 Hz)

EXAMPLE 113

To a suspension of silver (Z)-2-(1-methyl-3-pyridinio)ethanethiolate nitrate (4g, purity 60%) in a mixture of N,N-dimethylformamide (85 ml) and acetonitrile (30 ml) was added sodium iodide (11.9 g) at ambient temperature and the mixture was stirred at the same temperature for 20 minutes in the dark. To the mixture was added benzhydryl 7β-[2-cyclopropyloxyimino-2-(2-formamidothiazol-4-yl)acetamido]-3-chloromethyl-3-cephem-4-carboxylate (syn isomer) and the mixture was stirred at ambient temperature for an hour. The mixture was poured into water to give a precipitate. The precipitate was dissolved in N,N-dimethylformamide and the solution was dropwise added to large amount of diethyl ether to give a precipitate. The precipitate was collected and dried over phosphorus pentoxide to give crude benzhydryl 7β-[2-cyclopropyloxyimino-2-(2-formamidothiazol-4-yl)acetamido]-3-[(Z)-2-(1-methyl-3-pyridinio)vinylthiomethyl]-3-cephem-4-carboxylate iodide (syn isomer) (7.0 g). This compound was subjected to elimination reaction of the benzhydryl group by a similar manner described in Example 75 to give 7β-[2-cyclopropyloxyimino-2-(2-formamidothiazol-4-yl)acetamido]-3-[(Z)-2-(1-methyl-3-pyridinio)vinylthiomethyl]-3-cephem-4-carboxylate (syn isomer) (0.97 g).

IR (Nujol): 1750, 1640 cm$^{-1}$

NMR (DMSO-$d_6$, δ) 0.47–0.93 (4H, m), 3.17–3.80 (2H, hidden), 3.90–4.15 (1H, m), 4.19 and 4.48 (2H, ABq, J=14 Hz), 4.36 (3H, s), 5.03 (1H, d, J=5 Hz), 5.60 (1H, dd, J=5 Hz and 8 Hz), 6.58 (1H, d, J=12 Hz), 7.39 (1H, s), 7.92 (1H, d, J=12 Hz), 7.95–8.20 (1H, m), 8.43–8.63 (1H, m), 8.52 (1H, s), 8.63–8.86 (1H, m), 9.06–9.21 (1H, m), 9.51 (1H, d, J=8 Hz)

EXAMPLE 114

To a solution of benzhydryl 7β-[2-cyclopropyloxyimino-2-(2-formamidothiazol-4-yl)acetamido]-3-chloromethyl-3-cephem-4-carboxylate (syn isomer) (3 g) in methylene chloride (300 ml) was dropwise added a solution of m-chloroperbenzoic acid (0.79 g, 80% purity) in methylene chloride (10 ml) below 5° C. The mixture was stirred for 1.5 hours below 5° C. to give precipitates. The precipitates were collected, washed with methylene chloride, and dried over phosphorus pentoxide to give benzhydryl 7β-[2-cyclopropyloxyimino-2-(2-formamidothiazol-4-yl)acetamido]-3-chloromethyl-3-cephem-4carboxylate 1-oxide (syn isomer) as a solid.

A mixture of benzhydryl 7β-[2-cyclopropyloxyimino-2-(2-formamidothiazol-4-yl)acetamido]-3-chloromethyl-3-cephem-4-carboxylate 1-oxide (syn isomer) (2.5 g) and sodium iodide (3.4 g) in N,N-dimethylformamide (20 ml) was stirred at ambient temperature for 30 minutes. To the mixture was added isonicotinamide (0.91 g) under ice-cooling and the mixture was stirred for 2 hours at the same temperature. The mixture was poured into diisopropyl ether to give an oil. The oil was separated by decantation and triturated with water. The solid was dissolved in tetrahydrofuran, dried over magnesium sulfate, concentrated under reduced pressure, and triturated in diisopropyl ether to give benzhydryl 7β-[2-cyclopropyloxyimino-2-(2-formamidothiazol-4-yl)acetamido]-3-(4-carbamoyl-1-pyridinio)-methyl-3-cephem-4-carboxylate 1-oxide iodide (syn isomer) as a solid.

To a solution of benzhydryl 7β-[2-cyclopropyloxyimino-2-(2-formamidothiazol-4-yl)acetamido]-3-(4-carbamoyl-1-pyridinio)methyl-3-cephem-4-carboxylate 1-oxide iodide (syn isomer) (2.95 g) and N,N-dimethylaniline (1.4 ml) in N,N-dimethylformamide (30 ml) was dropwise added phosphorus trichloride (0.98 ml) at −30° C. The mixture was allowed to be stirred under ice-cooling for 1.5 hours and poured into diisopropyl ether to give an oil. The oil was separated by decantation and dissolved in a mixture of tetrahydrofuran and water (14:1 V/V) (60 ml). The solution was passed through a column of IRA-400 (trifluoroacetate type) (100 ml) and washed with a mixture of tetrahydrofuran and water (14:1 V/V) (50 ml). The eluent was concentrated under reduced pressure and triturated with diisopropyl ether to give benzhydryl 7β-[2-cyclopropyloxyimino-2-(2-formamidothiazol-4-yl)acetamido]-3-(4-carbamoyl-1-pyridinio)methyl-3-cephem-4-carboxylate trifluoroacetate (syn isomer) as a solid.

To a suspension of benzhydryl 7β-[2-cyclopropyloxyimino-2-(2-formamidothiazol-4-yl)acetamido]-3-(4-carbamoyl-1-pyridinio)methyl-3-cephem-4-carboxylate trifluoroacetate (syn isomer) (2.7 g) in a mixture of anisol (5 ml) and methylene chloride (10 ml) was added trifluoroacetic acid (10 ml) under ice-cooling. The mixture was stirred at the same temperature for 30 minutes. The mixture was poured into diisopropyl ether (800 ml) and the resulted precipitate was collected and dried over phosphorus pentoxide to give trifluoroacetic acid salt of 7β-[2-cyclopropyloxyimino-2-(2-formamidothiazol-4-yl)acetamido]-3-(4-carbamoyl-1-pyridinio)-methyl-3-cephem-4-carboxylate (syn isomer) (1.63 g).

A mixture of trifluoroacetic acid salt of 7β-[2-cyclopropyloxyimino-2-(2-formamidothiazol-4-yl)acetamido]-3-(4-carbamoyl-1-pyridinio)methyl-3-cephem-4-carboxylate (syn isomer) (1.6 g) and concentrated hydrochloric acid (0.76 ml) in a mixture of methanol (16 ml) and tetrahydrofuran (5 ml) was warmed at 33° to 35° C. for 1.5 hours. The mixture was poured into ice-water, adjusted to pH 2.5 with saturated aqueous solution of sodium bicarbonate and washed with ethyl acetate. The aqueous solution was subjected to column chromatography on a non-ionic adsorption resin "Diaion HP-20" (30 ml). After the column was washed with water (300 ml), 1% isopropyl alcohol (60 ml), and 3% isopropyl alcohol (60 ml) successively, the elution was carried out with 5% isopropyl alcohol (250 ml) and 10% isopropyl alcohol (150 ml) successively. The fractions containing the object compound were collected, combined, concentrated in vacuo to about 100 ml and lyophylized to give 7β-[2-(2-aminothiazol-4-yl)-2-(cyclopropyloxyimino)acetamido]-3-(4-carbamoyl-1-pyridinio)methyl-3-cephem-4-carboxylate (syn isomer) (180 mg).

mp: 140° C. (dec.)

IR (Nujol): 1770, 1670, 1610, 1530 cm$^{-1}$

NMR ($D_2O$, δ): 0.45–0.95 (4H, m), 3.21 and 3.68 (2H, ABq, J=18 Hz), 4.00–4.26 (1H, m), 5.25 (1H, d, J=5 Hz), 5.36 and 5.68 (2H, ABq, J=14 Hz), 5.81 (1H, d, J=5 Hz), 6.96 (1H, s), 8.33 and 9.10 (4H, ABq, J=6 Hz)

EXAMPLE 115

A solution of benzhydryl 7β-[2-cyclopropyloxyimino-2-(2-formamidothiazol-4-yl)acetamido]-3-[(Z)-2-(3pyridyl)vinylthio]-3-cephem-4-carboxylate (syn isomer) (5 g) and methyl iodide (5 ml) in N,N-dimethylformamide (25 ml) was stirred at ambient temperature for 2 hours in the dark. The solution was poured into large amount of ethyl acetate to give a precipitate. The precipitate was collected and dried over phosphorus pentoxide to give benzhydryl 7β-[2-cyclopropyloxyimino-2-(2-formamidothiazol-4-yl)acetamido]-3-[(Z)-2-(1-methyl-3-pyridinio)vinylthio]-3-cephem-4-carboxylate iodide (syn isomer) (5.32 g) as a solid.

IR (Nujol) 1770, 1660, 1520 cm$^{-1}$

NMR (DMSO-d$_6$, δ): 0.55–0.95 (4H, m), 3.13 and 3.61 (2H, ABq, J=18 Hz), 3.95–4.20 (1H, m), 4.33 (3H, s), 5.30 (1H, d, J=5 Hz), 5.93 (1H, dd, J=5 Hz and 8 Hz), 6.78 (1H, d, J=12 Hz), 6.90 (1H, s), 7.03–7.60 (12H, m), 7.90–8.20 (1H, m), 8.27–8.43 (1H, m), 8.49 (1H, s), 8.70–9.05 (2H, m), 9.65 (1H, d, J=8 Hz)

EXAMPLE 116

7↑-[2-Cyclopropyloxyimino-2-(2-formamidothiazol-4-yl)acetamido]-3-[(E)-2-(1-methyl-3-pyridinio)thiovinyl]-3-cephem-4-carboxylate hydriodide. (syn isomer) was obtained according to a similar manner to that of Example 115.

NMR (DMSO-d$_6$, δ): 0.53–0.90 (4H, m), 3.64 and 4.15 (2H, ABq, J=18 Hz), 3.93–4.15 (1H, m), 4.35 (3H, s), 5.25 (1H, d, J=5 Hz), 5.84 (1H, dd, J=5 Hz and 8 Hz), 7.20 (2H, s), 7.45 (1H, s), 7.93–8.13 (1H, m), 8.50–8.70 (1H, m), 8.52 (1H, s), 8.73–8.92 (1H, m), 9.00–9.15 (1H, m), 9.63 (1H, d, J=8 Hz)

EXAMPLE 117

To a solution of 7β-[2-(2-aminothiazol-4-yl)-2-(cyclopropyloxyimino)acetamido]-3-(1-pyridinio)methyl-3-cephem-4-carboxylic acid hydrogen sulfate (syn isomer) (3 g) in water (100 ml) was portionwise added sodium borohydride (1.9 g) under ice-cooling, keeping the pH of the reaction mixture at 6.5–7.0 with 1N hydrochloric acid. The mixture was stirred at the same condition for 2.5 hours. The mixture was adjusted to pH 2.5 with 6N hydrochloric acid and subjected to column chromatography on a non-ionic adsorption resin "Diaion HP-20" (90 ml). After the column was washed with water (630 ml), the elution was carried out with 20% methanol. The fractions containing the object compound were combined, concentrated in vacuo to about 100 ml, and lyophilized to give 7β-[2-(2-aminothiazol-4-yl)-2-(cyclopropyloxyimino)acetamido]-3-(1,2,3,6-tetrahydropyridin-1-yl)methyl-3-cephem-4-carboxylic acid (syn isomer) (0.35 g).

mp: 160° C. (dec.)

IR (Nujol): 1765, 1650, 1600, 1520, 1340 cm$^{-1}$

NMR (D$_2$O, δ): 0.60–1.00 (4H, m), 2.18–2.48 (2H, m), 2.80–3.20 (2H, m), 3.33 and 3.74 (2H, ABq, J=18 Hz), 3.37 (2H, br s), 3.71 (2H, s), 4.00–4.30 (1H, m), 5.22 (1H, d, J=5 Hz), 5.52–6.05 (3H, m), 7.01 (1H, s)

EXAMPLE 118

A suspension of 7β-[2-(2-aminothiazol-4-yl)-2-(cyclopropyloxyimino)acetamido]cephalosporanic acid (syn isomer) (0.97 g) in water was adjusted to pH 13 with 4N aqueous solution of sodium hydroxide under ice-cooling to give a clear solution. After stirred for 3 hours at the same temperature, the solution was adjusted to pH 4.5 with 1N hydrochloric acid and subjected to column chromatography on a non-ionic adsorption resin "Diaion HP-20" (40 ml). After the column was washed with water (80 ml), the elution was carried out with 10% isopropyl alcohol (120 ml). The fractions containing the object compound were combined and concentrated in vacuo to driness. The residue was triturated with acetone to give sodium 7β-[2-(2-aminothiazol-4-yl)-2-(cyclopropyloxyimino)acetamido]-3-hydroxymethyl-3-cephem-4-carboxylate (syn isomer) (1 g) as a solid.

mp: 142° C. (dec.)

IR (Nujol): 1750, 1650, 1600, 1525 cm$^{-1}$

NMR (D$_2$O, δ): 0.46–1.03 (4H, m), 3.44 and 3.70 (2H, ABq, J=18 Hz), 3.96–4.36 (3H, m), 5.18 (1H, d, J=5 Hz), 5.75 (1H, d, J=5 Hz), 7.02 (1H, s)

EXAMPLE 119

To a solution of 7β-[2-(2-aminothiazol-4-yl)-2-(cyclopropyloxyimino)acetamido]-3-(1-pyridinio)methyl-3-cephem-4-carboxylate (syn isomer) (750 mg) in water (50 ml) was added concentrated sulfuric acid (0.0679 ml). The solution was lyophilized to give 7β-[2-(2-aminothiazol-4-yl)-2-(cyclopropyloxyimino)acetamido]-3-(1-pyridinio)methyl-3-cephem-4-carboxylic acid hydrogen sulfate (863 mg).

NMR (D$_2$O, δ): 0.60–0.95 (4H, m), 3.31 and 3.75 (2H, ABq, J=18 Hz), 4.10–4.40 (1H, m), 5.32 (1H, d, J=5 Hz), 5.40 and 5.75 (2H, ABq, J=14 Hz), 5.85 (1H, d, J=5 Hz), 7.15 (1H, s) 7.95–8.25 (2H, m), 8.45–8.75 (1H, m), 8.80–9.05 (2H, m)

EXAMPLE 120

To a solution of 7β-[2-(2-aminothiazol-4-yl)-2-(cyclopropyloxyimino)acetamido]-3-(1-pyridinio)methyl-4-cephem-4-carboxylate (syn isomer) (750 mg) in water (50 ml) was added concentrated hydrochloric acid (0.265 ml). The solution was lyophilized to give 7β-[2-(2-aminothiazol-4-yl)-2-cyclopropyloxyimino)acetamido]-3-(1-pyridinio)methyl-3-cephem-4-carboxylic acid chloride hydrochloride (syn isomer) (874 mg).

NMR (D$_2$O, δ): 0.60–0.95 (4H, m), 3.32 and 3.75 2H, ABq, J=18 Hz), 4.10–4.30 (1H, m), 5.32 (1H, d, J=5 Hz), 5.41 and 5.77 (2H, ABq, J=14 Hz), 5.86 (1H, d, J=5 Hz), 7.16 (1H, s), 7.95–8.25 (2H, m), 8.45–8.75 (1H, m), 8.80–9.05 (2H, m)

What is claimed is:

1. A compound of the formula:

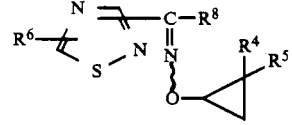

wherein
$R^4$ and $R^5$ are each hydrogen, halogen or phenylthio,
$R^6$ is amino or protected amino, and
$R^8$ is carboxy or protected carboxy, or a salt thereof.

* * * * *